(12) United States Patent
Benito Collado et al.

(10) Patent No.: US 8,232,289 B2
(45) Date of Patent: Jul. 31, 2012

(54) SPIROPIPERIDINE COMPOUNDS AS ORL-1 RECEPTOR ANTAGONISTS

(75) Inventors: Ana Belen Benito Collado, Madrid (ES); Nuria Diaz Buezo, Madrid (ES); Alma Maria Jimenez-Aguado, Madrid (ES); Celia Lafuente Blanco, Madrid (ES); Maria Angeles Martinez-Grau, Madrid (ES); Concepcion Pedregal-Tercero, Madrid (ES); Miguel Angel Toledo Escribano, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 85 days.

(21) Appl. No.: 12/943,187

(22) Filed: Nov. 10, 2010

(65) Prior Publication Data

US 2011/0118251 A1 May 19, 2011

Related U.S. Application Data

(60) Provisional application No. 61/298,629, filed on Jan. 27, 2010.

(30) Foreign Application Priority Data

Nov. 16, 2009 (EP) .................................... 09382246

(51) Int. Cl.
*A61K 31/438* (2006.01)
*C07D 409/14* (2006.01)
*C07D 405/14* (2006.01)

(52) U.S. Cl. .......................................... 514/279; 546/17
(58) Field of Classification Search ................... 546/17; 514/279
See application file for complete search history.

(56) References Cited

U.S. PATENT DOCUMENTS

| | | | |
|---|---|---|---|
| 6,635,653 B2 | 10/2003 | Goehring et al. |
| 6,686,370 B2 | 2/2004 | Kyle et al. |
| 6,869,960 B2 | 3/2005 | Ito et al. |
| 6,995,168 B2 | 2/2006 | Chen et al. |
| 7,081,463 B2 | 7/2006 | Battista et al. |
| 7,192,964 B2 | 3/2007 | Hashimoto et al. |
| 2009/0247561 A1 | 10/2009 | Zemolka |

FOREIGN PATENT DOCUMENTS

| | | |
|---|---|---|
| AU | 2003/235912 A1 | 11/2003 |
| EP | 0431943 A2 | 12/1991 |
| EP | 0431943 B1 | 12/1991 |
| WO | 02/088089 A1 | 7/2002 |
| WO | 03/095427 A1 | 11/2003 |
| WO | 2005/016913 A1 | 2/2005 |
| WO | 2005016913 A1 | 2/2005 |
| WO | 2005/066183 A1 | 7/2005 |
| WO | 2008/155132 A1 | 12/2008 |

OTHER PUBLICATIONS

Reinscheid, "The Orphanin FQ/Nociceptin Receptor as a Novel Drug Target in Psychiatric Disorders", CNS & Neurological Disorders—Drug Targets, 5, 219-224, (2006).

Li, et al., "Metabotropic Glutamate 5 Receptor Antagonism Is Associated with Antidepressant-Like Effects in Mice", The J. of Pharmacology and Exerimental Therapeutics, vol. 319: 1 (2006).

Przydzial, et al., "Nociceptin/Orphanin FQ Peptide Receptor as a Therapeutic Target for Obesity", Mini-Reviews in Med Chemistry, vol. 8: 796-811 (2008).

Ozaki, et al., "In vitro and in vivo pharmacological characterization of J-113397, a potent and selective non-peptidyl ORL1 Receptor Antagonist", European J. of Pharmacology 402: 45-53 (2000).

Oberdorf, et al., "Thiophene Bioisosteres of Spirocyclic # Receptor Ligands, 1.N-Substituted Spiro[piperidine-4,4#-thieno[3,2-c]pyrans]", J. of Medicinal Chemistry 51:(20):, 6531-6537 (2008).

Cheng, et al., "Relationship Between the Inhibition Constant (K) and the Concentration of Inhibitor Which Causes 50 Cent Inhibition (i50) of an Enzymatic Reaction" Biochemical Pharmacology, vol. 22: 3099-3108 (1973).

Chernet, et al., "Use of LC/MS to assess brain tracer distribution in preclinical, in vivo receptor occupancy studies: Dopamine D3, serotonin 2A and NK-1 receptors as examples". Life Sciences 78: 340-346 (2005).

Ciccocioppo, et al., "The nociceptin/orphanin FQ/NOP receptor system as a target for treatment of alcohol abuse: a review of recent work in alcohol-preferring rats", Physiology & Behavior, 79: 121-128 (2003).

DeLapp, et al, "Determination of [35S] Guanosine-5'-O-(3-thio)Triphosphate Binding Mediated by Cholinergic Muscarinic Receptors in Membranes from Chinese Hamster Ovary Cells and Rat Striatum Using an Anti-G Protein Scintillation Proximity Assay", The Journal of Pharmacology and Experimental Therapeutics, vol. 289: 2 (1999).

Yoshizumi, et al., "Design, synthesis, and structure-activity relationship study of a novel class of ORL1 receptor antagonists based on N-biarylmethyl spiropiperidine", Bioorganic & Medicinal Chemistry Letters, 18: 3778-3782 (2008).

Ardati, et al., "Interaction of [3H] Orphanin FQ and 125 I-Try14-Orphanin FQ with the Orphanin FQ Receptor: Kinetics and Modulation by Cations and Guanine Nucleotides" Molecular Pharmacology. 51:816-824 (1997).

*Primary Examiner* — Rita Desai
(74) *Attorney, Agent, or Firm* — R. Craig Tucker

(57) ABSTRACT

An ORL-1 receptor antagonist of the formula:

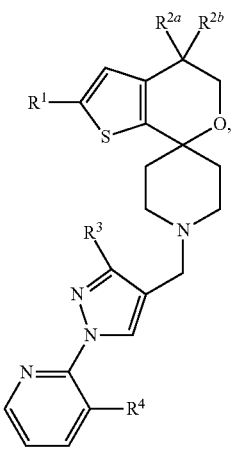

its uses, and methods for its preparation are described.

19 Claims, No Drawings

SPIROPIPERIDINE COMPOUNDS AS ORL-1 RECEPTOR ANTAGONISTS

This U.S. application filed under 35 U.S.C. 111(a) claims priority under 35 U.S.C. 119(e) to U.S. provisional application Ser. No. 61/298,629, filed Jan. 27, 2010, and under 35 U.S.C. 119(a) to European Patent Application No. 09382246.8, filed Nov. 16, 2009, with the Spanish Patent and Trademark Office.

Orphanin FQ (OFQ)/Nociceptin is a 17 amino acid peptide that has high affinity for the ORL1 G-protein coupled receptor (GPCR). The ORL1 receptor is a Class A GPCR that is expressed primarily in the central nervous system and peripheral nervous system as well as in the gastrointestinal tract, smooth muscle, and immune system. While related structurally to opioid peptides/receptors the OFQ/Nociceptin system exhibits no significant cross reactivity to classical opioid peptides/receptors and exhibits anti-opioid activity in vivo (for example ORQ/Nociceptin has been reported to exhibit antinociceptive properties).

Nociceptin/orphanin FQ receptor (NOC/OFQ) antagonists, specifically antagonists of the ORL-1 receptor have demonstrated anti-depressant activity and anorectic activity in numerous studies with animal models for depression and feeding behavior. As such, ORL-1 antagonists are deemed to be useful in the treatment of depression and/or the treatment of overweight, obesity, and/or weight maintenance post treatment for overweight or obesity.

WO 2003/095427 describes certain spiropiperidinyl compounds as ORL-1 antagonists for use as analgesics.

Yoshizumi, Takashi et al. (2008), *Design, synthesis, and structure-activity relationship study of a novel class of ORL-1 receptor antagonists based on N-biarylmethyl spiropiperidine*, Bioorganic & Medicinal Chemistry Letters vol. 18, pg. 3778-3782, describes certain N-biarylmethyl-spiropiperidine compounds as selective ORL-1 antagonists.

The present invention provides a family of 4',5'-dihydrospiro[piperidine-4,7'-thieno[2,3-c]pyran] compounds with high antagonist potency for the ORL-1 receptor and high in vivo ORL-1 receptor occupancy in the CNS. Additionally, certain of the compounds have a favorable cardiotoxicology profile as determined by selectivity over the hERG channel activity, as well as high selectivity over other physiologically important receptors (e.g. mu, kappa and delta opioids, serotonin, and dopamine receptors). Further, certain of the compounds of the present invention have favorable biopharmaceutical and pharmacokinetic properties (e.g. solubility, oral exposure, and CNS permeability). Certain of the compounds of the present invention exhibit reduced oxidative metabolism resulting in favorable oral bioavailability. Certain compounds have also demonstrated through animal models that the compounds of the present invention are useful for the treatment of migraine.

The present invention provides compounds of Formula I:

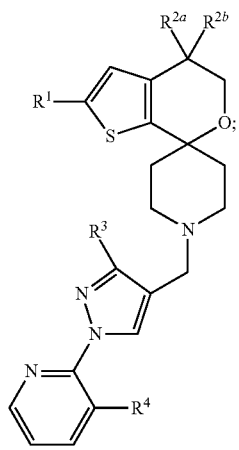

I wherein
$R^1$ is fluoro or chloro;
$R^{2a}$ and $R^{2b}$ are each hydrogen or are each fluoro;
$R^3$ is hydrogen, methyl, hydroxymethyl, or ($C_1$-$C_3$) alkoxymethyl;
$R^4$ is selected from the group consisting of fluoro, chloro, cyano, cyanomethyl, ($C_1$-$C_3$) alkyl, cyclopropyl, hydroxymethyl, methoxy, cyclopropylmethoxy, aminocarbonylmethoxy, ($C_1$-$C_3$) alkoxymethyl, cyclopropyloxymethyl, cyclopropylmethoxymethyl, 1-hydroxy-1-methylethyl, aminocarbonyloxymethyl, methylaminocarbonyloxymethyl, dimethylaminocarbonyloxymethyl, aminocarbonyl, aminocarbonylmethyl, —$CH_2$—$NR^5R^6$, hydroxyimine, methoxyimine, morpholin-4-yl, morpholin-4-ylmethyl, $Ar^1$, —$CH_2Ar^1$, tetrahydrofuran-2-yl, 3-oxomorpholin-4-ylmethyl, 2-oxopyrrolidin-1-ylmethyl, and 2-oxopiperidin-1-ylmethyl;
$R^5$ is hydrogen, $C_1$-$C_3$ alkyl, cyanomethyl, —$C(O)CH_3$, or aminocarbonylmethyl;
$R^6$ is hydrogen or methyl; and
$Ar^1$ is a moiety selected from the group consisting of imidizol-1-yl, imidizol-2-yl, 2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1,2,4-oxadiazol-5-yl; or a pharmaceutically acceptable salt thereof.

In another aspect of the invention there is provided a pharmaceutical composition comprising a compound of Formula I or a pharmaceutically acceptable salt thereof, in combination with a pharmaceutically acceptable carrier, diluent, or excipient. One embodiment of this aspect of the invention, the pharmaceutical composition further comprises at least one additional therapeutic ingredient, as for example an SSRI antidepressant, as for example fluoxetine. Furthermore, this aspect of the invention provides a pharmaceutical composition adapted for the treatment of depression comprising a compound of Formula I or a pharmaceutically acceptable salt thereof, in combination with one or more pharmaceutically acceptable excipients, carriers, or diluents thereof. In another embodiment of this aspect of the invention there is provided a pharmaceutical composition adapted for the treatment of overweight, obesity and/or weight maintenance, comprising a compound of Formula I or a pharmaceutically acceptable salt thereof, in combination with one or more pharmaceutically acceptable excipients, carriers, or diluents thereof. A further embodiment provides a pharmaceutical composition adapted for the treatment of migraine comprising a compound of Formula I or a pharmaceutically acceptable salt thereof, in combination with one or more pharmaceutically acceptable excipients, carriers, or diluents thereof.

The present invention also provides a method of treating depression in a mammal comprising administering to a mammal in need of such treatment an effective amount of a compound of Formula I or a pharmaceutically acceptable salt thereof. A further embodiment provides a method of treating depression in a mammal comprising administering to a mammal in need of such treatment an effective amount of a compound of Formula I, or a pharmaceutically acceptable salt thereof, and an effective amount of an SSRI antidepressant, or a pharmaceutically acceptable salt thereof, as for example fluoxetine. Other embodiments of the invention provide methods of treating overweight and/or obesity, and/or a method for weight maintenance comprising administering to a mammal in need of such treatment an effective amount of a compound of Formula I, or a pharmaceutically acceptable salt thereof. In one particular embodiment of these aspects of the invention, the mammal is a human.

This invention also provides a compound of Formula I or a pharmaceutically acceptable salt thereof for use in therapy. Within this aspect, the invention provides a compound of Formula I, or a pharmaceutically acceptable salt thereof, for use in the treatment of depression in mammals, particularly humans. The invention also provides a compound of Formula I, or a pharmaceutically acceptable salt thereof, in combination with an SSRI antidepressant, or a pharmaceutically acceptable salt thereof, as for example fluoxetine, for use in the treatment of depression in mammals, particularly humans. Further, this aspect of the invention includes any one of the following: a compound of Formula I, or a pharmaceutically acceptable salt thereof, for use in the treatment of overweight; a compound of Formula I, or a pharmaceutically acceptable salt thereof, for use in the treatment of obesity; a compound of Formula I, or a pharmaceutically acceptable salt thereof, for use in the maintenance of weight (for weight maintenance), particularly after treatment for overweight or obesity; a compound of Formula I, or a pharmaceutically acceptable salt thereof, for use in the treatment of migraine.

Another aspect of this invention provides the use of a compound of Formula I, or a pharmaceutically acceptable salt thereof, in the manufacture of a medicament for the treatment of depression. Another embodiment of the invention provides the use of a compound of Formula I, or a pharmaceutically acceptable salt thereof, in the manufacture of a medicament for the treatment of overweight, obesity, and/or the maintenance of weight. Yet another embodiment of the invention provides the use of a compound of Formula I, or a pharmaceutically acceptable salt thereof, in the manufacture of a medicament for the treatment of migraine.

Compounds of this invention are bases, and accordingly react with a number of organic and inorganic acids to form pharmaceutically acceptable salts. Pharmaceutically acceptable salts of each of the compounds of the present invention are contemplated within the scope of the present application. The term "pharmaceutically acceptable salt" as used herein, refers to any salt of a compound of Formula I that is substantially non-toxic to living organisms. Such salts include those listed in *Journal of Pharmaceutical Science*, 66, 2-19 (1977), which are known to the skilled artisan.

Abbreviations used herein are defined as follows:
"BSA" means bovine serum albumin.
"mCPP" means meta-chlorophenylpiperazine, a non-selective serotonin receptor agonist.
"EDTA" means ethylene diamine tetraacetic acid.
"EGTA" means ethylene glycol tetraacetic acid.
"GTP" means guanosine triphosphate.
"HEPES" means 4-(2-hydroxyethyl)-1-piperazineethanesulfonic acid.
"HPLC" means high-pressure liquid chromatography.
"$IC_{50}$" means the concentration at which 50% of the maximum inhibition is achieved.
"LC/MS" means liquid chromatography followed by mass spectroscopy.
"LC/MS/MS" means liquid chromatography followed by mass spectroscopy, followed by a second ionizing mass spectroscopy.
"mFST" means mouse forced swim test; an animal model for antidepressant activity.
"MS" means mass spectroscopy.
"MS (ES+)" means mass spectroscopy using electrospray ionization.
"NMR" means nuclear magnetic resonance.
"RO Tracer" means 2-[(2-Fluorophenyl)methyl]-3-(2-fluorospiro[4,5-dihydrothieno[2,3-c]pyran-7,4'-piperidine]-1'-yl)-N,N-dimethyl-propanamide.
"RO" means receptor occupancy.
"SCX column" means strong cation exchange column.
"SNAr" means nucleophilic aromatic substitution.
"SSRI" means selective serotonin reuptake inhibitor.
"tBu" means a tertiary-butyl moiety.
"TLC" means thin layer chromatography.
"XRD" means X-Ray Diffraction.

Preferred compounds of the present invention are compounds wherein:
1) $R^1$ is chloro;
2) $R^{2a}$ and $R^{2b}$ are each fluoro;
3) $R^1$ is chloro and $R^{2a}$ and $R^{2b}$ are each fluoro;
4) $R^1$ is fluoro and $R^{2a}$ and $R^{2b}$ are each hydrogen;
5) $R^3$ is hydrogen, methyl, hydroxymethyl, or methoxymethyl;
6) $R^3$ is methyl;
7) $R^3$ is hydroxymethyl;
8) $R^1$ is chloro, $R^{2a}$ and $R^{2b}$ are each fluoro, and $R^3$ is methyl;
9) $R^1$ is chloro, $R^{2a}$ and $R^{2b}$ are each fluoro, and $R^3$ is hydroxymethyl;
10) $R^4$ is fluoro, hydroxymethyl, methoxymethyl, or pyrazol-1-ylmethyl;
11) $R^4$ is fluoro;
12) $R^4$ is hydroxymethyl;
13) $R^4$ is methoxymethyl;
14) $R^4$ is pyrazol-1-ylmethyl;
15) any one of preferred embodiments 1) through 9) wherein $R^4$ is fluoro;
16) any one of preferred embodiments 1) through 9) wherein $R^4$ is hydroxymethyl;
17) any one of preferred embodiments 1) through 9) wherein $R^4$ is methoxymethyl;
18) any one of preferred embodiments 1) through 9) wherein $R^4$ is pyrazol-1-ylmethyl;

Certain preferred compounds are
[2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol;
2-chloro-4,4-difluoro-1'-[[3-methyl-1-[3-(pyrazol-1-ylmethyl)-2-pyridyl]pyrazol-4-yl]methyl]spiro[5H-thieno[2,3-c]pyran-7,4'-piperidine]; and
[4-[(2-chloro-4,4-difluoro-spiro[5H-thieno[2,3-c]pyran-7,4'-piperidine]-1'-yl)methyl]-1-(3-fluoro-2-pyridyl)pyrazol-3-yl]methanol;
or a pharmaceutically acceptable salt thereof (i.e. Examples 1, 23, 53, 62, and 63)

One particularly preferred compound of the present invention is [2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol, or a pharmaceutically acceptable salt thereof, as for example the L-tartrate salt and/or the HCl salt, as exemplified in examples 1, 62 and 63.

Compounds wherein $R^{2a}$ and $R^{2b}$ are each fluoro are preferred because the compounds have a more favorable pharmacokinetic profile, being more stable to oxidative metabolism. This has the general effect of improving the oral bioavailability of the compounds.

General Chemistry

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. All substituents, unless otherwise indicated, are as previously defined, and all reagents are well known and appreciated in the art.

Scheme 1

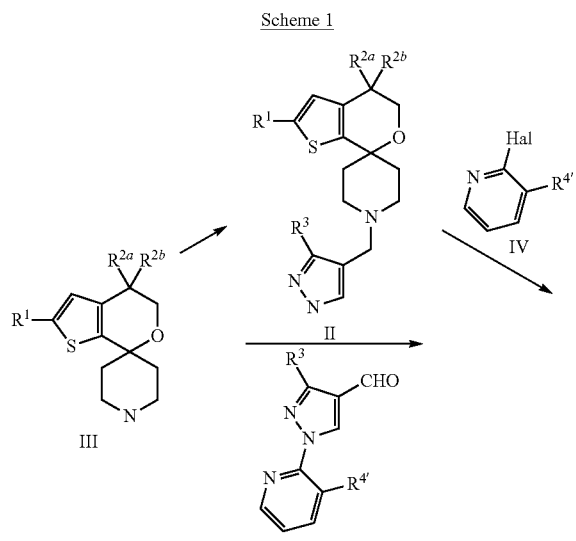

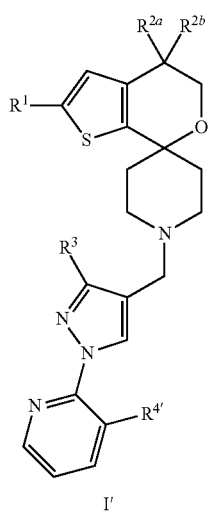

By using reductive amination reaction conditions, compound III is reacted with an appropriately substituted pyrazole carbaldehyde and a reducing reagent such as sodium triacetoxyborohydride, in a suitable solvent such as tetrahydrofuran at ambient temperature to provide compound II. Under an appropriate coupling condition, compound II is coupled with compound IV, wherein Hal is chloro, bromo, or iodo, with a suitable catalyst such as copper iodide, an appropriate base such as potassium carbonate, in a solvent such as toluene at elevated temperature to give compound I', wherein $R^{4'}$ is $R^4$ or a precursor of $R^4$. When Hal on compound IV is F or Cl, nucleophilic aromatic substitution (SNAr) is an alternative method to make compound I'. More specifically, compound II can react with compound IV in an appropriate solvent such as dimethylformamide with a suitable base such as potassium carbonate at elevated temperature to provide compound I'. Compound III can also react with an appropriately substituted aldehyde compound V under reductive amination conditions as above to give the desired compound I'. When $R^{4'}$ is a precursor to $R^4$, it is then converted to $R^4$ by known methods.

Scheme 2

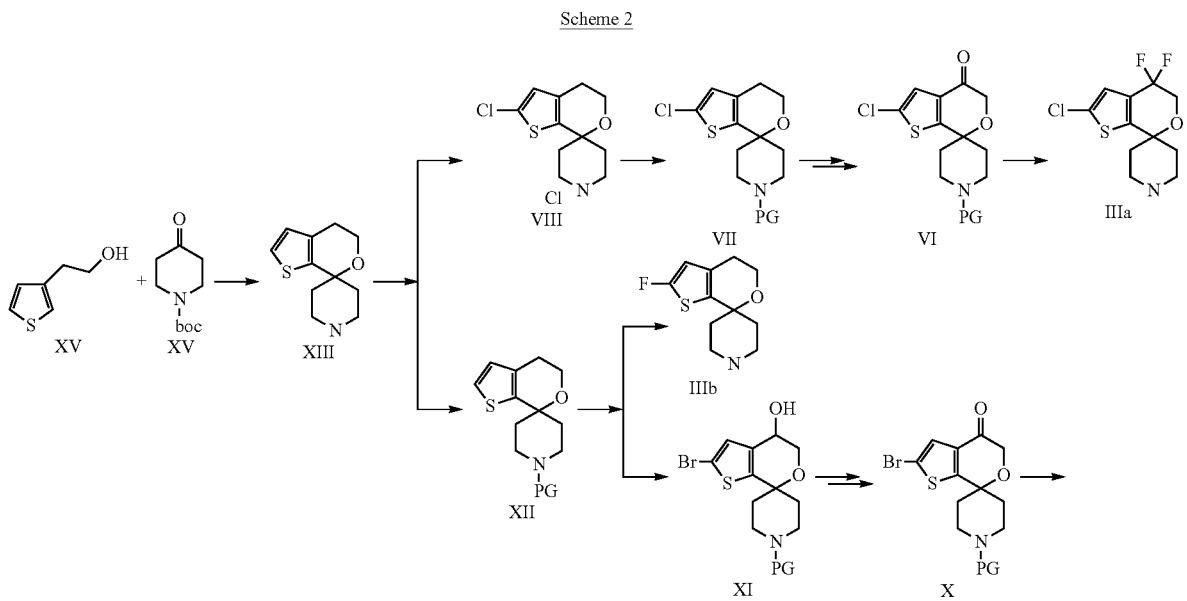

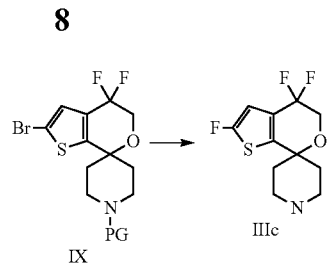

Compounds IIIa, IIIb, and IIIc can be made as illustrated in Scheme 2. Compounds XIV and XV are reacted in an appropriate solvent such as dichloromethane in the presence of a suitable acid such as trifluoroacetic acid. The resultant trifluoroacetate is basified with aqueous sodium hydroxide solution to give compound XIII as a free base. Compound XIII in a suitable solvent such as methyl t-butyl ether is treated with a solution of sulfuryl chloride in acetic acid at ambient temperature to give compound VIII as a hydrochloride salt. Compound VIII is then protected with a nitrogen protecting group under conditions well known to the skilled artisan to give compound VII. (For example, see: Greene and Wuts, *Protective Groups in Organic Synthesis*, Third Edition, Chapters 2 and 7, John Wiley and Sons Inc., (1999)). Typically, the protecting group is a Boc (tert-Butyloxy carbonyl) group. Compound VII is reacted with N-bromosuccinimide in an appropriate solvent such as chlorobenzene with irradiation of a light source to give a bromide compound, which is then treated with a base solution such as aqueous sodium bicarbonate to afford a hydroxyl compound. With or without isolation, the hydroxyl compound can be further oxidized under suitable oxidation conditions such as in potassium bromide, tetramethylpiperidine-N-oxide, and aqueous sodium hypochloride solution to provide the desired ketone compound VI. Compound VI is then reacted with (bis(2-methylethyl)amino)sulfur trifluoride in an appropriate solvent such as tetrahydrofuran at elevated temperature, the product obtained is de-protected to provide compound IIIa.

Compound of formula XIII is protected to give compound XII with a similar method to that used to make compound VII. Compound XII in an appropriate solvent such as tetrahydrofuran at lowered temperature is treated with a suitable base such as lithium tetramethylpiperidine, followed by addition of N-fluorobenzenesulfonimide to afford a fluoride compound, which is de-protected with aqueous HCl and basified with aqueous NaOH solution to provide compound IIIb.

By the same method used for making compound VI above, compound IX can be obtained from compound XII through three-step synthesis, such as bromination, hydroxylation, and oxidation. Each intermediate can be isolated as pure compound for further reaction or reacted without isolation as described in the synthesis of compound VI. Compound IX is then treated with a suitable halogen-metal exchange reagent such as butyl lithium in proper solvent such as tetrahydrofuran under lowered temperature, followed by a fluorinating reagent such as N-fluoro-benzenesulfonimide to afford the desired fluorinated product, which is then de-protected appropriately to give the desired compound IIIc.

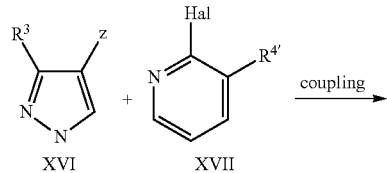

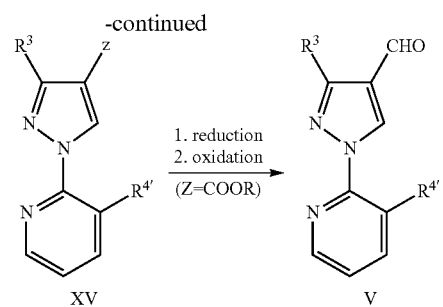

Z=CHO, COOR
R=Alkyl

Compounds of formula V can be made as illustrated in Scheme 3. Compound XVI is reacted with compound XVII to afford compound of formula XV under SNAr or coupling conditions described above for the conversion of compound II to compound I'. When Z is an ester group, it can be reduced to an alcohol first with a proper reducing reagent such as lithium aluminum hydride in appropriate solvent such as tetrahydrofuran. The alcohol is then oxidized to aldehyde with a proper oxidation reagent such as manganese (IV) oxide in a solvent such as dichloromethane.

When $R^{4'}$ is the precursor of $R^4$, the transformation of $R^{4'}$ to $R^4$ will include but not limited to reactions such as reductive amination to provide a desired new amine; reduction of an ester, ketone, or aldehyde to an alcohol, which can be further converted to an alkoxy compound or a carbamate; reduction of a nitrile to an amide or an amine; the transformation of an ester to a heterocycle such as oxadiazol under proper condition. (For more examples, see: Richard C. Larock, *Comprehensive Organic Transformations*, Second Edition, Chapters 2 and 7, John Wiley and Sons Inc., (1999)).

The following Preparations and Examples are illustrative of methods useful for the synthesis of the compounds of the present invention. The names for many of the compounds illustrated in the preparations and examples are provided from structures drawn with 'Symyx Draw 3.1' or 'Autonom 2000 Name'.

Preparation 1: 4',5'-Dihydrospiro[piperidine-4,7'-thieno[2,3-c]pyran]

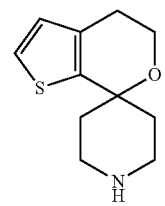

3-Thiopheneethanol (123.03 mL, 1.11 mol) is added to a solution of N-tert-butoxycarbonyl-4-piperidone (185 g, 928.48 mmol) in dichloromethane (1300 mL) and stirred at room temperature. Then trifluoroacetic acid (280.82 mL, 3.71 moles) is added dropwise (5 min) while cooling with an ice/water bath (internal temperature=14° C.-30° C., caution:

CO₂ evolution). The reaction mixture is gradually warmed to ambient temperature and stirred at that temperature for 20 hr. The solvent is evaporated to provide a beige crystalline solid upon cooling in vacuo. The solid is slurried in methyl t-butyl ether (200 mL), filtered, washed with methyl t-butyl ether (2×1000 mL) and dried under vacuum to afford 4',5'-dihydrospiro[piperidine-4,7'-thieno[2,3-c]pyran]-1-ium trifluoroacetate as a white solid in 95% yield. MS=(m/z): 210 (M+1). 10 M sodium hydroxide (220.36 mL, 2.20 mol) is added to a stirred suspension of 4',5'-dihydrospiro[piperidine-4,7'-thieno[2,3-c]pyran]-1-ium trifluoroacetate (285 g, 881.44 mmol) in dichloromethane (1 L) with cooling (ice/water bath) and the resulting mixture is stirred till a biphasic mixture is obtained. The phases are separated and the aqueous layer is extracted with dichloromethane (2×200 mL). Combined organics are concentrated under vacuum to obtain a thick oil which is triturated with water to obtain a light yellow precipitate. The precipitate is filtered, washed with water (300 mL) and hexane (200 mL) and dried under vacuum at 35° C. for 20 hr. to yield the title compound as a light yellow solid in 86% yield. MS (m/z): 210 (M+1).

Preparation 2: tert-Butyl spiro[4,5-dihydrothieno[2,3-c]pyran-7,4'-piperidine]-1'-carboxylate

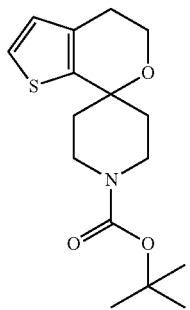

Spiro[4,5-dihydrothieno[2,3-c]pyran-7,4'-piperidine] (60 g, 286.6 mmol) in 2-methyltetrahydrofuran (600 mL) is stirred at 22° C. for 10 min. Then, tert-butoxycarbonyl tert-butyl carbonate (65.6 g, 301 mmol) in 2-methyltetrahydrofuran (300 mL) is added dropwise. After 12 hr., an aqueous solution of sodium chloride (250 mL) is added and the organic layer is separated. The aqueous layer is washed twice with 2-methyltetrahydrofuran (2×50 mL) and the organic layers are combined and washed with brine, dried over sodium sulfate, filtered, and concentrated under reduced pressure to give the title compound in 99% yield. MS (m/z): 310 (M+1).

Preparation 3: 2-Fluorospiro[4,5-dihydrothieno[2,2-c]pyran-7,4'-piperidine]

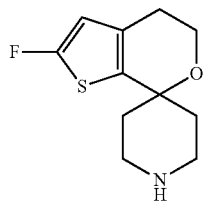

1. tert-Butyl 2-fluorospiro[4,5-dihydrothieno[2,3-c]pyran-7,4'-piperidine]-1'-carboxylate 2,2,6,6-Tetramethylpiperidine (18.7 mL, 110.5 mmol) is added over tetrahydrofuran (200 mL), and solution is cooled under nitrogen at −78° C. 2.5 M solution of butyl lithium in hexane (37.2 mL, 93 mmol) is added and mixture is stirred for 30 min at −78° C. Over the fresh lithium 2,2,6,6-tetramethylpiperidine solution is added a solution of tert-butyl spiro[4,5-dihydrothieno[2,3-c]pyran-7,4'-piperidine]-1'-carboxylate (20 g, 58.2 mmol) in tetrahydrofuran (90 mL) keeping temperature below −70° C. After 20 min. a solution of N-fluorobenzenesulfonimide (30.26 g, 93.07 mmol) in tetrahydrofuran (200 mL) previously cooled under nitrogen at −20° C. is added via cannula. After 1 hr. stirring, water (20 mL) and aqueous solution of ammonium chloride (50 mL) are added. Then, organic layer is separated and the aqueous is washed twice with methyl t-butyl ether (2×25 mL). Organics are combined and solvent is evaporated under reduced pressure. Crude material is purified by normal phase HPLC using hexane/methyl t-butyl ether as solvents to give tert-butyl 2-fluorospiro[4,5-dihydrothieno[2,3-c]pyran-7,4'-piperidine]-1'-carboxylate in 50% yield. MS (m/z): 328 (M+1).

2. 2-Fluorospiro[4,5-dihydrothieno[2,2-c]pyran-7,4'-piperidine]

37% Hydrochloric acid (11.75 mL, 125.22 mmol) is added to a solution of tert-butyl 2'-fluoro-4',5'-dihydro-1H-spiro[piperidine-4,7'-thieno[2,3-c]pyran]-1-carboxylate (8.2 g, 25.04 mmol) in isopropyl alcohol (57.4 mL) at 45° C. The resulting solution is stirred at 45° C. for 6.5 hr. The solvent is concentrated to a yellow suspension. Water (50 mL) is added and the mixture is basified with 5N aqueous solution of sodium hydroxide. The aqueous phase is extracted with ethyl acetate (3×100 mL) and the combined organic extracts are washed with brine (50 mL), dried over sodium sulfate, filtered and concentrated under reduced pressure to give the title compound in 96% yield. MS (m/z): 228 (M+1).

Preparation 4: 2'-Chloro-4',5'-dihydrospiro[piperidine-4,7'-thieno[2,3-c]pyran]hydrochloride

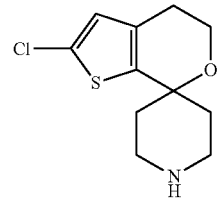

A solution of 4',5'-dihydrospiro[piperidine-4,7'-thieno[2,3-c]pyran] (50 g, 238.88 mmol) in a mixture of acetic acid (400 mL) and methyl t-butyl ether (40 mL) is cooled to 15° C. Then, a solution of sulfuryl chloride (21.20 mL, 262.77 mmol) in acetic acid (100 mL) is added dropwise in 40 min at that temperature (internal temperature=15° C.-22° C.) and the mixture is stirred at room temperature for 20 hr. Then, a solution of sulfuryl chloride (11.56 mL, 143.33 mmol) in acetic acid (50 mL) is added dropwise at room temperature. The reaction mixture is stirred at room temperature for 30 min. and then it is added dropwise (30 min) over methyl t-butyl ether (1 L) cooling with ice/water bath with stirring. A white suspension is formed and the solid is filtered. To obtain a second crop of material, the filtrate is concentrated (refilling with methyl t-butyl ether via rotavap). Resulting solid is suspended in methyl t-butyl ether (300 mL), suspension is stirred at reflux (bath: 100° C.) and methanol (30 mL) is added till a cloudy suspension is formed. Then, the suspension is cooled to room temperature overnight. The suspension is further cooled in a ice/water bath and filtered. Solid is washed with methyl t-butyl ether (50 mL) and combined with first crop to give the title compound in a 60% yield. MS (m/z): 244 (M+1).

Preparation 5: 2'-Chloro-4',4'-difluoro-4',5'-dihydrospiro[piperidine-4,7'-thieno[2,3-c]pyran]

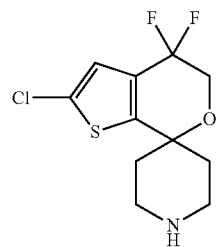

1. tert-Butyl 2-chlorospiro[4,5-dihydrothieno[2,3-c]pyran-7,4'-piperidine]-1'-carboxylate To a suspension of 2-chlorospiro[4,5-dihydrothieno[2,2-c]pyran-7,4'-piperidine]hydrochloric salt (140 g, 0.49 moles) in dichloromethane (1.12 L) is added triethylamine (67.25 mL, 1.05 mole), 4-pyridinamine, N,N-dimethyl-(3.05 g, 0.025 mole) and di-t-butyldicarbonate (111.22 g, 0.509 mole) in portions and the resulting mixture is stirred at room temperature overnight. The reaction is washed with 1N HCl (2×) and water. The organic phase is dried over magnesium sulfate, filtered and concentrated under reduced pressure to afford tert-butyl 2-chlorospiro[4,5-dihydrothieno[2,3-c]pyran-7,4'-piperidine]-1'-carboxylate in 53% yield. MS (m/z): 244 (M+1-Boc).

2. tert-Butyl 1,4'-oxo-2'-chloro-4',5'-dihydrospiro[piperidine-4,7'-thieno[2,3-c]pyran]-1-carboxylate In a 5 L jacketed reactor, N-bromosuccinimide (115.02 g, 639.77 mmol) is added to a solution of tert-butyl 2-chlorospiro[4,5-dihydrothieno[2,3-c]pyran-7,4'-piperidine]-1'-carboxylate (200 g, 581.61 mmol) in chlorobenzene (1.60 L) at rt. The resulting suspension is irradiated with 3×100 w bulb lamps situated almost in contact with the external reactor wall and the reactor temperature is set to 45° C. After 4 hr., N-bromosuccinimide (26.14 g, 145.40 mmol) is added and the temperature is maintained at 40° C. for 15 hr. Reaction mixture is cooled to 0° C. and methyl t-butyl ether (500 mL) is added. Solid is filtered and the solution is concentrated to about 1000 mL solution in chlorobenzene. Then, methyl t-butyl ether (1000 mL) is added, solids are filtered and filtrate is concentrated to afford 600 mL of a chlorobenzene solution. Dimethyl sulfoxide (806.47 mL, 11.35 mol) is added and sodium bicarbonate (95.38 g, 1.14 mol) are added at room temperature. After stirring 24 hr. at room temperature, water/ice (1000 mL) is added and the phases are separated. Organic phase is washed with water (2×1 L) and concentrated to afford a solution in chlorobenzene. Then, dichloromethane (1.2 L) is added and the mixture is cooled to 5° C. (ice/water bath). Potassium bromide (20.27 g, 170.31 mmol) and 2,2,6,6-tetramethylpiperidine-N-oxide (4.43 g, 28.38 mmol) are added. Then, a solution of sodium hypochlorite 6% in water (644.40 mL, 567.68 mmol) adjusted at pH=9 with sodium bicarbonate (s) is added to the reaction mixture at 5° C. and the resulting mixture is stirred 1 hr. at 5° C. to room temperature. Water (1 L) is added and the phases are separated. Organic phase is washed with water (2×0.5 L) and was cooled with ice/water bath. Then, Potassium Bromide (2.03 g, 17.03 mmol), 2,2,6,6-tetramethylpiperidine-N-oxide (0.05 g, 0.32 mmoles) and a solution of 6% sodium hypochlorite in water (128.88 mL, 113.54 mmol) adjusted at pH=9 with solid sodium bicarbonate are added to the reaction mixture at 5° C. and the resulting mixture is stirred 1 h from 5° C. to room temperature. Then, water (1 L) is added and the phases are separated. Organic phase is washed with water (2×1 L) dried and concentrated to afford a dark brown solid.

Solid is triturated with hexane (500 mL), methyl t-butyl ether/hexane 5% (250 mL) and methyl t-butyl ether/hexane 10% (250 mL) to obtain tert-butyl 4'-oxo-2'-chloro-4',5'-dihydrospiro[piperidine-4,7'-thieno[2,3-c]pyran]-1-carboxylate as a light brown solid in a 66% yield. MS (m/z): 258 (M+1 (Boc)).

3. tert-Butyl 2'-chloro-4',4'-difluoro-4',5'-dihydrospiro[piperidine-4,7'-thieno[2,3-c]pyran]-1-carboxylate In a 500 mL PFA flask charged with tetrahydrofuran (81 mL) is added (bis(2-methoxyethyl)amino)sulfur trifluoride (183.62 g, 829.94 mmol) and tert-butyl 4'-oxo-2'-chloro-4',5'-dihydrospiro[piperidine-4,7'-thieno[2,3-c]pyran]-1-carboxylate (135 g, 377.24 mmol). The resulting suspension is stirred at 70° C. for 24 h. Then, it is cooled to room temperature and slowly poured over a mixture of ice and saturated aqueous solution of sodium bicarbonate (4 L) with stirring (gas evolution). Methyl t-butyl ether is used to transfer the remaining material from flasks. After gas evolution ceased, solid sodium bicarbonate is added with stirring until pH 8 was reached. The resulting mixture is extracted with methyl t-butyl ether (3×500 mL) until no product was detected by TLC in the aqueous phase. Combined organics are washed with water (3×500 mL) and brine (500 mL), dried over sodium sulfate and concentrated to afford a dark thick oil (250 g). Crude material is dissolved in dichloromethane and filtered through a silica gel plug eluting with methyl t-butyl ether/hexane 10% (6 L) and methyl t-butyl ether/hexane (4 L). Fractions are collected till no product was detected by TLC (20% methyl t-butyl ether/hexane UV, Rf=0.5). Filtrate is concentrated to obtain a light brown solid which is dried under vacuum at 40° C. till constant weight to afford 70% yield of tert-butyl 2'-chloro-4',4'-difluoro-4',5'-dihydrospiro[piperidine-4,7'-thieno[2,3-c]pyran]-1-carboxylate. MS (m/z): 324 (M+1 tBu).

4. 2'-Chloro-4',4'-difluoro-4',5'-dihydrospiro[piperidine-4,7'-thieno[2,3-c]pyran]

37% Hydrochloric acid (74.12 mL, 789.78 mmol) is added to a solution of tert-butyl 2'-chloro-4',4'-difluoro-4',5'-dihydrospiro[piperidine-4,7'-thieno[2,3-c]pyran]-1-carboxylate (60 g, 157.96 mmol) in isopropyl alcohol (420 mL) at 45° C. The resulting solution is stirred at 45° C. for 15 h. Then, the mixture is concentrated to 1/4 volume to afford a white suspension. Water (100 mL) is added and the suspension is basified with 6N aqueous solution of sodium hydroxide to obtain a two-layer mixture that is extracted with methyl t-butyl ether (3×100 mL). Combined organics are washed with brine (50 mL), dried over sodium sulfate and concentrated to afford a light brown solid which is dried under vacuum till constant weigh to yield 97% of the title compound. MS (m/z): 280 (M+1).

Preparation 6: 2,4,4-Trifluorospiro[5H-thieno[2,3-c]pyran-7,4'-piperidine]

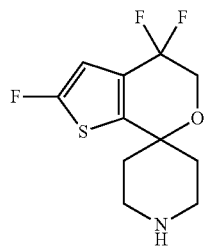

1. tert-Butyl 2-bromo-4-hydroxy-spiro[4,5-dihydrothieno[2,3-c]pyran-7,4'-piperidine]-1'-carboxylate N-bromosuccinimide (2.2 equiv) is added to a solution of tert-butyl spiro[4,5-dihydrothieno[2,3-c]pyran-7,4'-piperidine]-1'-carboxylate (13.5 g) in chlorobenzene (108 mL). The resulting suspension is irradiated with 260 w bulb lamp overnight. More N-bromosuccinimide (1.7 g) is added to the mixture and the mixture is irradiated with 260 w bulb lamp for 3 hours. The solvent is eliminated under reduced pressure giving a residue that is dissolved in acetone (650 mL) and a solution of silver nitrate (8.8 g) in water (650 mL) is added. The mixture is stirred at room temperature in darkness overnight. The mixture is filtered off and the acetone is evaporated. Ethyl acetate is added and the organic layer is washed with saturated aqueous solution of sodium bicarbonate and brine. The organic layer is dried over sodium sulfate, filtered and the solvent is evaporated under reduced pressure. The residue is purified by normal phase Isco chromatography (eluent: hexane/ethyl acetate 15-60%) to afford tert-butyl-2-bromo-4-hydroxy-spiro[4,5-dihydrothieno[2,3-c]pyran-7,4'-piperidine]-1'-carboxylate in a 38% yield. MS (m/z): 426/428 (M+23/M+2+23)

2. tert-Butyl 2'-bromo-4'-oxo-spiro[piperidine-4,7'-thieno[2,3-c]pyran]-1-carboxylate Potassium bromide (535.67 mg, 4.50 mmol) is added to a solution of tert-butyl 2-bromo-4-hydroxy-spiro[4,5-dihydrothieno[2,3-c]pyran-7,4'-cyclohexane]-1'-carboxylate (7.28 g) and 2,2,6,6-tetramethylpiperidine-N-oxide (281.33 mg, 1.80 mmol,) in dichloromethane (70 mL) at 0° C. In another vessel sodium bicarbonate is added to 10% in water sodium hypochlorite (22.34 mL, 36.01 mmol) until pH 9. This sodium hypochlorite-sodium bicarbonate solution is added dropwise at 0° C. and the resulting dark suspension is stirred at 0° C. for 15 min. dichloromethane (20 mL) and water (20 mL) are added and the phases are separated. The organic phase is washed with water (20 mL) and dried over sodium sulfate. The solvent is eliminated under reduced pressure to afford tert-butyl 2'-bromo-4'-oxo-spiro[piperidine-4,7'-thieno[2,3-c]pyran]-1-carboxylate in a 99% yield. MS (m/z): 346/348 (M+1 tBu/M+3-tBu)

3. tert-Butyl 2-bromo-4,4-difluoro-spiro[5H-thieno[2,3-c]pyran]-7,4'-piperidine]-1'-carboxylate In a 100 mL perfluoroalcoxy-flask flask is added (bis(2-methoxyethyl)amino)sulfur trifluoride (5.16 mL, 27.96 mmol) to dry tetrahydrofuran (3.5 mL). Then tert-butyl 2'-bromo-4'-oxo-spiro[piperidine-4,7'-thieno[2,3-c]pyran]-1-carboxylate (4.5 g, 11.19 mmol) is added. The solution is stirred at 70° C. overnight. After that time, methyl t-butyl ether is added (30 mL), and the reaction mixture is cautiously poured over sodium bicarbonate (saturated aqueous solution) cooled in an ice bath. CO2 evolution is seen and sodium bicarbonate (saturated aqueous solution) is added until pH 8. The mixture is extracted with methyl t-butyl ether. Organic layer is decanted, washed with brine (2×), dried over magnesium sulfate and the solvent evaporated under reduced pressure. The crude is purified by normal phase Isco chromatography eluting with methyl t-butyl ether/hexane to yield 3.2 g of tert-butyl 2-bromo-4,4-difluoro-spiro[5H-thieno[2,3-c]pyran-7,4'-piperidine]-1'-carboxylate. MS (m/z): 368/370 (M+1-tBu/M+3-tBu).

4. tert-Butyl 2,4,4-trifluorospiro[5H-thieno[2,3-c]pyran-7,4'-piperidine]-1'-carboxylate 2.5 M butyl lithium in hexane (47 mL) is added over a solution of tert-butyl 2-bromo-4,4-difluoro-spiro[5H-thieno[2,3-c]pyran-7,4'-piperidine]-1'-carboxylate (1.99 g, 4.69 mmol) in tetrahydrofuran (50 mL) under nitrogen and at −78° C. The mixture is stirred at −78° C. for 1 hour and solid N-fluoro-benzenesulfonimide (3.69 g, 11.73 mmol) is added. The mixture is allowed to warm to room temperature and stirred at room temperature overnight. Saturated aqueous solution of ammonium chloride is added and the organic phase is extracted with ethyl acetate, dried over sodium sulfate and the solvent eliminated under reduced pressure. The crude material is purified by normal phase Isco chromatography (hexane/ethyl acetate 3-12%) to yield 1.3 g of tert-butyl 2,4,4-trifluorospiro[5H-thieno[2,3-c]pyran-7,4'-piperidine]-1'-carboxylate that is further purified by HPLC to obtain 0.818 g of that compound. MS (m/z): 308 (M+1-tBu).

5. 2,4,4-Trifluorospiro[5H-thieno[2,3-c]pyran-7,4'-piperidine]

t-Butyl 2,4,4-trifluorospiro[5H-thieno[2,3-c]pyran-7,4'-piperidine]-1'-carboxylate (2.00 g, 5.50 mmol) is dissolved in hydrochloric acid (4N in dioxane) (10 mL, 40 mmol). The mixture is stirred at room temperature for 1 h and then passed through a 50 g SCX cartridge (solid cation exchange) to yield 1.3 g of the title compound after evaporation of 2 N ammonia in methanol fraction. MS (m/z): 264 (M+1).

Preparation 7: 2-Chloro-4,4-difluoro-1'-[(3-methyl-1H-pyrazol-4-yl)methyl]spiro[5H-thieno[2,3-c]pyran-7,4'-piperidine]

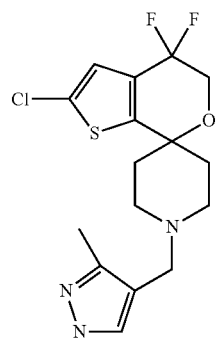

To a solution of 2-chloro-4,4-difluoro-spiro[5H-thieno[2,3-c]pyran-7,4'-piperidine (105 g, 375 mmol) in tetrahydrofuran (1.58 L) is added 3-methyl-1H-pyrazole-4-carbaldehyde (43.40 g, 394.12 mmol) and the mixture is stirred at room temperature for 1 hr. Then, powdered sodium triacetoxyborohydride (95.46 g, 450.42 mmol) is added in 3 portions. The mixture is stirred at room temperature for 15 h. Then, the reaction mixture is poured over an ice-sodium bicarbonate saturated aqueous solution (400 mL). Phases are separated. Aqueous phase is extracted with ethyl acetate (100 mL). Combined organic layers are washed with 50% brine and a solid precipitates in the organic phase. Organic phase is concentrated to give 170 g of the title compound. MS (m/z): 374 (M+1).

The compounds of Preparation 8-11 are prepared essentially as described in Preparation 7 using 1,2-dichloroethane as solvent.

| Prep. No. | Chemical name | Structure | Yield (%) | Physical data: MS (m/z) |
|---|---|---|---|---|
| 8 | 2-Fluoro-1'-[(3-methyl-1H-pyrazol-4-yl)methyl]spiro[4,5-dihydrothieno[2,3-c]pyran-7,4'-piperidine] | 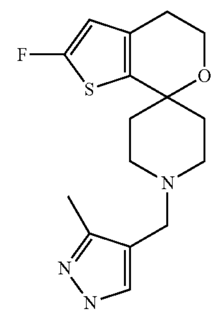 | 93 | 322 (M + 1) |
| 9 | 2-Chloro-1'-[(3-methyl-1H-pyrazol-4-yl)methyl]spiro[4,5-dihydrothieno[2,3-c]pyran-7,4'-piperidine] | 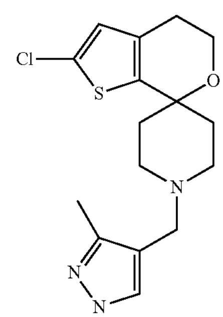 | 99 | 338 (M + 1) |
| 10 | 2,4,4-Trifluoro-1'-[(3-methyl-1H-pyrazol-4-yl)methyl]spiro[5H-thieno[2,3-c]pyran-7,4'-piperidine] | 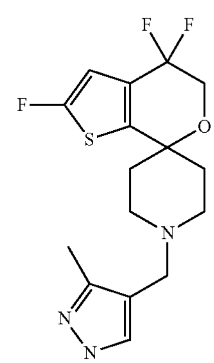 | 99 | 358 (M + 1) |
| 11 | 2-Chloro-1'-(1H-pyrazol-4-ylmethyl)spiro[4,5-dihydrothieno[2,3-c]pyran-7,4'-piperidine] | 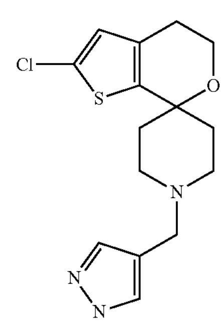 | 99 | 324 (M + 1) |

Preparation 12: 2-[4-[(2-Chloro-4,4-difluoro-spiro [5H-thieno[2,3-c]pyran-7,4'-piperidine]-1'-yl)methyl]-3-methyl-pyrazol-1-yl]pyridine-3-carbaldehyde

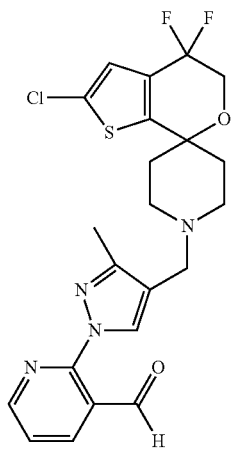

To a 250 mL flask are added copper(I) iodide (1.91 g, 10.03 mmol), 2-chloro-4,4-difluoro-1'-[(3-methyl-1H-pyrazol-4-yl)methyl]spiro[5H-thieno[2,3-c]pyran-7,4'-piperidine] (25 g, 66.87 mmol), potassium carbonate (19.60 g, 140.43 mmol), toluene (50 mL) and a stirring bar. The reaction mixture is degassed by 5 vacuum/refill cycles. Then, 2-bromo-3-formyl pyridine (18.66 g, 100.31 mmol) and trans-N,N'-dimethylcyclohexane-1,2-diamine (3.16 mL, 20.06 mmol) are added. The reaction is stirred at room temperature for 5 minutes. Then, it is immersed in a preheated oil bath at 115° C. and stirred for 15 h at that temperature. Reaction mixture is cooled to room temperature, diluted with 300 mL of ethyl acetate and filtered through celite. It is washed with ethyl acetate (100 mL) and aqueous solution of ammonium hydroxide (3%) (4×100 mL) to remove copper traces, and then, it is washed with water (50 mL) and brine (50 mL). Solution is dried over sodium sulfate. The solvent is evaporated in vacuo to give a tan solid. Solid was filtered through a pad of silica gel using as eluent 2-propanol/dichloromethane (3% to 5% of 2-propanol) to give the title compound in 69% yield. MS (m/z): 479 (M+1).

Preparation 13: 2-[4-[(2-Fluorospiro[4,5-dihydrothieno[2,3-c]pyran-7,4'-piperidine]-1'-yl)methyl]-3-methyl-pyrazol-1-yl]pyridine-3-carbaldehyde

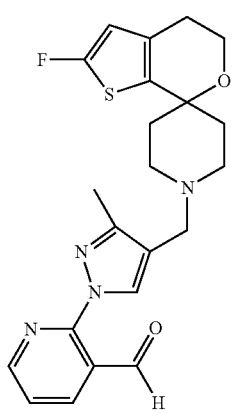

The compound of Preparation 13 is essentially prepared as described in Preparation 12 by using 2-bromopyridine-3-carbaldehyde and 2-fluoro-1'-[(3-methyl-1H-pyrazol-4-yl)methyl]spiro[4,5-dihydrothieno[2,3-c]pyran-7,4'-piperidine]. Residue is purified by normal phase Isco chromatography to yield 83% of the title compound. MS (m/z): 427 (M+1).

Preparation 14: N-[(2-Chloro-3-pyridyl)methyl]acetamide

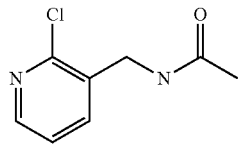

To a solution of (2-chloro-3-pyridyl)methanamine (300 mg, 2.10 mmol) in dichloromethane (2 mL) at room temperature is added acetic acid anhydride (198.88 mL, 2.10 mmol) and triethylamine (293.26 mL, 2.10 mmol). After 1 h the reaction is quenched with saturated aqueous solution of sodium bicarbonate and extracted with dichloromethane. The organic layer was separated, dried over magnesium sulfate and the solvent evaporated in vacuo to afford 184 mg of N-[(2-chloro-3-pyridyl)methyl]acetamide. MS (m/z): 185 (M+1)

Preparation 15: (2-Bromo-3-pyridyl)methyl methanesulfonate

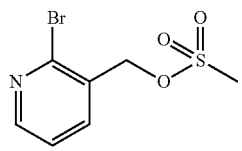

1. (2-Bromo-3-pyridyl)methanol

To a 2 L round bottom flask (fitted with stir bar, under nitrogen and at 0° C.) containing 2-bromo-3-pyridine-carboxaldehyde (22.15 g, 119.08 mmol) and methanol (200 mL), is added sodium borohydride (1.35 g, 35.72 mmol) in three portions. After 1 h at 0° C. water (200 mL) is added and the reaction is concentrated under reduced pressure to remove the methanol. The resulting residue is dissolved in ethyl acetate and washed with water (200 mL). The organic extraction is washed with brine, dried over magnesium sulfate, filtered and concentrated to afford 22 g of (2-bromo-3-pyridyl)methanol as a white solid. MS (m/z): 188 (M+1), 190 (M+3).

2. (2-Bromo-3-pyridyl)methyl methanesulfonate

Triethylamine (8.90 mL) is added to a round bottom flask containing a solution of (2-bromopyridin-3-yl)methanol (8 g, 42.55 mmol) in dichloromethane (212 mL) at 0° C., then methanesulfonyl chloride (3.95 mL) is added and the mixture is stirred at that temperature for 1.5 h. After that time the mixture is washed with water and organic layer is decanted, Preparation 16: 2-(2-Bromo-3-pyridyl)propan-2-ol

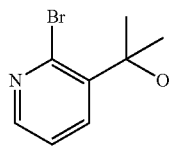

Lithium diisopropylamide (2M, 12.5 mL, 25 mmol) is dissolved in tetrahydrofuran (40 mL) and cooled to −78° C. 2-Bromopyridine (3.9 g, 25 mmol) is added dropwise and the reaction is stirred for 3 hr. before adding acetone (1 mL, dried over freshly activated molecular sieves) and allowing warming to room temperature. The reaction is quenched with saturated ammonium chloride and extracted with ethyl acetate. The organic layer is dried over magnesium sulfate and evaporated. The residue is purified by flash column chromatography on silica, eluting with 20% hexane/tert-butyl methyl ether to give the title compound (1.4 g, 26%). $^1$H-NMR (d$^6$-dimethyl sulfoxide): 8.23 (dd, J=1.9, 4.5 Hz, 1H), 8.19 (dd, J=2.0, 7.8 Hz, 1H), 7.44 (dd, J=4.5, 7.7 Hz, 1H), 5.43 (s, 1H), 2.12 (s, 1H), 1.46 (s, 6H).

Preparation 17: Ethyl 3-methyl-1H-pyrazole-4-carboxylate

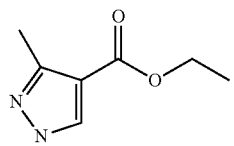

Sulfuric acid (18 mL, 337.69 mmol) is added to a suspension of 1H-pyrazole-4-carboxylic acid, 3-methyl-(10 g, 79.29 mmol) in ethanol (90 mL) and the mixture is stirred at 85° C. for 20 h. After that time, solvent is partially removed. Residue is basified with 1M sodium hydroxide solution to pH 6-7 and extracted with dichloromethane. Organic layer is decanted, dried over magnesium sulfate and solvent evaporated under reduced pressure to yield 10.3 g of the title compound that is used with no further purification. MS (m/z): 155 (M+1).

Preparation 18: Methyl 2-fluoropyridine-3-carboxylate

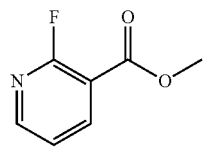

2 M lithium diisopropyl amide (11.3 mL, 22.5 mmol) is slowly added over a solution of 2-fluoropyridine (2 g, 20.5 mmol) in tetrahydrofuran (90 mL) under nitrogen atmosphere at −78° C. After 4 h at that temperature methyl chloroformate (1.9 mL, 24.6 mmol) is added and the mixture is stirred for an additional hour at −78° C. and allowed to reach room temperature overnight. Reaction mixture is slowly poured over water and extracted in diethyl ether. Organic layer is washed with brine, dried over sodium sulfate and solvent is evaporated in vacuo. Residue is purified by normal phase Isco chromatography eluting with hexane/diethyl ether (9/1) to give 495.2 mg of the title compound. MS (m/z): 156 (M+1).

Preparation 19: 1-(3-Fluoro-2-pyridyl)-3-methyl-pyrazole-4-carbaldehyde

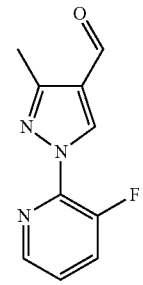

Potassium t-Butyl alcohol (29.25 g, 260.68 mmol) is added to a solution of 3-methyl-1H-pyrazole-4-carbaldehyde (26.00 g, 236.12 mmol) in dimethylformamide (250 mL) cooled with an aqueous bath. The mixture is stirred at room temperature for 10 min. Then, 2,3-difluoropyridine (25 g, 217.24 mmol) is added and the mixture is stirred at room temperature for 20 hr. The mixture is poured over an ice/water mixture and extracted in ethyl acetate (3×20 mL). Organics are dried over magnesium sulfate and solvent evaporated in vacuo. The residue is purified by silica gel chromatography using as eluent hexane/isopropyl alcohol to afford a crude material with residual dimethylformamide. The material is then dissolved in ethyl acetate (100 mL) and washed with water (3×20 mL). Aqueous phase is extracted with ethyl acetate (2×20 mL). Combined organics are dried over sodium sulfate and concentrated to give 19 g of the title compound. MS (m/z): 206 (M+1).

Preparation 20: 2-(4-Formyl-3-methyl-pyrazol-1-yl) pyridine-3-carbonitrile

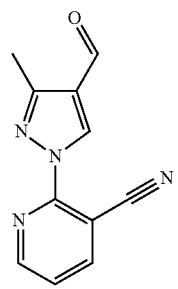

The compound of Preparation 20 is essentially prepared as described in Preparation 19 by using 3-methyl-1H-pyrazole- 4-carbaldehyde and 2-fluoropyridine-3-carbonitrile. The title compound is obtained with a yield of 23%. MS (m/z): 213 (M+1).

Preparation 21: Methyl 2-(4-formyl-3-methyl-pyrazol-1-yl)pyridine-3-carboxylate

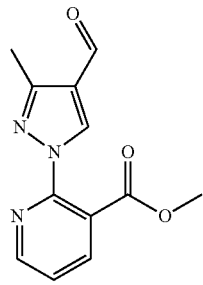

A mixture of 3-methyl-1H-pyrazole-4-carbaldehyde (300 mg, 2.72 mmol), potassium carbonate (565 mg, 4.08 mmol), methyl 2-fluoropyridine-3-carboxylate (507 mg, 3.27 mmol) and dimethylformamide (2 mL) is stirred at 60° C. for 16 h. Water is added and the compound is extracted in ethyl acetate. The organic layer is washed with brine, dried over sodium sulfate and solvent is evaporated. The crude mixture is purified by normal phase Isco chromatography using hexane: ethyl acetate, 2:1 as eluent to yield 422 mg of the title compound. MS (m/z): 246 (M+1).

The compound of Preparation 22-23 may be essentially prepared as described in Preparation 21 using the corresponding 2-chloro pyridyl reagent.

Preparation 24: 1-[3-(Dimethylaminomethyl)-2-pyridyl]-3-methyl-pyrazole-4-carbaldehyde

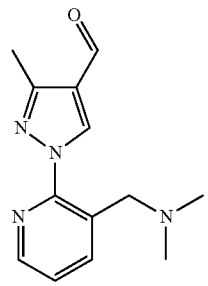

1. Ethyl 1-[3-(dimethylaminomethyl)-2-pyridyl]-3-methyl-pyrazole-4-carboxylate

This compound is prepared essentially as described in Preparation 7 by using ethyl 1-(3-formyl-2-pyridyl)-3-methyl-pyrazole-4-carboxylate and dimethylamine in a 95% yield and is used with no further purification after workup. MS (m/z): 289 (M+1)

2. 2. [1-[3-(Dimethylaminomethyl)-2-pyridyl]-3-methyl-pyrazol-4-yl]methanol

To a solution of ethyl 1-[3-(dimethylaminomethyl)-2-pyridyl]-3-methyl-pyrazole-4-carboxylate (217.7 g, 0.75 mmol) in tetrahydrofuran (5 mL) cooled to 0° C. and under nitrogen, 1 M lithium aluminum hydride in tetrahydrofuran (0.9 mL, 0.9 mmol) is added and the mixture is stirred at that temperature for 5 minutes. The reaction is quenched with

| Prep. No. | Chemical name | Structure | Yield (%) | Physical data: MS (m/z) |
|---|---|---|---|---|
| 22 | N-[[2-(4-Formyl-3-methyl-pyrazol-1-yl)-3-pyridyl]methyl]acetamide | 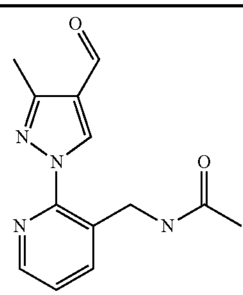 | 56 | 259 (M + 1) |
| 23 | Ethyl 1-(3-formyl-2-pyridyl)-3-methyl-pyrazole-4-carboxylate | | 52 | 260 (M + 1) | saturated aqueous solution of ammonium chloride and the crude is extracted with ethyl acetate. The organic layer is separated, dried on sodium sulfate and the solvent is evaporated in vacuo. In this particular example the compound is not isolated in the organic extraction and is finally separated from the aqueous solution with an SCX cartridge to afford 146 mg (78%) of [1-[3-(dimethylaminomethyl)-2-pyridyl]-3-methyl-pyrazol-4-yl]methanol that is used with no further purification. MS (m/z): 247 (M+1).

3. 1-[3-(Dimethylaminomethyl)-2-pyridyl]-3-methyl-pyrazole-4-carbaldehyde 3,3,3-Triacetoxy-3-iodophthalide (0.553 g, 1.3 mmol) is added to a solution of [1-[3-(dimethylaminomethyl)-2-pyridyl]-3-methyl-pyrazol-4-yl]methanol (0.146 g, 0.59 mmol) in dichloromethane (4 mL) at room temperature. After one hour the reaction is quenched by addition of 2N sodium carbonate solution and the compound is extracted in dichloromethane. The organic layer is separated, dried over magnesium sulfate and the solvent evaporated in vacuo to afford 126 mg of 1-[3-(dimethylaminomethyl)-2-pyridyl]-3-methyl-pyrazole-4-carbaldehyde that is used with no further purification. MS (m/z): 245 (M+1).

Preparation 25: 1-(3-Fluoro-2-pyridyl)-3-(isopropoxymethyl)pyrazole-4-carbaldehyde

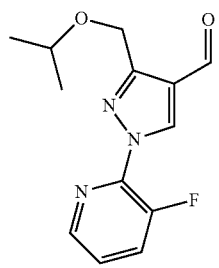

1. Ethyl 3-(bromomethyl)-1-(3-fluoro-2-pyridyl)pyrazole-4-carboxylate

To a solution of ethyl 1-(3-fluoro-2-pyridyl)-3-methyl-pyrazole-4-carboxylate (10.2 g, 40.9 mmol) in chlorobenzene (205 mL), N-bromosuccinimide (8 g) is added at room temperature. The reaction mixture is stirred and irradiated under a 100 W lamp at room temperature overnight. Then more N-bromosuccinimide (2 g) is added and after 2 hr., no starting material is detected. Solids are filtered and solvent is evaporated. The crude is purified by normal phase Isco chromatography using as eluent dichloromethane and methanol to give 5.3 g of ethyl 3-(bromomethyl)-1-(3-fluoro-2-pyridyl)pyrazole-4-carboxylate. MS (m/z): 328; 330 (M+1; M+3).

2. Isopropyl 1-(3-fluoro-2-pyridyl)-3-(isopropoxymethyl)pyrazole-4-carboxylate To a solution of ethyl 3-(bromomethyl)-1-(3-fluoro-2-pyridyl)pyrazole-4-carboxylate (1.5 g, 4.57 mmol), in propan-2-ol (23 mL), lithium isopropoxide (3.02 g) is added and the mixture is stirred overnight at room temperature. After that time more lithium isopropoxide (4.5 g) is added in three portions of 1.5 g each every 16 hours. After the last addition, the reaction mixture is finally stirred at 40° C. for 16 hours. Solvent is evaporated and the residue dissolved in ethyl acetate and washed with brine. Organic layer is decanted and dried over sodium sulfate. Solvent is evaporated and the residue is purified by normal phase Isco chromatography using as eluent dichloromethane and methanol to give 317 mg of isopropyl 1-(3-fluoro-2-pyridyl)-3-(isopropoxymethyl)pyrazole-4-carboxylate. MS (m/z): 322 (M+1).

3. [1-(3-Fluoro-2-pyridyl)-3-(isopropoxymethyl)pyrazol-4-yl]methanol

To a solution of isopropyl 1-(3-fluoro-2-pyridyl)-3-(isopropoxymethyl)pyrazole-4-carboxylate (316 mg, 0.98 mmol) in diethyl ether (4.9 mL) under nitrogen and cooled to 0° C., 1M lithium aluminium hydride in tetrahydrofuran (1.2 mL) is added. The mixture is stirred at 0° C. for 1 hour. Water (46 µL) is added and stirred for 5 min, then 15% aqueous solution of NaOH (46 µL) and water (138 µL) are successively added. Solids are filtered and solvent evaporated to obtain 241 mg of [1-(3-fluoro-2-pyridyl)-3-(isopropoxymethyl)pyrazol-4-yl]methanol that is used without further purification. MS (m/z): 266 (M+1).

4. 1-(3-Fluoro-2-pyridyl)-3-(isopropoxymethyl)pyrazole-4-carbaldehyde

A mixture of [1-(3-fluoro-2-pyridyl)-3-(isopropoxymethyl)pyrazol-4-yl]methanol (241 mg; 0.91 mmol) and manganese(IV) oxide (791 mg) are stirred in dichloromethane (5 mL) at room temperature overnight. After that time, the reaction mixture is filtered over celite and solvent evaporated to obtain 197 mg of the title compound that is used without further purification. MS (m/z): 264 (M+1).

Preparation 26: 1-(3-Fluoro-2-pyridyl)-3-(methoxymethyl)pyrazole-4-carbaldehyde

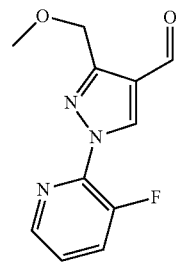

1. Ethyl 1-(3-fluoro-2-pyridyl)-3-(methoxymethyl)pyrazole-4-carboxylate

To a solution of 3-bromomethyl-1-(3-fluoro-pyridin-2-yl)-1H-pyrazole-4-carboxylic acid ethyl ester (1.13 g, 3.44 mmol) in acetone (23 mL), potassium iodide (200.1 mg), potassium carbonate (865.33 mg) and methanol (4.18 mL) are added. The mixture is stirred at room temperature for 48 hours. Methyl and ethyl ester of the desired compound are detected. Solvents are evaporated. Residue is diluted with dichloromethane and washed with water. Organic layer is decanted, dried over magnesium sulfate and solvent evaporated. Crude is purified by normal phase Isco chromatography using as eluent ethyl acetate and hexane to yield 599 mg of a mixture of both methyl and ethyl esters. MS (m/z): 266 (M+1) and 280 (M+1).

2. [1-(3-Fluoro-2-pyridyl)-3-(methoxymethyl)pyrazol-4-yl]methanol

This compound is essentially prepared as described in the step 3 of preparation 25 (reduction step) in a 93% yield and using as starting material ethyl 1-(3-fluoro-2-pyridyl)-3-(methoxymethyl)pyrazole-4-carboxylate (in a mixture containing also the methyl ester). [1-(3-Fluoro-2-pyridyl)-3-(methoxymethyl)pyrazol-4-yl]methanol is used without further purification. MS (m/z): 238 (M+1).

3. 1-(3-Fluoro-2-pyridyl)-3-(methoxymethyl)pyrazole-4-carbaldehyde

This compound is essentially prepared as described in step 4 of preparation 25 (oxidation step) in a 91% yield and using as starting material [1-(3-fluoro-pyridin-2-yl)-3-methoxymethyl-1H-pyrazol-4-yl]-methanol. The title compound is used without further purification. MS (m/z): 236 (M+1).

Preparation 27: 3-Methyl-1-(3-morpholino-2-pyridyl)pyrazole-4-carbaldehyde

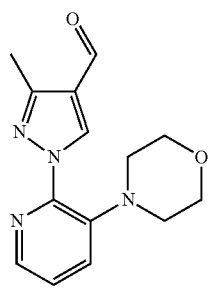

A mixture of 1-(3-fluoro-2-pyridyl)-3-methyl-pyrazole-4-carbaldehyde (230 mg, 1.12 mmol) and morpholine (2 mL, 22.93 mmol) is heated under microwave irradiation (temperature 160° C., ramp time: 2 min, hold time: 10 min, potency: 250 W). The excess of morpholine is eliminated in vacuo and the residue is diluted in dichloromethane and washed in saturated aqueous solution of sodium bicarbonate. The organic layer is separated, dried over magnesium sulfate and the solvent evaporated in vacuo. The residue is purified by normal phase Isco chromatography using hexane/ethyl acetate as eluent (from 50 to 100% in ethyl acetate) to yield 72% of the title compound. MS (m/z): 273 (M+1).

Preparation 28: 2-Bromo-3-(methoxymethyl)pyridine

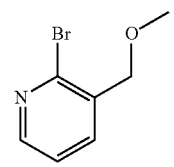

To a solution of (2-bromopyridin-3-yl)methanol (20 g, 106.37 mmoles) in 140 mL of tetrahydrofuran is added 60% sodium hydride in mineral oil (6.38 g, 155.5 mmol) at 0° C. under nitrogen atmosphere. Solution is stirred at 0° C. for 30 minutes. Methyl iodide (7.95 mL, 127.6 mmol) is added over the solution and the mixture is stirred at room temperature overnight. The mixture is quenched by addition of water and the crude is extracted with ethyl acetate. The organic layer is separated, dried over magnesium sulfate and solvent evaporated in vacuo to afford 2-bromo-3-(methoxymethyl)pyridin in a 98% yield that is used with no further purification. MS (m/z): 202 (M+1), 204 (M+3).

The compounds from Preparation 29-30 are prepared essentially as described in Preparation 28 using the corresponding alkyl iodide reagents.

| Prep. No. | Chemical name | Structure | Yield (%) | Physical data: MS (m/z) |
|---|---|---|---|---|
| 29 | 2-Bromo-3-(ethoxymethyl)pyridine | 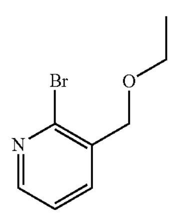 | 99 | 216, 218 (M + 1, M + 3) |
| 30 | 2-Bromo-3-(cyclopropylmethoxymethyl)pyridine | 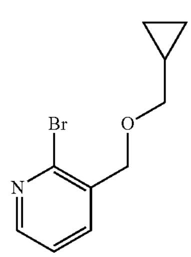 | 100 | 242, 244 (M + 1, M + 3) |

Preparation 31: 2-Bromo-3-(isopropoxymethyl)-pyridine

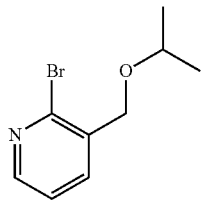

1. 2-Bromo-3-(bromomethyl)-pyridine

A 25 mL Schlenk flask is charged with 2-bromo-3-pyridine benzyl alcohol (1 g, 5.32 mmol) and dichloromethane (15 mL). The resulting solution was cooled to 0° C. in a salt-water/ice bath with vigorous magnetical stirring. Then phosphorus tribromide (0.55 mL, 5.80 mmol) is added dropwise to control the exotherm to below 10° C. A thick slurry resulted and after the addition, the bath is removed and the slurry warmed to room temperature. Then mixture is gradually heated to reflux for 3 h and then to room temperature overnight.

Over the mixture previously cooled at 0° C., ice-water is added and then pH adjusted to basic adding 2 M solution of sodium carbonate. The organic layer is separated and the aqueous solution is washed twice with dichloromethane (2×10 mL). All the organics are combined, dried over magnesium sulfate, filtered and the solvent evaporated under reduced pressure to yield 1.2 g of 2-bromo-3-bromomethyl-pyridine that is used with no further purification.

2. 2-Bromo-3-(isopropoxymethyl)-pyridine

To a solution of isopropyl alcohol (7.31 mL, 95.65 mmol) in dimethylformamide (50 mL) at 0° C. is added sodium hydride (3.63 g, 90.87 mmol) and the mixture is stirred at room temperature for 30 minutes (this reaction is run using a shield as special protection). Then, 2-bromo-3-bromomethyl-pyridine (6 g, 23.91 mmol) in 10 mL of dimethylformamide is added via syringe and the mixture is stirred at room temperature for 1 h. Water is added and the mixture is extracted with ethyl acetate, washed with brine and water, dried over magnesium sulfate, filtered and the solvent evaporated under reduced pressure. The crude material is purified by normal phase Isco chromatography using ethyl acetate and hexane as eluent (gradient of 5 to 25% of ethyl acetate) to yield 3.67 g of the title compound. MS (m/z): 230, 232 (M+1, M+3)

Preparation 32: 2-(2-Bromo-3-pyridyl)acetonitrile

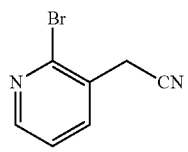

A mixture of 2-bromo-3-bromomethyl-pyridine (840 mg, 3.35 mmol) and sodium cyanide (187.99 mg, 3.68 mmol) is stirred and refluxed for 1 h in a mixture water (10 mL)-ethanol (2 mL). The reaction mixture is diluted with dichloromethane and washed with saturated aqueous solution of sodium bicarbonate. The organic layer is separated, dried over magnesium sulfate and the solvent evaporated in vacuo to give 83% of the title compound that is used without further purification. MS (m/z): 197 (M+1), 199 (M+3).

Preparation 33: 1-[3-(Cyclopropoxymethyl)-2-pyridyl]-3-methyl-pyrazole-4-carbaldehyde

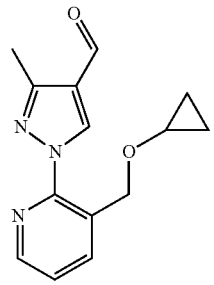

1. Ethyl 1-[3-(hydroxymethyl)-2-pyridyl]-3-methyl-pyrazole-4-carboxylate

To a solution of 1-(3-formyl-pyridin-2-yl)-3-methyl-1H-pyrazole-4-carboxylic acid ethyl ester (1 g, 3.9 mmol) in methanol (25 mL), sodium borohydrate (220.2 mg, 5.8 mmol) is added. The mixture is stirred at room temperature for 2 hr. The solvent is eliminated and the crude is dissolved in ethyl acetate and washed with saturated aqueous solution of ammonium chloride. The organic layer is separated, dried over sodium sulfate, filtered and the solvent evaporated under reduced pressure to give 1 g of ethyl 1-[3-(hydroxymethyl)-2-pyridyl]-3-methyl-pyrazole-4-carboxylate. MS (m/z): 262 (M+1)

2. Ethyl 3-methyl-1-[3-(vinyloxymethyl)-2-pyridyl]pyrazole-4-carboxylate

Palladium(II)trifluoroacetate (5.1 mg, 15.3 mmoles) and 4,7-diphenyl-phenanthroline (5.1 mg, 15.3 mmoles) are dissolved in n-butyl vinyl ether (6.1 mL, 61.2 mmol) and 1-(3-hydroxymethyl-pyridin-2-yl)-3-methyl-1H-pyrazole-4-carboxylic acid ethyl ester (800 mg, 3.1 mmol) and a few drops of triethylamine are added. The flask is sealed and stirred at 75° C. for 24 hours. Then the mixture is cooled to 24° C. and filtrated through a pad of celite. The solvent is eliminated under reduced pressure and the residue is purified by normal phase Isco chromatography using hexane and ethyl acetate as eluents (5-20% in ethyl acetate) to give 605 mg of ethyl 3-methyl-1-[3-(vinyloxymethyl)-2-pyridyl]pyrazole-4-carboxylate. MS (m/z): 288 (M+1)

3. Ethyl 1-[3-(cyclopropoxymethyl)-2-pyridyl]-3-methyl-pyrazole-4-carboxylate 1.0 M diethylzinc in hexane (365.7 mL, 3.5 mmol) is added under nitrogen to dichloromethane (0.9 mL). The solution is cooled to 0° C. and a solution of trifluoroacetic acid (268.4 µL, 3.5 mmol) in dichloromethane (0.9 mL) is added very slowly. After 20 min a solution of diiodomethane (286.1 mL, 3.5 mmol) in dichloromethane (0.9 mL) is added. After an additional 20 min, a solution of 3-methyl-1-(3-vinyloxymethyl-pyridin-2-yl)-1H-pyrazole-4-carboxylic acid ethyl ester (510 mg, 1.8 mmol) in dichloromethane (0.9 mL) is added. The mixture is stirred at room temperature overnight. 5% HCl is added and the aqueous layer is extracted with ethyl acetate. The organic layer is separated, dried over sodium sulfate and the solvent is eliminated under reduced pressure. The crude is purified by normal phase Isco chromatography using hexane and ethyl acetate as eluents (5-20% in ethyl acetate) to get 310 mg of ethyl 1-[3-(cyclopropoxymethyl)-2-pyridyl]-3-methyl-pyrazole-4-carboxylate. MS (m/z): 302 (M+1)

4. 1-[3-(Cyclopropoxymethyl)-2-pyridyl]-3-methyl-pyrazole-4-carbaldehyde

To a solution of 1-(3-cyclopropoxymethyl-pyridin-2-yl)-3-methyl-1H-pyrazole-4-carboxylic acid ethyl ester (410 mg, 1.03 mmol) in tetrahydrofuran (0.15 M) at 0° C. under nitrogen, 1.0 M lithium aluminum hydride in tetrahydrofuran (1.2 equiv) is added. The mixture is stirred at room temperature for 1 h and saturated aqueous solution of ammonium chloride is added and the aqueous layer is extracted with ethyl acetate. The organic layer is separated, dried over sodium sulfate and the solvent eliminated under reduced pressure. The crude material is dissolved in dichloromethane (14 mL) and manganese (IV) oxide (1.2 g, 13.9 mmol) is added. The mixture is stirred at room temperature overnight and then filtered through a pad of celite and the solvent is evaporated under reduced pressure. The crude is passed through a pad of silica gel (eluent: ethyl acetate and dichloromethane). The solvent is eliminated under reduced pressure to yield 90 mg of the title product. MS (m/z): 258 (M+1).

Preparation 34: 1-[3-(Methoxymethyl)-2-pyridyl]-3-methyl-pyrazole-4-carbaldehyde

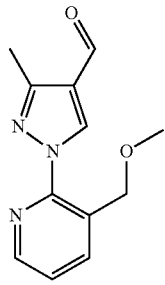

1. Ethyl 1-[3-(methoxymethyl)-2-pyridyl]-3-methyl-pyrazole-4-carboxylate

This compound is prepared essentially as described in Preparation 12 by using ethyl 3-methyl-1H-pyrazole-4-carboxylate and 2-bromo-3-(methoxymethyl)pyridine in a 83% yield. MS (m/z): 276 (M+1).

2. [1-[3-(Methoxymethyl)-2-pyridyl]-3-methyl-pyrazol-4-yl]-methanol

This compound is prepared essentially as described in Preparation 24 (step 2) by using ethyl 1-[3-(methoxymethyl)-2-pyridyl]-3-methyl-pyrazole-4-carboxylate in a 88% yield. MS (m/z): 234 (M+1).

3. 1-[3-(Methoxymethyl)-2-pyridyl]-3-methyl-pyrazole-4-carbaldehyde

A mixture of A mixture of [1-[3-(methoxymethyl)-2-pyridyl]-3-methyl-pyrazol-4-yl]methanol (2.2 g, 9.4 mmol) and manganese (IV) oxide (19 g, 188.8 mmol) is stirred in dichloromethane (20 mL) at room temperature overnight. The reaction mixture is filtered over celite and the solvent evaporated under reduced pressure to yield 1.8 g of the title compound that is used without further purification. MS (m/z): 232 (M+1).

Preparation 35: 2-Bromo-3-(imidazol-1-ylmethyl)pyridine

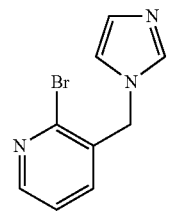

To a solution of (2-bromo-3-pyridyl)methyl methanesulfonate (2.5 g, 9.39 mmol) in ethanol (46.97 mL) at room temperature, potassium carbonate (2.62 g) and 1H-imidazole (1.31 g) are added. The mixture is stirred at 50° C. A thick sort of emulsion is formed and 10 mL of ethanol is added and the kind of emulsion is stirred at 50° C. overnight. Water is added until all solids are dissolved. Then, it is concentrated under reduced pressure and the residue is diluted with ethyl acetate and washed with sodium bicarbonate (saturated aqueous solution). Organic layer is decanted, dried over magnesium sulfate and solvent evaporated in vacuo. Crude material is purified by normal phase Isco chromatography using as eluent dichloromethane and methanol (98/2 to 90/10) to yield 1.42 g of the title compound. MS (m/z): 238, 240 (M+1, M+3).

The compounds of Preparation 36-40 are prepared essentially as described in Preparation 35 from the corresponding nitrogenated heterorings.

| Prep. No. | Chemical name | Structure | Yield (%) | Physical data: MS (m/z) |
|---|---|---|---|---|
| 36 | 2-Bromo-3-(1,2,4-triazol-1-ylmethyl)pyridine | 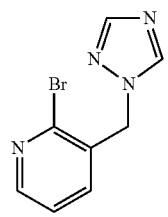 | 39 | 239, 241 (M + 1, M + 3) |

-continued

| Prep. No. | Chemical name | Structure | Yield (%) | Physical data: MS (m/z) |
|---|---|---|---|---|
| 37 | 2-Bromo-3-(triazol-2-ylmethyl)pyridine | 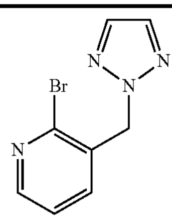 | 33[a] | 239, 241 (M + 1, M + 3) |
| 38 | 2-Bromo-3-(triazol-1-ylmethyl)pyridine | 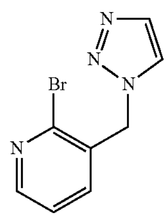 | 63[a] | 239, 241 (M + 1, M + 3) |
| 39 | 2-Bromo-3-(pyrazol-1-ylmethyl)pyridine | 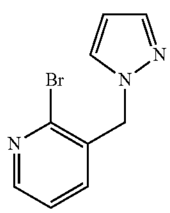 | 41 | 238, 240 (M + 1, M + 3) |
| 40 | 2-Bromo-3-[(2-methylimidazol-1-yl)methyl]pyridine | 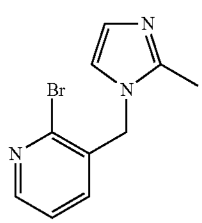 | 61 | 252, 254 (M + 1, M + 3) |

[a]Both compounds are obtained in the same reaction.

Preparation 41:
2-[(2-Bromo-3-pyridyl)oxy]acetamide

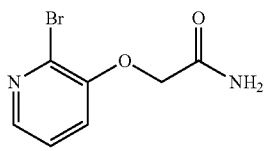

To a solution of 2-bromo-3-pyridinol (1.5 g, 8.49 mmol) in tetrahydrofuran (15 mL) at 0° C. is added 60% sodium hydride in mineral oil (509.44 mg, 12.74 mmol) and the mixture is stirred at that temperature for 30 min. Then acetamide, 2-chloro-(16.98 mmol) is added and the mixture is stirred at room temperature over the weekend. The mixture is quenched with water and extracted with ethyl acetate. The organic layer is separated dried on magnesium sulfate and the solvent evaporated in vacuo to give the title compound in a 75% yield. The compound is used without any further purification. MS (m/z): 231 (M+1), 233 (M+3).

Preparation 42:
2-Bromo-3-(cyclopropylmethoxy)pyridine

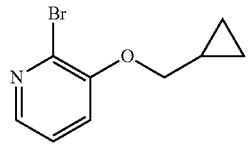

To a solution of 2-bromo-3-pyridinol (500 mg, 2.83 mmol;) in dimethylformamide (3 mL) is added at 0° C. 60% sodium hydride in mineral oil (169.81 mg, 4.25 mmol). The mixture is stirred at that temperature for 15 min and bromomethylcyclopropane (329.66 μL, 3.40 mmol) is added. Then the reaction is stirred at room temperature for 1 h and quenched with water and extracted with ethyl acetate. The organic layer is separated, washed with brine, dried over magnesium sulfate and the solvent evaporated in vacuo. The crude is passed through a short silica gel plug and the compound was eluted with dichloromethane to yield 23% of the title compound. MS (m/z): 228 (M+1), 230 (M+3).

Preparation 43: Ethyl 1-(3-fluoro-2-pyridyl)-4-formyl-pyrazole-3-carboxylate

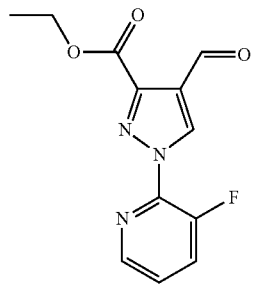

1. Ethyl 4-formyl-1H-pyrazole-3-carboxylate

A 100 mL round bottomed flask is charged with semicarbazide hydrochloride (2 g, 17.93 mmol), ethyl pyruvate (11.8 mL) and sodium ethanoate (2.97 g). Then water (9 mL) is added. The mixture is stirred at room temperature for 90 minutes, then it is filtered and solids are washed with more water. White solid is dried under vacuum in an oven (40° C.) overnight. 2.66 g of ethyl-2-(carbamoylhydrazono)-propanoate is obtained pure. Phosphoryl chloride (3.28 mL) is added dropwise to dimethylformamide (7.13 mL) at 0° C. Cooling bath is removed to reach room temperature Then, the mixture is heated to 40° C. and ethyl-2-(carbamoylhydrazono)propanoate previously obtained (2.66 g, 15.36 mmol) is added in several portions over 15-20 min (gas evolution during the addition). When internal temperature is 55° C., heating bath is removed so internal temperature is maintained in the range 60-70° C. Then, the mixture is heated to 80° C. Almost no more gas evolution is observed once the reaction is stabilized at 80° C. The resulting suspension is stirred at 80° C. for 2 h. Reaction mixture is poured over ice/water (30 mL) mixture and stirred to get a suspension. 50% solution of sodium hydroxide is added dropwise until pH 10 is reached. The solution is stirred at 50° C. for 5 min. Solution is then cooled with ice/water bath and 35% aqueous solution of hydrochloric acid is added until pH 7. The mixture is extracted with ethyl acetate. Organic layer is decanted, dried over magnesium sulfate and solvent is evaporated under reduced pressure. The residue is triturated with hexane and some drops of dichloromethane to give 1.6 g of ethyl 4-formyl-1H-pyrazole-3-carboxylate that is used in the next step without further purification. MS (m/z): 169 (M+1).

2. Ethyl 1-(3-fluoro-2-pyridyl)-4-formyl-pyrazole-3-carboxylate

A mixture of ethyl 4-formyl-1H-pyrazole-3-carboxylate (1.6 g, 9.52 mmol), 2,3-difluorpyridine (1.20 g) and potassium carbonate (1.97 g) in dimethylformamide (8 mL) is heated and stirred at 100° C. for 1.5 h. Then, the reaction mixture is stirred at room temperature overnight. Water is added, and the organic phase is extracted with ethyl acetate, decanted, dried over magnesium sulfate and solvent evaporated under reduced pressure. Crude is purified by normal phase Isco chromatography using ethyl acetate and hexane to give 711 mg of the title compound. MS (m/z): 264 (M+1).

Preparation 44: 3-Methyl-1-(3-(tetrahydrofuran-2-yl)pyridin-2-yl)-1H-pyrazole-4-carbaldehyde

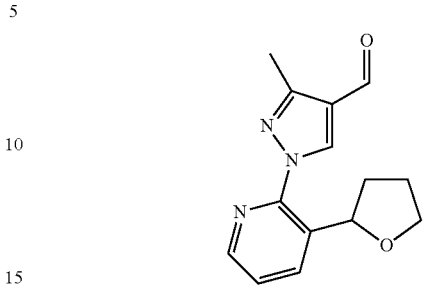

1. 3-(2,5-Dihydrofuran-2-yl)-2-fluoropyridine

To a screw-cap test tube containing potassium acetate (440 mg, 4.5 mmol), tetrabutylammonium bromide (1.4 g, 4.5 mmol) and 4A molecular sieves in dry dimethylformamide (1.8 mL) are added under nitrogen 2-fluoro-3-iodopyridine (400 mg, 1.8 mmol), 2,3-dihydrofurane (1.4 mL, 18 mmol) and palladium acetate (20 mg, 0.09 mmol). The reaction tube is quickly sealed and stirred overnight at room temperature. The mixture is diluted with diethyl ether and the mixture filtered over celite. The filtrate is washed with water, dried over magnesium sulfate, filtered and the solvent evaporated in vacuo. The resulting residue is purified by silica gel using normal phase Isco chromatography eluting with hexane: acetone (gradient from 5 to 30% in acetone) to give 170 mg of 3-(2,5-dihydrofuran-2-yl)-2-fluoropyridine. MS (m/z): 166 (M+1).

2. 2-Fluoro-3-(tetrahydrofuran-2-yl)pyridine

A round-bottom flask containing 3-(2,5-dihydrofuran-2-yl)-2-fluoropyridine (170 mg, 1 mmol) and 10% Pd/C in methanol (3.1 mL) is evacuated under vacuum and filled with hydrogen with the aid of a balloon. The reaction is stirred overnight at room temperature and filtered over celite. The solvent is evaporated in vacuo to give 148 mg of 2-fluoro-3-(tetrahydrofuran-2-yl)pyridine. MS (m/z): 168 (M+1).

3. 3-Methyl-1-(3-(tetrahydrofuran-2-yl)pyridin-2-yl)-1H-pyrazole-4-carbaldehyde To a screw-cap test tube containing 2-fluoro-3-(tetrahydrofuran-2-yl)pyridine (148 mg, 0.88 mmol) in dimethylformamide (2.2 mL) are added 3-methyl-1H-pyrazole-4-carbaldehyde (81 mg, 0.74 mmol) and potassium carbonate (152 mg, 1.1 mmol). The reaction tube is quickly sealed (caution: build-up of pressure possible; use a safety shield) and stirred in a preheated oil bath at 110° C. for 18 h with the aid of a magnetic stirrer. The mixture is diluted with water and extracted with ethyl acetate. The organic layer is separated, dried over magnesium sulfate, filtered and the solvent evaporated in vacuo. The resulting residue is purified by silica gel using normal phase Isco chromatography eluting with hexane: acetone (gradient from 5 to 20% in acetone) to give 116 mg of the title compound. MS (m/z): 258 (M+1).

Preparation 45: 3-(2-Bromo-pyrid-3-yl)isoxazole

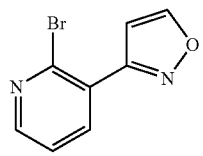

1. 2-Bromopyridine-3-carbaldehyde oxime

To a solution of 2-bromopyridine-3-carbaldehyde (2.04 g) in ethanol (25 mL) is added hydroxylamine hydrochloride (948 mg, 13.16 mmol) and sodium ethanoate (1.09 g, 13.16 mmol). The mixture is stirred at room temperature overnight. The solvent is evaporated under reduced pressure and the residue partitioned between dichloromethane and water. The organic layer is separated, dried over sodium sulfate, filtered and solvent evaporated in vacuo to give 2 g of 2-bromopyridine-3-carbaldehyde oxime. MS (m/z): 201/203 (M+1/M+3)

2. [3-(2-Bromo-3-pyridyl)isoxazol-5-yl]-trimethyl-silane

To a stirring suspension of 2-bromopyridine-3-carbaldehyde oxime (400 mg, 1.99 mmol) in dichloromethane (3.98 mL) at 0° C., pyridine (201.13 µl, 2.49 mmol) followed by N-chlorosuccinimide (337.19 mg, 2.49 mmol) are added in portions. Then, trimethylsilyl)acetylene (350.60 µl, 2.49 mmol) followed by triethylamine (346.68 µL, 2.49 mmol) are added. The mixture is stirred from 0° C. to room temperature. After two hours, more pyridine (321.81 µL, 3.98 mmol) and N-chlorosuccinimide (539.51 mg, 3.98 mmol) are added and the mixture is stirred at room temperature for 16 hours. The reaction mixture is then quenched with saturated solution of ammonium chloride. The layers are separated and the organics are dried over magnesium sulfate, filtered and concentrated under reduced pressure to give [3-(2-bromo-3-pyridyl)isoxazol-5-yl]-trimethyl-silane in quantitative yield. MS (m/z): 297/299 (M+1/M+3)

3. 3-(2-Bromo-3-pyridyl)isoxazole

To a solution of [3-(2-bromo-3-pyridyl)isoxazol-5-yl]-trimethyl-silane (620 mg, 2.09 mmol) in methanol (18 mL), potassium carbonate (29.12 mg, 208.59 µmoles) is added in one portion. The mixture is stirred at room temperature for 24 h. The solvent is removed in vacuum. The crude is partitioned between ethyl acetate and saturated solution of ammonium chloride. The organics are washed with water and dried over magnesium sulfate, filtered and concentrated under reduced pressure. The crude is purified by normal phase Isco chromatography using as eluent hexane/ethyl acetate from 66/33 to 50/50 as to give 140 mg of title compound as white solid. MS (m/z): 225/227 (M+1/M+3)

Preparation 46: 1-(3-Chloro-2-pyridyl)-3-methyl-pyrazole-4-carbaldehyde

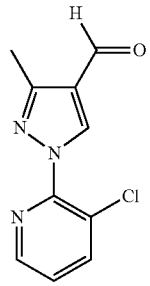

To a solution of 3-methyl-pyrazole-4-carbaldehyde (0.5 g, 4.5 mmol) in dry dimethylformamide (15 mL) is added potassium carbonate (2.5 g, 18 mmol,) at room temperature. The reaction mixture is stirred at 40° C. for 30 min and then 1-fluoro-2-chloropyridine (0.77 g, 6 mmol,) is added. The reaction mixture is heated at 70° C. for 16 h. After completion, the reaction mixture is cooled to room temperature, diluted with water and then extracted with ethyl acetate. The organic layer is dried over sodium sulfate, filtered and concentrated under reduce pressure. The crude mixture is purified by chromatography on silica gel eluting with hexane/ethyl acetate (75:25, 65:35) to yield 0.525 g (52%) of the title compound. MS (m/z): 222 (M+1).

Preparation 47: 1-(3-Cyclopropyl-2-pyridyl)-3-methyl-pyrazole-4-carbaldehyde

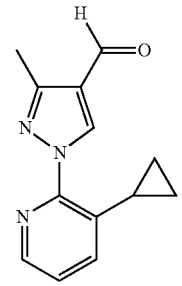

1. 1-(3-Bromo-pyridin-2-yl)-3-methyl-pyrazole-4-carboxylic acid ethyl ester

To the solution of 3-methyl-pyrazole-4-carboxylic acid ethyl ester (2.0 g, 13 mmol) in dry dimethylformamide (30 mL) is added potassium carbonate (7.2 g, 52 mmol) at room temperature. The reaction mixture is stirred at 40° C. for 30 min and then 1-fluoro-2-bromopyridine (3.0 g, 17 mmol) is added. The reaction mixture is stirred at 70° C. for 4 h. The reaction mixture is cooled to room temperature, diluted with water and then extracted with ethyl acetate. The organic layer is dried over anhydrous sodium sulfate, filtered and concentrated under reduce pressure. The crude mixture was purified by chromatography on silica gel eluting with hexane/ethyl acetate (85:15, 80:20) to yield 3.2 g (79%) of 1-(3-bromo-pyridin-2-yl)-3-methyl-pyrazole-4-carboxylic acid ethyl ester. MS (m/z): 312 (M+3), 310 (M+1).

2. 1-(3-Cyclopropyl-pyridin-2-yl)-3-methyl-pyrazole-4-carboxylic acid ethyl ester A mixture of 1-(3-bromo-pyridin-2-yl)-3-methyl-pyrazole-4-carboxylic acid ethyl ester (1.5 g, 5.5 mmol), potassium phosphate (4.0 g, 19.2 mmol), cyclopropyl boronic acid (0.7 g, 8.2 mmol) and toluene/water (2:1, 15 mL) is degassed with nitrogen and tricylohexylphosphene (0.153 g, 0.54 mmol) and palladium acetate (0.061 g, 0.27 mmol) are added. The mixture is degassed again with nitrogen and the reaction vessel is sealed and heated at 100° C. for 16 h. The reaction mixture is concentrated, diluted with water and extracted with ethyl acetate. The organic layer is dried over sodium sulfate, filtered and concentrated under reduced pressure. The crude mixture is purified by chromatography on silica gel eluting with hexane/ethyl acetate (85:15) to yield 1.6 g (93%) of 1-(3-cyclopropyl-pyridin-2-yl)-3-methyl-pyrazole-4-carboxylic acid ethyl ester. MS (m/z): 272 (M+1).

3. [1-(3-Cyclopropyl-pyridin-2-yl)-3-methyl-pyrazol-4-yl]-methanol

To a stirred suspension of lithium aluminium hydride (0.44 g, 11.7 mmol) in dry tetrahydrofuran (25 mL) is added a solution of 1-(3-bromo-pyridin-2-yl)-3-methyl-pyrazole-4-carboxylic acid ethyl ester (1.6 g, 5.8 mmol) in dry tetrahydrofuran (5 mL) under nitrogen atmosphere at −78° C. After complete addition the reaction mixture is warmed to room temperature then stir overnight. The reaction mixture is quenched with 1N sodium hydroxide then filtered through the celite. The organic layer is separated and the aqueous layer is extracted with ethyl acetate. The combined organic layer is washed with water and brine, dried on sodium sulfate, filtered and concentrated to yield 1.1 g (84%) of [1-(3-cyclopropyl-pyridin-2-yl)-3-methyl-pyrazol-4-yl]-methanol. MS (m/z): 230 (M+1).

4. 1-(3-Cyclopropyl-2-pyridyl)-3-methyl-pyrazole-4-carbaldehyde

To a solution of [1-(3-cyclopropyl-pyridin-2-yl)-3-methyl-pyrazol-4-yl]-methanol (1.1 g, 5.0 mmol) in dry dichloromethane (15 mL) is added pyridinium chlorocromate (1.2 g, 5.5 mmol) under nitrogen atmosphere. The reaction mixture is stirred at room temperature for 2 h and then filtered through celite. The filtrate is concentrated under reduced pressure. The crude mixture is purified on silica gel eluting with hexane/ethyl acetate (90:10, 80:20) to yield 0.2 g (20%) of the title compound. MS (m/z): 228 (M+1).

Preparation 48: 4-[(2-Bromo-3-pyridyl)methyl]morpholin-3-one

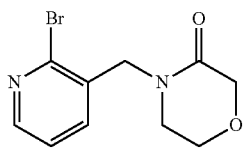

To a solution of 2-bromo-3-bromomethyl-pyridine (0.68 g, 2.36 mmol) in dimethylformamide (10 mL) are added sodium hydride (0.11 g, 60% suspension, 2.82 mmol), morpholin-3-one (0.20 g, 1.97 mmol) and tetrabutylammonium iodide (catalytic) at 0° C. The mixture is stirred at room temperature for 16 hours. After completion, the reaction mixture is partitioned between ethyl acetate (25 mL) and water (25 mL). The aqueous layer is extracted with ethyl acetate (2×25 mL) and the combined organic extracts are dried over sodium sulfate and concentrated in vacuo. The crude material is purified by column chromatography over silica gel eluting with hexane/ethyl acetate (55:45) to yield 0.35 g (66%) of the title compound. MS (m/z): 271/273 (M+1, M+3).

The compounds of Preparation 49-50 are prepared essentially as described in Preparation 48 from the corresponding lactame reagent.

| Prep. No. | Chemical name | Structure | Yield (%) | Physical data: MS (m/z) |
|---|---|---|---|---|
| 49 | 1-[(2-Bromo-3-pyridyl)methyl]-pyrrolidin-2-one | 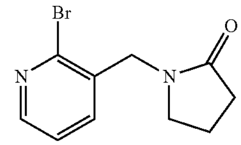 | 80 | 255/257 (M + 1, M + 3) |
| 50 | 1-[(2-Bromo-3-pyridyl)methyl]-piperidin-2-one | 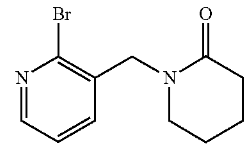 | 59 | 269/271 (M + 1/M + 3) |

Preparation 51: Ethyl 1-(3-Chloro-2-pyridyl)-4-formyl-pyrazole-3-carboxylate

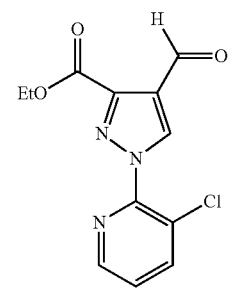

To a solution of ethyl 4-formyl-pyrazole-3-carboxylate (1.70 g, 10.1 mmol) and 3-chloro-2-fluoropyridine (1.99 g, 15.1 mmol) in dimethylformamide (20 mL) is added potassium carbonate (2.80 g, 20.2 mmol) and the mixture is stirred at 100° C. for 16 hours. After completion, the reaction mixture is partitioned between water (25 mL) and ethyl acetate (25 mL). The aqueous layer is extracted with ethyl acetate (3×25 mL) and the combined organic extracts are dried over sodium sulfate, concentrated in vacuo and purified by column chromatography over silica gel eluting with hexane/ethyl acetate (50:50) to yield 1.5 g (54%) of the title compound. MS (m/z): 280 (M+1).

Preparation 52: Ethyl 1-(3-methyl-2-pyridyl)-4-formyl-pyrazole-3-carboxylate

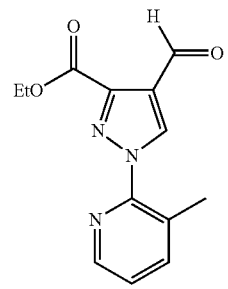

A mixture of ethyl 1-(3-chloro-2-pyridyl)-4-formyl-pyrazole-3-carboxylate (1.0 g, 3.5 mmol), trimethylboroxine (0.44 g, 3.50 mmol) and potassium carbonate (1.4 g, 10.1 mmol) in dioxane (18 mL) and water (2 mL) is degassed with nitrogen gas for 10 min and then palladium triphenylphosphine (0.40 g, 0.3 mmol) is added and stirred at 110° C. for 16 h. After completion, the reaction mixture is partitioned between dichloromethane (50 mL) and water (25 mL). The aqueous layer is extracted with dichloromethane (2×25 mL) and the combined organic extracts are dried over sodium sulfate and concentrated in vacuo. The crude mixture is purified by column chromatography over silica gel eluting with hexane/ethyl acetate (70:30) to yield 0.12 g (13%) of the title compound. MS (m/z): 260 (M+1).

EXAMPLE 1

[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanol (L)-tartrate

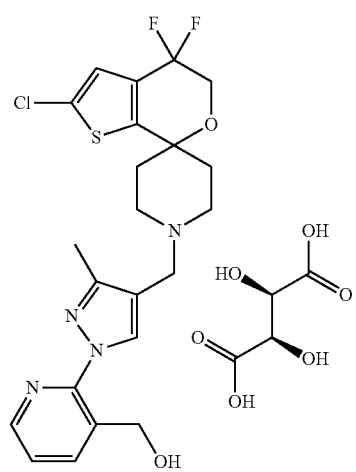

To a solution of 2-[4-[(2-chloro-4,4-difluoro-spiro[5H-thieno[2,3-c]pyran-7,4'-piperidine]-1'-yl)methyl]-3-methyl-pyrazol-1-yl]pyridine-3-carbaldehyde (12.50 g, 26.10 mmol) in dichloromethane (125 mL) at 0° C. is added sodium borohydride (0.395 g, 10.44 mmol) and methanol (37.50 mL). The ice bath is removed and the reaction is stirred at room temperature for 30 min. Water (50 mL) is added and the mixture is concentrated to half volume resulting in a white sticky solid precipitate. Dichloromethane (100 mL) is added and the biphasic mixture is separated. The organic layer is washed with water (50 mL), dried over sodium sulfate and concentrated to half volume (around 100 mL). Methyl tert-butyl ether (100 mL) is added and the solution is concentrated to provide a precipitate. The solid is filtered and dried under vacuum to give 12 g of [2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol. MS (m/z): 481 (M+1).

The free base of the title compound (0.48 g, 1 mmol) is dissolved in 3 mL of methanol and a solution of (L)-tartaric acid (0.15 g, 1 mmol) in methanol is added. The mixture is stirred for ten minutes. The solvent is evaporated and the residue is dried in vacuo overnight to give [2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol (L)-tartrate in a quantitative yield. MS (m/z): 481 (M+1).

EXAMPLE 2

2-Chloro-4,4-difluoro-1'-[[1-[3-(4H-imidazol-2-yl)-2-pyridyl]-3-methyl-pyrazol-4-yl]methyl]spiro[5H-thieno[2,3-c]pyran-7,4'-piperidine]

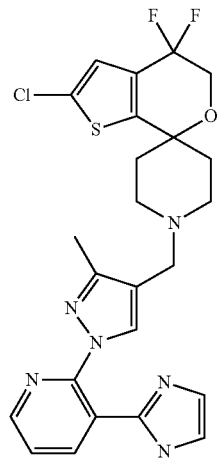

A solution of 40% glyoxal in water (4.69 mL, 40.71 mmol) and 2N ammonia in methanol (54.29 mL, 108.57 mmol) are added to a suspension of 2-[4-[(2-chloro-4,4-difluoro-spiro[5H-thieno[2,3-c]pyran-7,4'-piperidine]-1'-yl)methyl]-3-methyl-pyrazol-1-yl]pyridine-3-carbaldehyde (6.50 g, 13.57 mmol) in methanol (10 mL). The reaction mixture is stirred for five minutes at 0° C. and then at 40° C. for 1 hr. Dichloromethane (10 mL) is added to the suspension dissolving almost all material. The mixture is stirred for 4 hr. resulting in a light brown solution. The solution is stirred for 8 hr. at 40° C. 40% Glyoxal in water (2.34 mL, 20.36 mmol) and 2 N ammonia in methanol (27.14 mL, 54.29 mmol) are added and the mixture is stirred at 40° C. for 15 hr. The reaction mixture is concentrated to approximately 100 mL and poured over ice/water (400 mL) and a beige solid precipitate is formed. The solid is filtered, washed with water and dried under vacuum (7 g). The solid is combined with other crude material prepared essentially by the same method (10 g). The combined solid is dissolved in dichloromethane and filtered through a pad of silica gel eluting with dichloromethane/methanol (96/4). Fractions containing product are combined and concentrated to afford a light yellow solid (11 g). Solid is extracted with 10% hexane/dichloromethane under reflux and the filtrate is concentrated. Solid is further purified via silica gel chromatography eluting with 2N ammonium hydroxide in methanol/dichloromethane mixtures, to afford 6.5 g of title compound. MS (m/z): 518 (M+1).

EXAMPLE 3

2-Fluoro-1'-[[1-[3-(1H-imidazol-2-yl)-2-pyridyl]-3-methyl-pyrazol-4-yl]methyl]spiro[4,5-dihydrothieno[2,3-c]pyran-7,4'-piperidine]

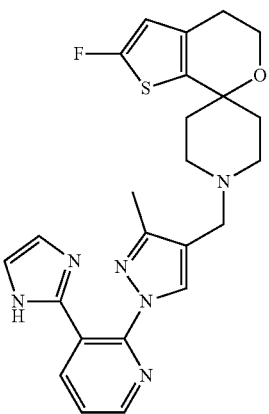

This compound is prepared essentially as described in Example 2 by using 2-[4-[(2-fluorospiro[4,5-dihydrothieno[2,3-c]pyran-7,4'-piperidine]-1'-yl)methyl]-3-methyl-pyrazol-1-yl]pyridine-3-carbaldehyde. Residue is purified by normal phase Isco chromatography to yield 32% of the title compound: mass spectrum (m/z): 465 (M+1).

EXAMPLE 4

5-(2-(4-((2'-Chloro-4',4'-difluoro-4',5'-dihydrospiro[piperidine-4,7'-thieno[2,3-c]pyran]-1-yl)methyl)-3-methyl-1H-pyrazol-1-yl)pyridin-3-yl)oxazole

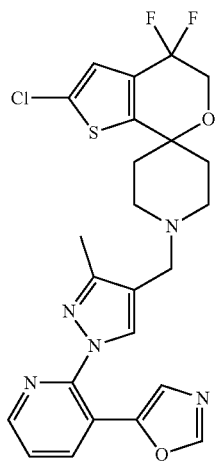

To a screw-cap test tube containing 2-(4-((2'-chloro-4',4'-difluoro-4',5'-dihydrospiro[piperidine-4,7'-thieno[2,3-c]pyran]-1-yl)methyl)-3-methyl-1H-pyrazol-1-yl)nicotinaldehyde (0.120 g, 0.25 mmol) in methanol (2.5 mL) are added potassium carbonate (0.104 g, 0.75 mmol) and p-toluenesulfonylmethyl isocyanide (0.054 g, 0.28 mmol) under nitrogen. The reaction tube is quickly sealed (caution: build-up of pressure possible; use a safety shield) and is stirred in a preheated oil bath at 65° C. for 3 hr. with the aid of a magnetic stirrer. The mixture is diluted with methanol and purified using a 2 g SCX cartridge. The solvent is evaporated in vacuo. The resulting residue is purified by normal phase Isco chromatography eluting with hexane/ethanol (5-30%) to give 0.093 g of the title compound. MS (m/z): 518 (M+1)

EXAMPLE 5

2-Chloro-4,4-difluoro-1'-[[1-(3-fluoro-2-pyridyl)-3-methyl-pyrazol-4-yl]methyl]spiro[5H-thieno[2,3-c]pyran-7,4'-piperidine] (L)-Tartrate

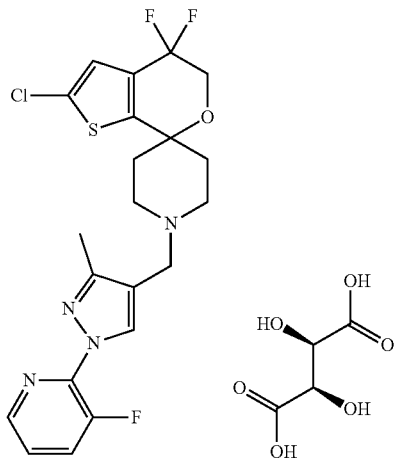

To a solution of 2-chloro-4,4-difluoro-spiro[5H-thieno[2,3-c]pyran-7,4'-piperidine] (19.99 g, 64.33 mmol) in 1,2-dichloroethane (120 mL) is added 1-(3-fluoro-2-pyridyl)-3-methyl-pyrazole-4-carbaldehyde (12 g, 58.48 mmol) and the mixture is stirred at room temperature for 15 min. Then, powdered sodium triacetoxiborohydride (18.59 g, 87.72 mmol) is added (internal temperature 25-35°) and the resulting suspension is stirred at room temperature for 15 hr. A saturated aqueous solution of sodium bicarbonate in ice mixture (200 mL) is added in portions with stirring. The phases are separated. The aqueous phase is extracted with tert-butyl methyl ether (30 mL). Combined organic layers are washed with water (50 mL) and 50% brine (50 mL), dried over sodium sulfate and concentrated to afford a thick oil which is purified via silica gel chromatography using dichloromethane/methanol mixtures as eluent to give 18 g of a thick oil which is triturated with hexane and 10% tert-butyl methyl ether/hexane to afford 16.5 g of 2-chloro-4,4-difluoro-1'-[[1-(3-fluoro-2-pyridyl)-3-methyl-pyrazol-4-yl]methyl]spiro[5H-thieno[2,3-c]pyran-7,4'-piperidine]. MS (m/z): 469 (M+1).

The tartrate salt is essentially prepared as described in Example 1. MS (m/z): 469 (M+1).

The compounds of Example 6-15 are prepared essentially as described in Example 5 using the corresponding aldehyde.

| Ex. | Chemical Name | Structure | Yield % | Physical Data: MS(m/z) |
|---|---|---|---|---|
| 6 | 1-[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]-N,N-dimethyl-methanamine (L)-Tartrate | 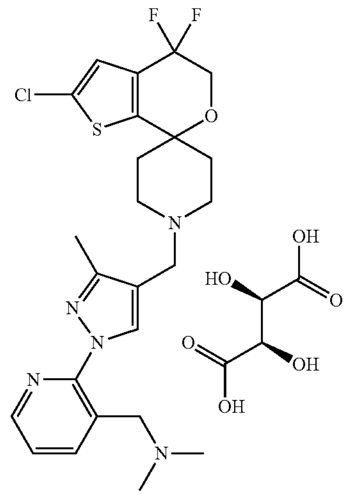 | 39 | 508 (M + 1) |
| 7 | N-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methyl]acetamide (L)-Tartrate | 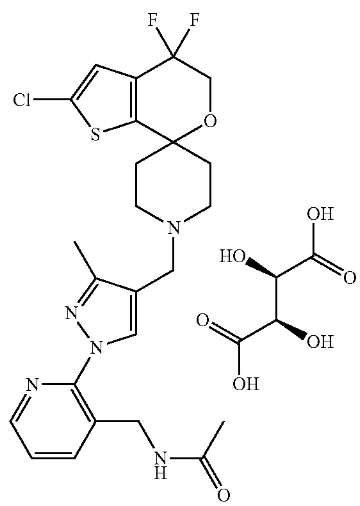 | 23 | 523 (M + 1) |
| 8 | 2-Fluoro-1'-[[1-[3-(methoxymethyl)-2-pyridyl]-3-methyl-pyrazol-4-yl]methyl]spiro[4,5-dihydrothieno[2,3-c]pyran-7,4'-piperidine] (L)-Tartrate | 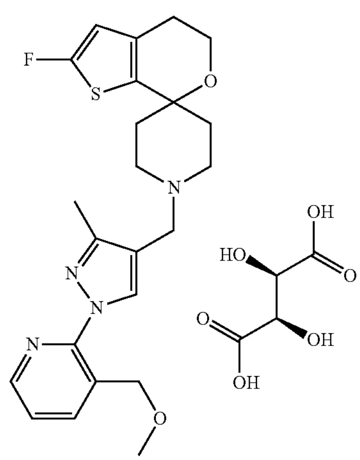 | 46$^a$ | 443 (M + 1) |

-continued

| Ex. | Chemical Name | Structure | Yield % | Physical Data: MS(m/z) |
|---|---|---|---|---|
| 9 | 2-Fluoro-1'-[[1-(3-fluoro-2-pyridyl)-3-methyl-pyrazol-4-yl]methyl]spiro[4,5-dihydrothieno[2,3-c]pyran-7,4'-piperidine] (L)-Tartrate | 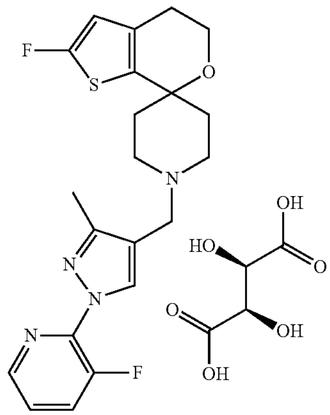 | 38[a] | 417 (M + 1) |
| 10 | 2,4,4-Trifluoro-1'-[[1-[3-(methoxymethyl)-2-pyridyl]-3-methyl-pyrazol-4-yl]methyl]spiro[5H-thieno[2,3-c]pyran-7,4'-piperidine] (L)-Tartrate | 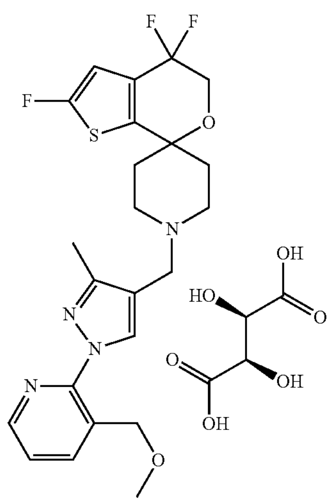 | 72 | 479 (M + 1) |
| 11 | 2-Chloro-4,4-difluoro-1'-[[1-(3-fluoro-2-pyridyl)-3-(methoxymethyl)pyrazol-4-yl]methyl]spiro[5H-thieno[2,3-c]pyran-7,4'-piperidine] (L)-Tartrate | 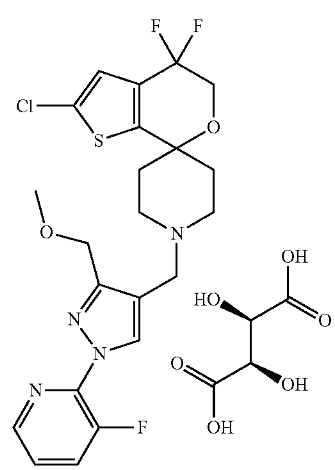 | 64 | 499 (M + 1) |

-continued

| Ex. | Chemical Name | Structure | Yield % | Physical Data: MS(m/z) |
|---|---|---|---|---|
| 12 | 2,4,4-Trifluoro-1'-[[1-(3-fluoro-2-pyridyl)-3-methyl-pyrazol-4-yl]methyl]spiro[5H-thieno[2,3-c]pyran-7,4'-piperidine] (L)-Tartrate | 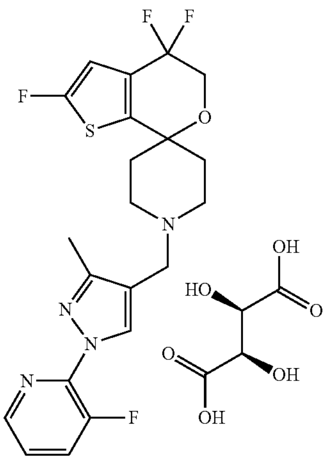 | 51 | 453 (M + 1) |
| 13 | 2-Chloro-4,4-difluoro-1'-[[3-methyl-1-(3-morpholino-2-pyridyl)pyrazol-4-yl]methyl]spiro[5H-thieno[2,3-c]pyran-7,4'-piperidine] (L)-Tartrate | 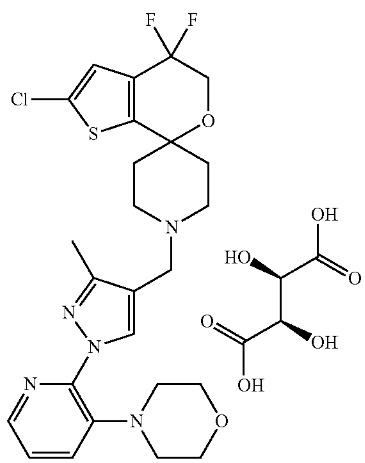 | 60 | 536 (M + 1) |
| 14 | 2-Chloro-1'-[[1-[3-(methoxymethyl)-2-pyridyl]-3-methyl-pyrazol-4-yl]methyl]spiro[4,5-dihydrothieno[2,3-c]pyran-7,4'-piperidine] (L)-Tartrate | 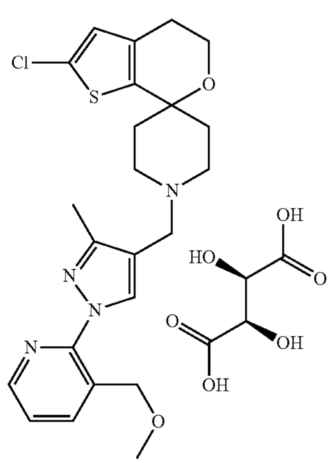 | 76 | 459 (M + 1) |

| Ex. | Chemical Name | Structure | Yield % | Physical Data: MS(m/z) |
|---|---|---|---|---|
| 15 | 2-Chloro-1'-[[1-[3-(cyclopropoxymethyl)-2-pyridyl]-3-methyl-pyrazol-4-yl]methyl]-4,4-difluoro-spiro[5H-thieno[2,3-c]pyran-7,4'-piperidine] (L)-Tartrate | 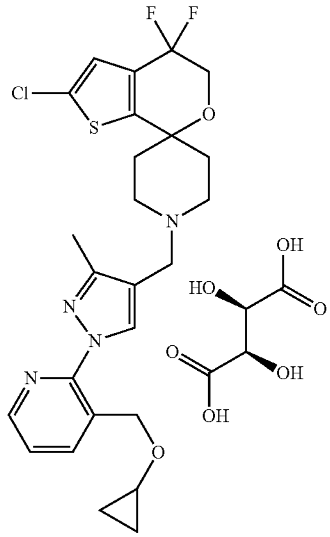 | 69 | 521 (M + 1) |

<sup>a</sup>Reactions are carried out using tetrahydrofuran as solvent.

EXAMPLE 16

2-Chloro-4,4-difluoro-1'-[[3-methyl-1-(3-tetrahydrofuran-2-yl-2-pyridyl)pyrazol-4-yl]methyl]spiro[5H-thieno[2,3-c]pyran-7,4'-piperidine]

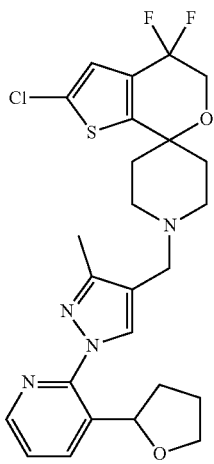

To a screw-cap test tube containing a mixture of 3-methyl-1-(3-(tetrahydrofuran-2-yl)pyridin-2-yl)-1H-pyrazole-4-carbaldehyde (192 mg, 0.75 mmol), 2'-chloro-4',4'-difluoro-4',5'-dihydrospiro[piperidine-4,7'-thieno[2,3-c]pyrane (209 mg, 0.75 mmol) and acetic acid (43 µL, 0.75 mmol) in 1,2-dichloroethane (2.6 mL) is added sodium triacetoxyborohydride (238 mg, 1.1 mmol). The reaction tube is sealed and stirred at room temperature for 18 hr. with the aid of a magnetic stirrer. The mixture is diluted with methanol and purified using a 10 g SCX cartridge and the solvent evaporated in vacuo. The resulting residue is further purified by normal phase Isco chromatography eluting with hexane:acetone (gradient from 5 to 30% in acetone) to give 113 mg of the title compound as a racemic mixture. MS (m/z): 521 (M+1).

Enantiomeric resolution is carried out under SCF (supercritical fluid chromatography) conditions using Chiralpak AD-H® (Chiral Technologies, Inc., West Chester, Pa., USA) as stationary phase and carbon dioxide/methanol/dimethyl ethyl amine (0.2%) as mobile phase. The first eluent is the desired enantiomer.

EXAMPLE 17

2-Chloro-4,4-difluoro-1'-[[1-(3-fluoro-2-pyridyl)-3-(isopropoxymethyl)pyrazol-4-yl]methyl]spiro[5H-thieno[2,3-c]pyran-7,4'-piperidine] (L)-Tartrate

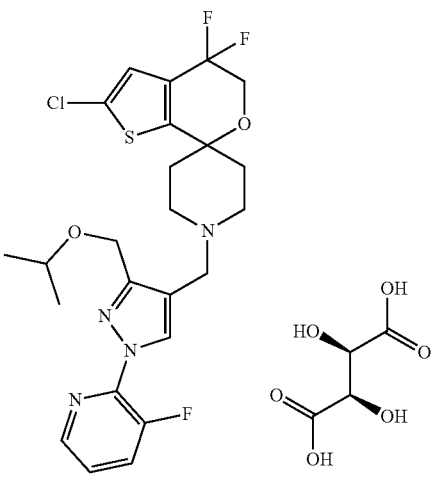

To a solution of 2-chloro-4,4-difluoro-spiro[5H-thieno[2,3-c]pyran-7,4'-piperidine] (170 mg, 0.61 mmol) in dichloromethane (2.4 mL), 1-(3-fluoro-2-pyridyl)-3-(isopropoxymethyl)pyrazole-4-carbaldehyde (192 mg) is added. The mixture is stirred 10 min at room temperature. Then, sodium triacetoxyborohydride (268.3 mg) is added, and the reaction is stirred at room temperature overnight. The mixture is diluted with dichloromethane and quenched slowly with sodium bicarbonate (saturated solution). The organic phase is then extracted with more dichloromethane, decanted, dried over magnesium sulfate and solvent evaporated under reduced pressure. The residue is purified by reverse phase HPLC to give 67.9 mg of 2-chloro-4,4-difluoro-1'-[[1-(3-fluoro-2-pyridyl)-3-(isopropoxymethyl)pyrazol-4-yl]methyl]spiro[5H-thieno[2,3-c]pyran-7,4'-piperidine]. MS (m/z): 527 (M+1).

The tartrate salt is essentially prepared as described in Example 1. MS (m/z): 527 (M+1).

EXAMPLE 18

2-Chloro-4,4-difluoro-1'-[[1-[3-(methoxymethyl)-2-pyridyl]-3-methyl-pyrazol-4-yl]methyl]spiro[5H-thieno[2,3-c]pyran-7,4'-piperidine] (L)-Tartrate

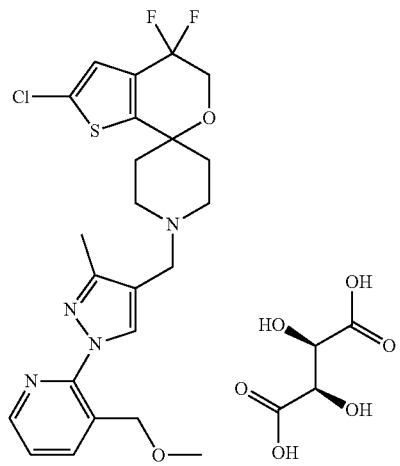

To a screw-cap test tube is added copper (I) iodide (1.15 g, 6.02 mmol), 2-chloro-4,4-difluoro-1'-[(3-methyl-1H-pyrazol-4-yl)methyl]spiro[5H-thieno[2,3-c]pyran-7,4'-piperidine] (15 g, 40.12 mmol), potassium carbonate (11.76 g, 84.26 mmol), 15 mL of toluene (previously bubbled with nitrogen for 20 minutes) and a stir bar. The reaction mixture is bubbled with nitrogen for additional 10 min and then 2-bromo-3-methoxymethyl-pyridine (10.54 g, 52.16 mmol), and trans-N,N'-dimethylcyclohexane-1,2-diamine (1.90 mL, 12.04 mmol) are added. The reaction tube is quickly sealed (caution: build-up of pressure possible; use a safety shield), stirred at room temperature for 5 min and immersed in a preheated oil bath at 115° C. for 24 h. The sample is cooled down to room temperature, diluted with ethyl acetate and filtered through celite. The solvent is evaporated in vacuo. The residue is purified by normal phase Isco chromatography using hexane/ethyl acetate (30-70%). The desired fractions are collected and evaporated. Some impure fractions (<2 g) are repurified by normal phase Isco chromatography using hexane/ethyl acetate (20-60% in ethyl acetate) as eluent. All the fractions containing final compound are combined and evaporated to dryness in vacuo. The residue is dissolved in dichloromethane and washed with 10% aqueous solution of ammonium hydroxide to remove copper residues. The organic solvent is evaporated and the compound is dried overnight to yield 13 g of 2-chloro-4,4-difluoro-1'-[[1-[3-(methoxymethyl)-2-pyridyl]-3-methyl-pyrazol-4-yl]methyl]spiro[5H-thieno[2,3-c]pyran-7,4'-piperidine]. MS (m/z): 495 (M+1).

The tartrate salt is essentially prepared as described in Example 1. MS (m/z): 495 (M+1).

The compounds of Example 19-35 are prepared essentially as described in Example 18 from the corresponding 2-bromo-3-substituted pyridine (examples 19-32 & 34-35) or the 2-iodo-3-substituted pyridine (example 33).

| Ex. No. | Chemical name | Structure | Yield (%) | Physical data: MS (m/z) |
|---|---|---|---|---|
| 19 | 2-Chloro-1'-[[1-[3-(ethoxymethyl)-2-pyridyl]-3-methyl-pyrazol-4-yl]methyl]-4,4-difluoro-spiro[5H-thieno[2,3-c]pyran-7,4'-piperidine] (L)-Tartrate | 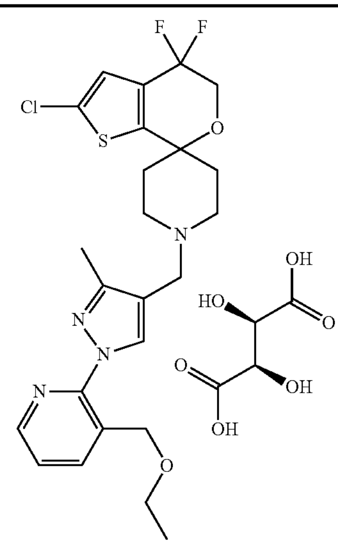 | 50 | 509 (M + 1) |

| Ex. No. | Chemical name | Structure | Yield (%) | Physical data: MS (m/z) |
|---|---|---|---|---|
| 20 | 2-Chloro-1'-[[1-[3-(cyclopropylmethoxymethyl)-2-pyridyl]-3-methyl-pyrazol-4-yl]methyl]-4,4-difluoro-spiro[5H-thieno[2,3-c]pyran-7,4'-piperidine] (L)-Tartrate | 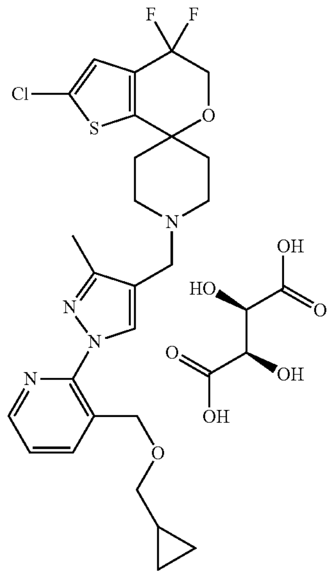 | 65 | 535 (M + 1) |
| 21 | 2-Chloro-4,4-difluoro-1'-[[1-[3-(isopropoxymethyl)-2-pyridyl]-3-methyl-pyrazol-4-yl]methyl]spiro[5H-thieno[2,3-c]pyran-7,4'-piperidine] (L)-Tartrate | 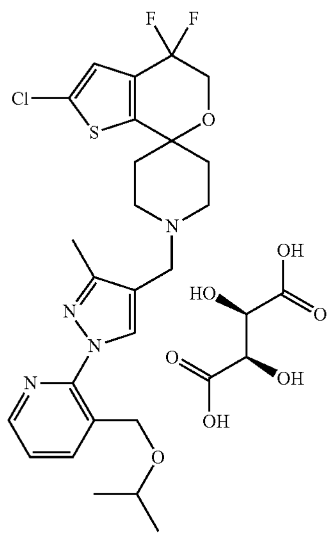 | 59 | 523 (M + 1) |
| 22 | 2-Chloro-4,4-difluoro-1'-[[3-methyl-1-(3-methyl-2-pyridyl)pyrazol-4-yl]methyl]spiro[5H-thieno[2,3-c]pyran-7,4'-piperidine] (L)-Tartrate | 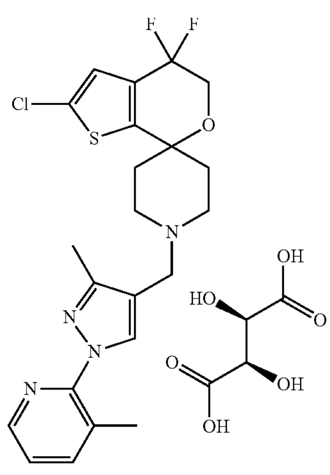 | 53 | 465 (M + 1) |

-continued

| Ex. No. | Chemical name | Structure | Yield (%) | Physical data: MS (m/z) |
|---|---|---|---|---|
| 23 | 2-Chloro-4,4-difluoro-1'-[[3-methyl-1-[3-(pyrazol-1-ylmethyl)-2-pyridyl]pyrazol-4-yl]methyl]spiro[5H-thieno[2,3-c]pyran-7,4'-piperidine] (L)-Tartrate | 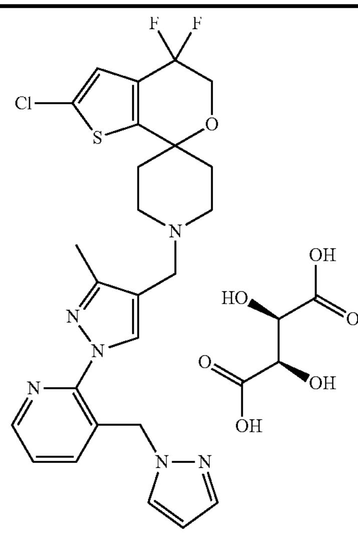 | 30 | 531 (M + 1) |
| 24 | 2-Chloro-4,4-difluoro-1'-[[3-methyl-1-[3-(triazol-2-ylmethyl)-2-pyridyl]pyrazol-4-yl]methyl]spiro[5H-thieno[2,3-c]pyran-7,4'-piperidine] (L)-Tartrate | 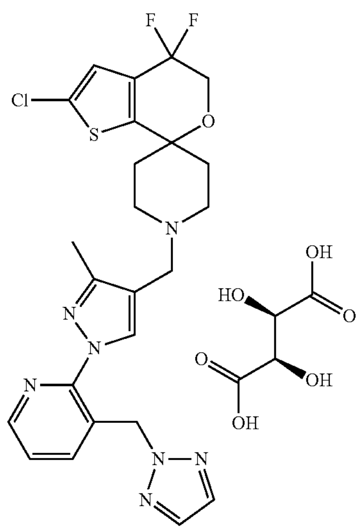 | 44 | 532 (M + 1) |
| 25 | 2-Chloro-4,4-difluoro-1'-[[3-methyl-1-[3-(1,2,4-triazol-1-ylmethyl)-2-pyridyl]pyrazol-4-yl]methyl]spiro[5H-thieno[2,3-c]pyran-7,4'-piperidine] (L)-Tartrate | 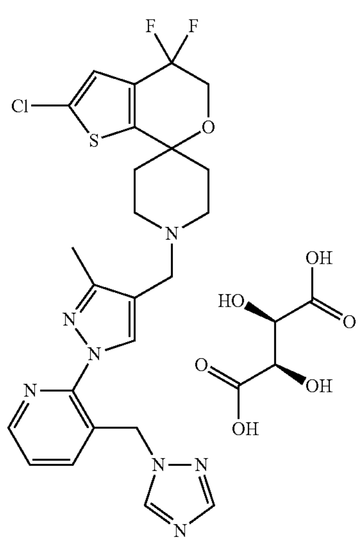 | 62 | 532 (M + 1) |

-continued

| Ex. No. | Chemical name | Structure | Yield (%) | Physical data: MS (m/z) |
|---|---|---|---|---|
| 26 | 2-Fluoro-1'-[[3-methyl-1-[3-(1,2,4-triazol-1-ylmethyl)-2-pyridyl]pyrazol-4-yl]methyl]spiro[4,5-dihydrothieno[2,3-c]pyran-7,4'-piperidine] (L)-Tartrate | 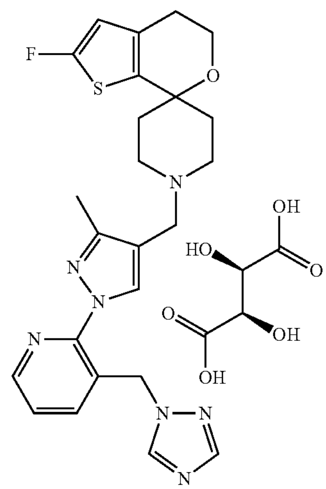 | 70 | 480 (M + 1) |
| 27 | 2-Chloro-4,4-difluoro-1'-[[1-[3-(imidazol-1-ylmethyl)-2-pyridyl]-3-methyl-pyrazol-4-yl]methyl]spiro[5H-thieno[2,3-c]pyran-7,4'-piperidine] (L)-Tartrate | 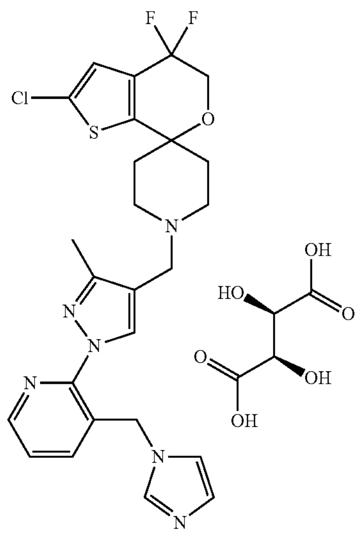 | 37 | 531 (M + 1) |
| 28 | 2-[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]acetonitrile (L)-Tartrate | 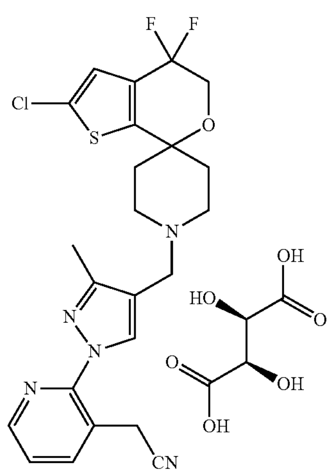 | 51 | 490 (M + 1) |

-continued

| Ex. No. | Chemical name | Structure | Yield (%) | Physical data: MS (m/z) |
|---|---|---|---|---|
| 29 | 2-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]oxy]acetamide (L)-Tartrate | 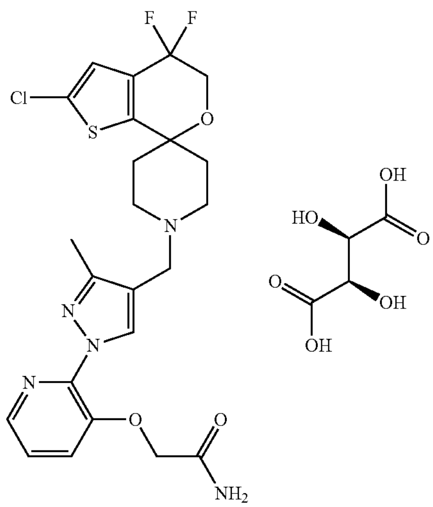 | 13 | 524 (M + 1) |
| 30 | 2-Fluoro-1'-[[3-methyl-1-[3-[(2-methylimidazol-1-yl)methyl]-2-pyridyl]pyrazol-4-yl]methyl]spiro[4,5-dihydrothieno[2,3-c]pyran-7,4'-piperidine] (L)-Tartrate | 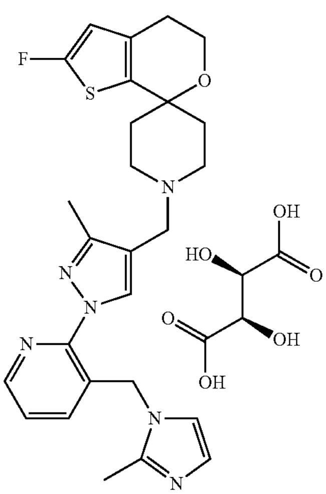 | 57 | 493 (M + 1) |
| 31 | 2-Chloro-4,4-difluoro-1'-[[3-methyl-1-[3-(triazol-1-ylmethyl)-2-pyridyl]pyrazol-4-yl]methyl]spiro[5H-thieno[2,3-c]pyran-7,4'-piperidine] (L)-Tartrate | 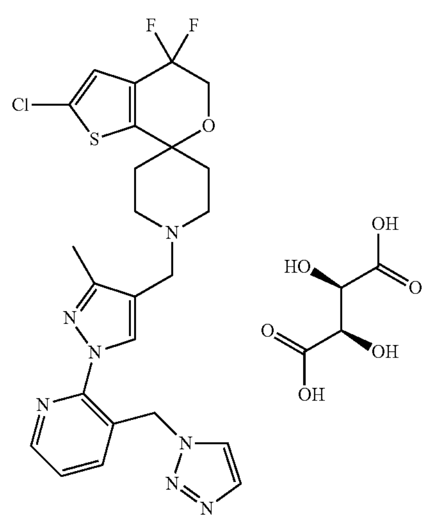 | 64 | 532 (M + 1) |

| Ex. No. | Chemical name | Structure | Yield (%) | Physical data: MS (m/z) |
|---|---|---|---|---|
| 32 | 2-Chloro-4,4-difluoro-1'-[[3-methyl-1-[3-[(2-methylimidazol-1-yl)methyl]-2-pyridyl]pyrazol-4-yl]methyl]spiro[5H-thieno[2,3-c]pyran-7,4'-piperidine] (L)-Tartrate | 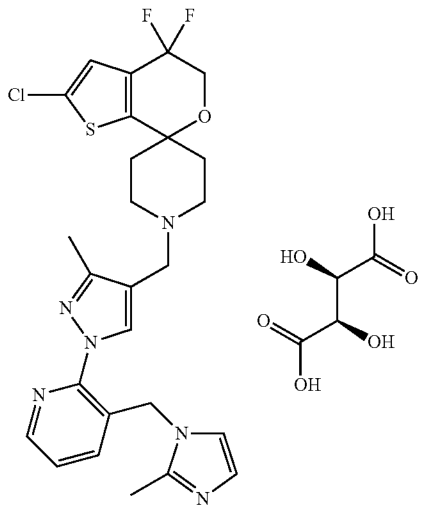 | 62 | 545 (M + 1) |
| 33 | 2,4,4-Trifluoro-1'-[[1-(3-methoxy-2-pyridyl)-3-methyl-pyrazol-4-yl]methyl]spiro[5H-thieno[2,3-c]pyran-7,4'-piperidine] (L)-Tartrate | 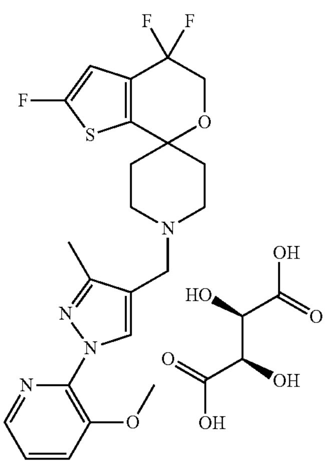 | 59 | 465 (M + 1) |
| 34 | 1'-[[1-[3-(Cyclopropylmethoxymethyl)-2-pyridyl]-3-methyl-pyrazol-4-yl]methyl]-2-fluoro-spiro[4,5-dihydrothieno[2,3-c]pyran-7,4'-piperidine] (L)-Tartrate | 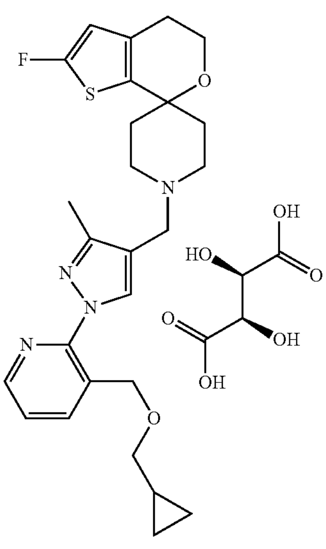 | 48 | 483 (M + 1) |

| Ex. No. | Chemical name | Structure | Yield (%) | Physical data: MS (m/z) |
|---|---|---|---|---|
| 35 | 2-Chloro-1'-[[1-[3-(cyclopropylmethoxy)-2-pyridyl]-3-methyl-pyrazol-4-yl]methyl]-4,4-difluoro-spiro[5H-thieno[2,3-c]pyran-7,4'-piperidine] (L)-Tartrate | | 76 | 521 (M + 1) |

EXAMPLE 36

2-Chloro-4,4-difluoro-1'-[[1-(3-methoxy-2-pyridyl)-3-methyl-pyrazol-4-yl]methyl]spiro[5H-thieno[2,3-c]pyran-7,4'-piperidine]

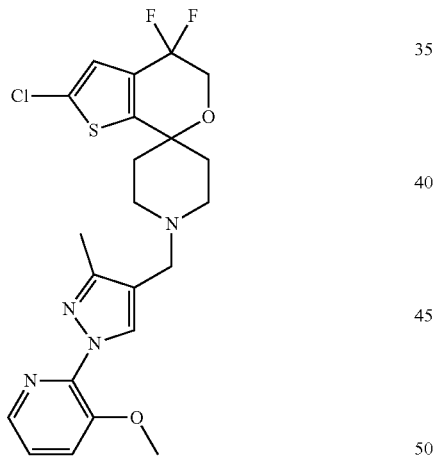

To a screw-cap test tube are added copper(I) iodide (23.74 mg, 0.125 mmol), 2-chloro-4,4-difluoro-1'-[(3-methyl-1H-pyrazol-4-yl)methyl]spiro[5H-thieno[2,3-c]pyran-7,4'-piperidine] (233.00 mg, 0.623 mmol), potassium carbonate (182.71 mg, 1.31 mmol), toluene (2 mL) (previously bubbled with nitrogen for 20 min) and a stir bar. The reaction mixture is bubbled with nitrogen for 20 minutes and then 2-iodo-3-methoxypyridine (302.01 mg, 1.25 mmol) and trans-N,N'-dimethylcyclohexane-1,2-diamine (39.31 mL, 0.25 mmol) are added. The reaction tube is quickly sealed (caution: build-up of pressure possible; use a safety shield) and immersed in a preheated oil bath at 110° C. for 24 hours with the aid of a magnetic stirrer. Then, the mixture is poured on SCX column (25 g) and eluted with methanol and then 2N solution of ammonia in methanol. The basic fraction is concentrated and the resulting residue is purified by basic-HPLC to give 162 mg of the title compound. MS (m/z): 481 (M+1).

EXAMPLE 37

2-Chloro-4,4-difluoro-1'-[[1-(3-isoxazol-3-yl-2-pyridyl)-3-methyl-pyrazol-4-yl]methyl]spiro[5H-thieno[2,3-c]pyran-7,4'-piperidine]

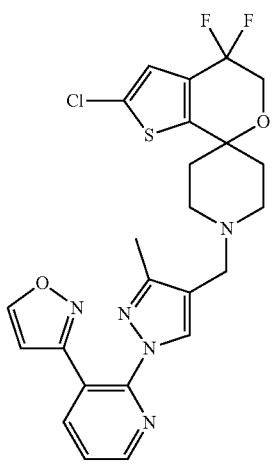

This compound is essentially prepared as described in Example 36 by using 2-chloro-4,4-difluoro-1'-[(3-methyl-1H-pyrazol-4-yl)methyl]spiro[5H-thieno[2,3-c]pyran-7,4'-piperidine] and 3-(2-bromo-pyrid-3-yl)isoxazole as starting material. Residue is purified by normal phase Isco chromatography (ethyl acetate is used as eluent) to yield 45% of the title compound: mass spectrum (m/z): 518 (M+1)

EXAMPLE 38

2-(2-(4-((2'-Chloro-4',4'-difluoro-4',5'-dihydrospiro[piperidine-4,7'-thieno[2,3-c]pyran]-1-yl)methyl)-3-methyl-1H-pyrazol-1-yl)pyridin-3-yl)propan-2-ol

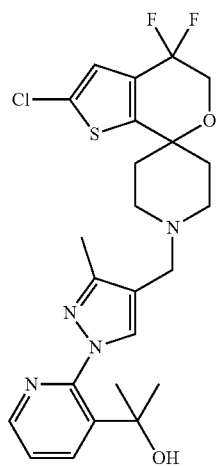

To a screw-cap test tube containing 2-(2-bromo-3-pyridyl)propan-2-ol (520 mg, 2.41 mmol) in dry dimethylformamide (3.2 mL) are added under nitrogen 4-((2'-chloro-4',4'-difluoro-4',5'-dihydrospiro[piperidine-4,7'-thieno[2,3-c]pyran]-1-yl)methyl)-3-methyl-1H-pyrazole (600 mg, 1.6 mmol), copper(I) oxide (23 mg, 160 μmoles), (R,R)-(−)-N,N'-dimethyl-1,2-cyclohexanediamine (68 mg, 480 μmoles) and cesium carbonate (1040 mg, 3.2 mmol). The reaction tube is quickly sealed (caution: build-up of pressure possible; use a safety shield) and stirred in a preheated oil bath at 110° C. for 16 h with the aid of a magnetic stirrer. The mixture is diluted with water and extracted with ethyl acetate. The organic layer is separated, dried over magnesium sulfate, filtered and the solvent evaporated in vacuo. The resulting residue is purified by silica gel using normal phase Isco chromatography eluting with hexane:ethanol (gradient from 2 to 15% in ethanol) to give 310 mg of the title compound. MS (m/z): 509 (M+1)

EXAMPLE 39

1-[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]-N-methyl-methanamine (L)-Tartrate

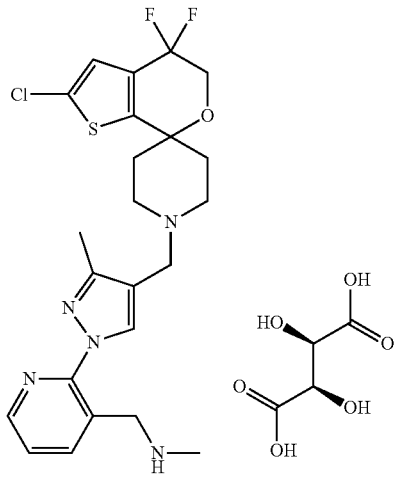

The free base of the title compound is prepared essentially as described in Preparation 7 using 2-[4-[(2-chloro-4,4-difluoro-spiro[5H-thieno[2,3-c]pyran-7,4'-piperidine]-1'-yl)methyl]-3-methyl-pyrazol-1-yl]pyridine-3-carbaldehyde and methylamine in a 51% yield. MS (m/z): 494 (M+1).

The tartrate salt is essentially prepared as described in Example 1. MS (m/z): 551 (M+1).

The compounds of Example 40-44 are prepared essentially as described in Example 39 from the corresponding aldehyde and amine. (Example 43 is prepared using 1,2-dichloroethane as the solvent)

| Ex. No. | Chemical name | Structure | Yield (%) | Physical data: MS (m/z) |
|---|---|---|---|---|
| 40 | N-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methyl]propan-2-amine (L)-Tartrate | 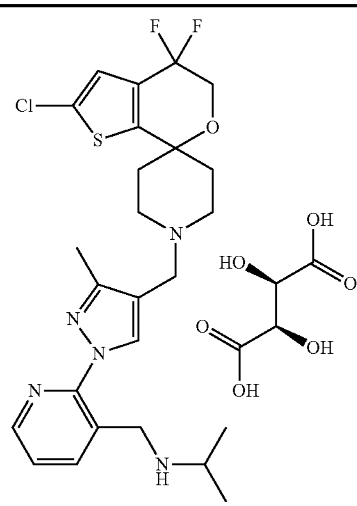 | 34 | 522 (M + 1) |

| Ex. No. | Chemical name | Structure | Yield (%) | Physical data: MS (m/z) |
|---|---|---|---|---|
| 41 | 2-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methylamino]acetonitrile (L)-Tartrate | 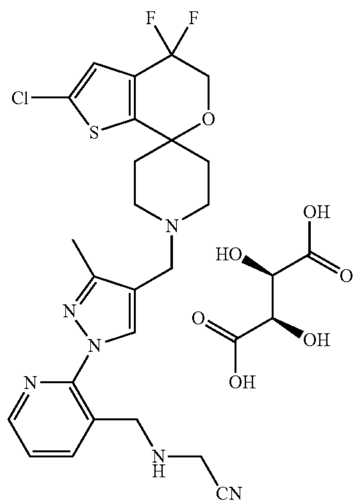 | 70 | 519 (M + 1) |
| 42 | 2-[[2-[4-[(2-Fluorospiro[4,5-dihydrothieno[2,3-c]pyran-7,4'-piperidine]-1'-yl)methyl]-3-methyl-pyrazol-1-yl]-3-pyridyl]methylamino]acetonitrile (L)-Tartrate | 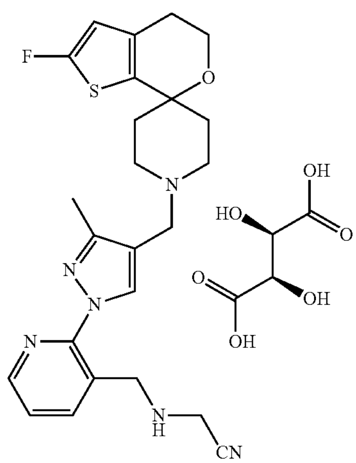 | 27 | 453 (M + 1) |

-continued

| Ex. No. | Chemical name | Structure | Yield (%) | Physical data: MS (m/z) |
|---|---|---|---|---|
| 43 | 2-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methylamino]acetamide (L)-Tartrate | 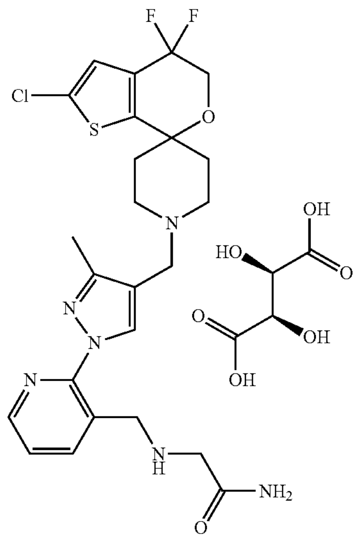 | 53 | 485 (M + 1) |
| 44 | 1-[[2-[4-[(2-Fluorospiro[4,5-dihydrothieno[2,3-c]pyran-7,4'-piperidine]-1'-yl)methyl]-3-methyl-pyrazol-1-yl]-3-pyridyl]methylamino]propan-2-one (L)-Tartrate | 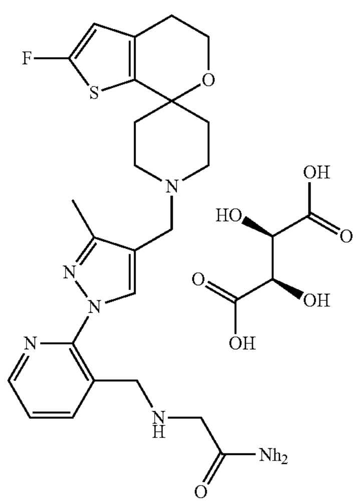 | 38 | 537 (M + 1) |

EXAMPLE 45

2-[4-[(2-Chloro-4,4-difluoro-spiro[5H-thieno[2,3-c]pyran-7,4'-piperidine]-1'-yl)methyl]-3-methyl-pyrazol-1-yl]pyridine-3-carbaldehyde oxime (L)-Tartrate

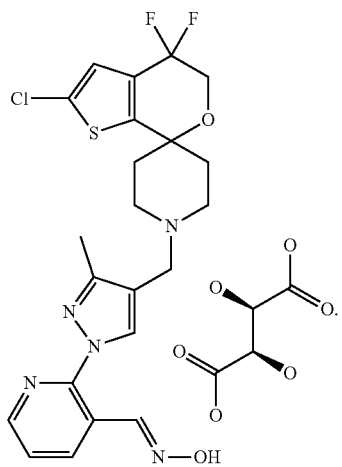

To a solution of 2-[4-[(2-chloro-4,4-difluoro-spiro[5H-thieno[2,3-c]pyran-7,4'-piperidine]-1'-yl)methyl]-3-methyl-pyrazol-1-yl]pyridine-3-carbaldehyde (0.210 g, 0.438 mmol) in ethanol (3 mL) are added hydroxylamine hydrochloride (0.038 g, 0.526 mmol) and sodium ethanoate (0.044 g, 0.526 mmol) and the mixture is stirred at reflux for 1 h. The solvent is evaporated and the residue is extracted with ethyl acetate and water. The organic layer is separated, dried over magnesium sulfate, filtered and the solvent is evaporated in vacuo. The residue is purified by basic reverse phase HPLC to yield 0.110 g of 2-[4-[(2-chloro-4,4-difluoro-spiro[5H-thieno[2,3-c]pyran-7,4'-piperidine]-1'-yl)methyl]-3-methyl-pyrazol-1-yl]pyridine-3-carbaldehyde oxime. MS (m/z): 494 (M+1).

The tartrate salt is essentially prepared as described in Example 1. MS (m/z): 494 (M+1).

The compounds of Example 46-47 are prepared essentially as described in Example 45 from the corresponding aldehyde and hydroxylamine

| Ex. No. | Chemical name | Structure | Yield (%) | Physical data: MS (m/z) |
|---|---|---|---|---|
| 46 | 1-[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]-N-methoxy-methanimine (L)-Tartrate | 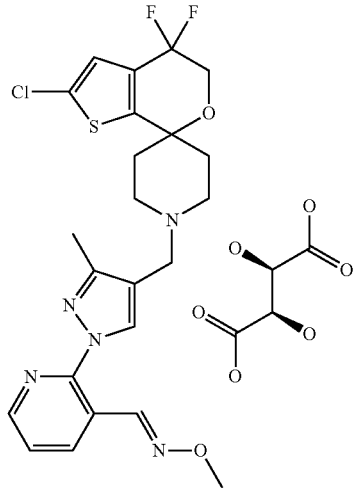 | 73 | 508 (M+1) |

-continued

| Ex. No. | Chemical name | Structure | Yield (%) | Physical data: MS (m/z) |
|---|---|---|---|---|
| 47 | 1-[2-[4-[(2-Fluorospiro[4,5-dihydrothieno[2,3-c]pyran-7,4'-piperidine]-1'-yl)methyl]-3-methyl-pyrazol-1-yl]-3-pyridyl]-N-methoxy-methanimine (L)-Tartrate | 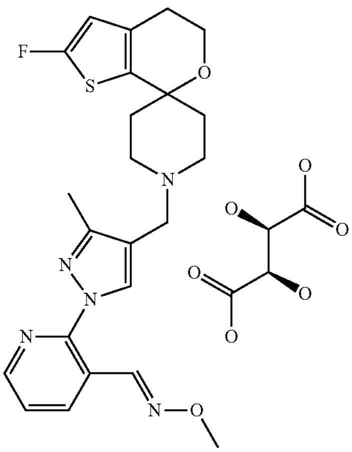 | 64 | 456 (M + 1) |

EXAMPLE 48

[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanamine (L)-Tartrate

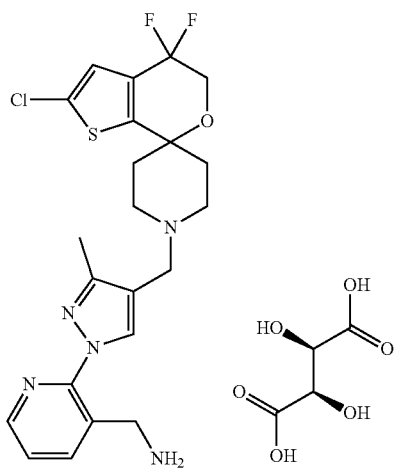

1. 2-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methyl]isoindoline-1,3-dione Diisopropyl azodicarboxylate (0.105 mL, 0.54 mmol) is added to a solution of [2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol (0.173 g, 0.36 mmol), phthalimide (0.079 mg, 0.54 mmol) and triphenylphosphine (0.142 g, 0.54 mmol) in toluene (3 mL) at 0° C. The mixture is stirred at room temperature overnight. The solvent is removed and the residue is purified first using a 2 g SCX cartridge and after evaporation of the 2 N ammonia in methanol fraction by normal phase Isco chromatography eluting with hexane/ethanol (3%-30%) to give 0.201 g of 2-[[2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methyl]isoindoline-1,3-dione. MS (m/z): 610 (M+1).

2. [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanamine (L)-Tartrate To a flask containing 2-[[2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methyl]isoindoline-1,3-dione (0.201 g, 0.33 mmol) and 24 μl of water in ethanol (2.5 mL) is added hydrazine monohydrate (0.04 g, 0.79 mmol). The reaction mixture is refluxed for 2.5 hr. and then diluted with methanol and purified using a 2 g SCX cartridge. After evaporation of the 2N ammonia in methanol fraction, the resulting product is purified by normal phase Isco chromatography eluting with ethanol and a 15% solution of ammonium hydroxide (7N in methanol) in ethanol (gradient of 25-90% of the basic eluent) yielding 129 mg of the title compound. MS (m/z): 480 (M+1).

The tartrate salt is essentially prepared as described in Example 1. MS (m/z): 480 (M+1).

EXAMPLE 49

2-[4-[(2-Fluorospiro[4,5-dihydrothieno[2,3-c]pyran-7,4'-piperidine]-1'-yl)methyl]-3-methyl-pyrazol-1-yl]pyridine-3-carboxamide (L)-Tartrate

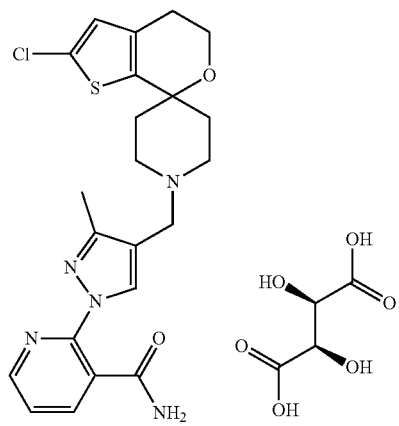

1. 2-[4-[(2-Fluorospiro[4,5-dihydrothieno[2,3-c]pyran-7,4'-piperidine]-1'-yl)methyl]-3-methyl-pyrazol-1-yl]pyridine-3-carbonitrile This compound is essentially prepared as described in Preparation 7 by using 2-fluorospiro[4,5-dihydrothieno[2,3-c]pyran-7,4'-piperidine] and 2-(4-formyl-3-methyl-pyrazol-1-yl)pyridine-3-carbonitrile. The residue is purified by SCX to give 2-[4-[(2-fluorospiro[4,5-dihydrothieno[2,3-c]pyran-7,4'-piperidine]-1'-yl)methyl]-3-methyl-pyrazol-1-yl]pyridine-3-carbonitrile in a 32% yield. MS (m/z): 424 (M+1).

2. 2-[4-[(2-Fluorospiro[4,5-dihydrothieno[2,3-c]pyran-7,4'-piperidine]-1'-yl)methyl]-3-methyl-pyrazol-1-yl]pyridine-3-carboxamide (L)-Tartrate To a solution of 2-[4-[(2-fluorospiro[2,3-c]pyran-7,4'-piperidine]-1'-yl)methyl]-3-methyl-pyrazol-1-yl]pyridine-3-carbonitrile (0.71 mmol, 0.30 g) in dimethylsulfoxide (7.5 mL), potassium carbonate (0.049 g, 0.35 mmol) is added and the mixture is cooled to 0-5° C. before adding 33% hydrogen peroxide solution in water (0.39 mL, 3.78 mmol). The mixture is stirred at room temperature for 2 h. Then, water is added carefully and the reaction mixture is extracted with ethyl acetate. Organic layer is decanted, dried over magnesium sulfate and solvent is evaporated under reduced pressure. Crude is purified by normal phase Isco chromatography using as eluent dichloromethane/methanol mixtures to give 0.252 g that are further purified by reverse phase HPLC to yield 0.198 g of 2-[4-[(2-fluorospiro[4,5-dihydrothieno[2,3-c]pyran-7,4'-piperidine]-1'-yl)methyl]-3-methyl-pyrazol-1-yl]pyridine-3-carboxamide. MS (m/z): 442 (M+1).

The tartrate salt is essentially prepared as described in Example 1. MS (m/z): 442 (M+1).

EXAMPLE 50

2-[4-[(2-Chloro-4,4-difluoro-spiro[5H-thieno[2,3-c]pyran-7,4'-piperidine]-1'-yl)methyl]-3-methyl-pyrazol-1-yl]pyridine-3-carboxamide (L)-Tartrate

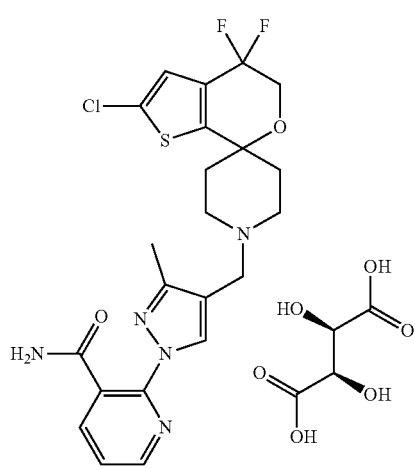

The title compound is prepared essentially as described in Example 49 by using 2-chloro-4,4-difluoro-spiro[5H-thieno[2,3-c]pyran-7,4'-piperidine] and 2-(4-formyl-3-methyl-pyrazol-1-yl)pyridine-3-carbonitrile as starting materials in a 15% overall yield (22% yield in the first step and 66% yield in the second step). MS (m/z): 494 (M+1).

EXAMPLE 51

2-[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]acetamide (L)-Tartrate

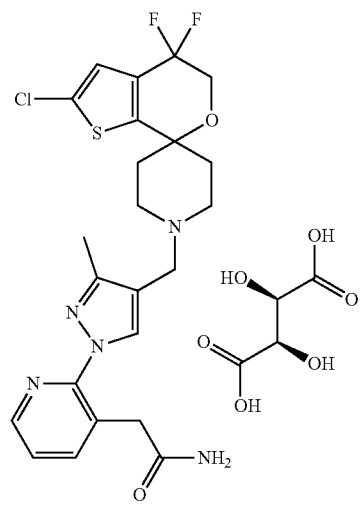

To a solution of 2-[2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]acetonitrile (170 mg, 346.96 mmoles) in dimethyl sulfoxide (4 mL) is added potassium carbonate (23.98 mg, 173.48 mmoles) and the mixture is cooled to 0-5° C. 33% Hydrogen peroxide solution in water (189.54 µL, 1.84 mmol) is added. The mixture is stirred at room temperature 16 hr. and then more 33% hydrogen peroxide solution in water (189.54 µL, 1.84 mmol) and potassium carbonate (23.98 mg, 173.48 mmoles) are added. Water is added and the mixture is extracted with ethyl acetate. The organic layer is separated, washed with brine, dried over magnesium sulfate and the solvent evaporated in vacuo. The compound is purified by normal phase Isco chromatography using dichloromethane and 2N ammonia in methanol as eluents (1.5 to 6% in 2N ammonia in methanol) to yield 19% of the free base of the title compound. MS (m/z): 508 (M+1).

The tartrate salt is prepared essentially as described in Example 1. MS (m/z): 508 (M+1).

EXAMPLE 52

[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methyl N-methylcarbamate (L)-Tartrate

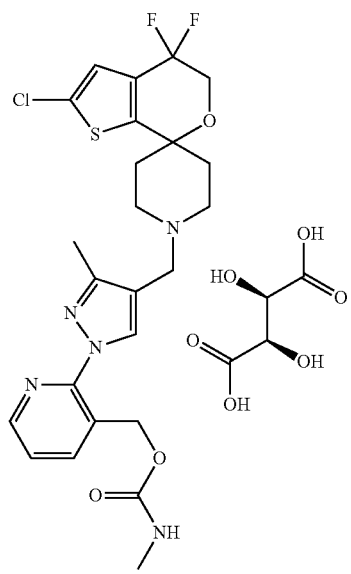

Methylisocyanate (5.80 µL, 0.096 mmol) is added to a solution of 2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol (0.042 g, 0.087 mmol) in dichloromethane (1 mL) at room temperature. After 1 h with no reaction evolution observed by LC/MS, triethylamine (12.17 µL, 87.32 µmoles) and methylisocyanate (5.8 µL, 0.096 mmol) are added and the reaction is stirred overnight. More triethylamine (12.17 µL, 87.32 µmoles) and methylisocyanate (5.8 µL, 0.096 mmol) are added and after 24 h the solvent is evaporated and the residue is purified by normal phase Isco chromatography with dichloromethane/2N ammonium hydroxide in methanol (0 to 5% in 2N ammonium hydroxide in methanol) as eluent to yield 0.041 g of [2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methyl N-methylcarbamate. MS (m/z): 538 (M+1).

The tartrate salt is essentially prepared as described in Example 1. MS (m/z): 538 (M+1).

EXAMPLE 53

[4-[(2-Chloro-4,4-difluoro-spiro[5H-thieno[2,3-c]pyran-7,4'-piperidine]-1'-yl)methyl]-1-(3-fluoro-2-pyridyl)pyrazol-3-yl]methanol (L)-Tartrate

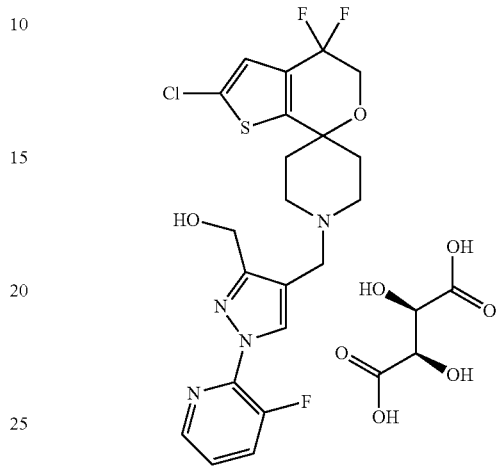

1. Ethyl 4-[(2-chloro-4,4-difluoro-spiro[5H-thieno[2,3-c]pyran-7,4'-piperidine]-1'-yl)methyl]-1-(3-fluoro-2-pyridyl)pyrazole-3-carboxylate To a solution of ethyl 1-(3-fluoro-2-pyridyl)-4-formyl-pyrazole-3-carboxylate (342.5 mg) in 1,2-dichloroethane (6.7 mL), 2-chloro-4,4-difluoro-spiro[5H-thieno[2,3-c]pyran-7,4'-piperidine] (280 mg, 1 mmol) is added. The mixture is stirred for 10 min. Then, sodium triacetoxyborohydride (442 mg) is added and the mixture is stirred overnight at room temperature. Sodium bicarbonate (saturated aqueous solution) is added and the organic phase extracted with dichloromethane, dried over magnesium sulfate and solvent evaporated in vacuo. Crude is purified by normal phase Isco chromatography using as eluent ethyl acetate and hexane to give 450 mg of ethyl 4-[(2-chloro-4,4-difluoro-spiro[5H-thieno[2,3-c]pyran-7,4'-piperidine]-1'-yl)methyl]-1-(3-fluoro-2-pyridyl)pyrazole-3-carboxylate. MS (m/z): 527 (M+1).

2. [4-[(2-Chloro-4,4-difluoro-spiro[5H-thieno[2,3-c]pyran-7,4'-piperidine]-1'-yl)methyl]-1-(3-fluoro-2-pyridyl)pyrazol-3-yl]methanol (L)-Tartrate To a solution of ethyl 4-[(2-chloro-4,4-difluoro-spiro[5H-thieno[2,3-c]pyran-7,4'-piperidine]-1'-yl)methyl]-1-(3-fluoro-2-pyridyl)pyrazole-3-carboxylate (250 mg, 0.47 mmol) in tetrahydrofuran (2.37 mL) under nitrogen atmosphere and cooled to 0° C., 1 M lithium aluminum hydride in tetrahydrofuran (569.3 µL) is added slowly. The mixture is stirred at that temperature for 30 minutes. Then, 22 µL, of water is added and the cooling bath is removed and the mixture stirred at room temperature for 5 min before adding 22 µL of 15% aqueous solution of sodium hydroxide and 65 µL, of water. Solids are filtered off and solvent evaporated. Crude is purified by normal phase Isco chromatography using as eluent dichloromethane and methanol to give 141 mg of the title compound as free base. MS (m/z): 485 (M+1).

The tartrate salt is essentially prepared as described in Example 1. MS (m/z): 485 (M+1).

Alternate Method to Make Free Base of Example 53

1. Ethyl 4-[(2-chloro-4,4-difluoro-spiro[5H-thieno[2,3-c]pyran-7,4'-piperidine]-1'-yl)methyl]-1H-pyrazole-3-carboxylate

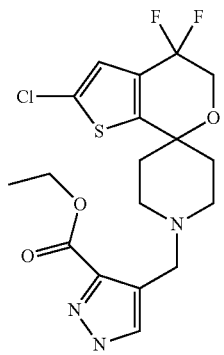

To a suspension of 2-chloro-4,4-difluoro-spiro[5H-thieno[2,3-c]pyran-7,4'-piperidine (18.3 g, 65.42 mmol) in tetrahydrofuran (0.2 L) is added ethyl 4-formyl-1H-pyrazole-3-carboxylate (10 g, 59.47 mmol) and the mixture is stirred at room temperature for 10 min. Then, powdered sodium triacetoxyborohydride (16.39 g, 77.31 mmol) is added. The mixture is stirred at room temperature for 1.5 h. Then, the reaction mixture is poured over an ice-sodium bicarbonate saturated aqueous solution (200 mL). Phases are separated. Aqueous phase is basified with NaHCO$_3$ saturated solution and extracted with ethyl acetate (100 mL). Combined organic layers are washed with NaHCO$_3$ saturated solution, dried over sodium sulfate and concentrated to give 22.5 g of the title compound. MS (m/z): 432 (M+1).

2. Ethyl 4-[(2-chloro-4,4-difluoro-spiro[5H-thieno[2,3-c]pyran-7,4'-piperidine]-1'-yl)methyl]-1-(3-fluoro-2-pyridyl)pyrazole-3-carboxylate

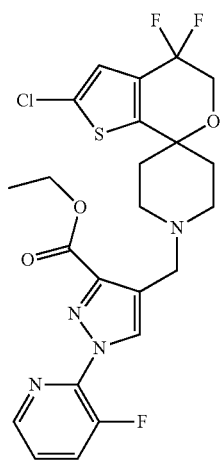

To a solution of ethyl 4-[(2-chloro-4,4-difluoro-spiro[5H-thieno[2,3-c]pyran-7,4'-piperidine]-1'-yl)methyl]-1H-pyrazole-3-carboxylate (22.5 g, 52.10 mmoles) in Dimethylformamide (225.00 mL) is added Potassium Carbonate (10.80 g, 78.14 mmoles) and 2,3-difluoropyridine (7.19 g, 62.52 mmoles) and the resulting suspension is stirred at 60° C. 15 h. Then, reaction mixture is poured over Ice/brine (30 mL) and CH$_2$Cl$_2$ (50 mL) is added to the resulting suspension. Solution is washed with H$_2$O (2×50 mL). Organics are dried over sodium sulfate and concentrated to give a crude which is purified via SiO$_2$ filtration eluting with 2-propanol/CH$_2$Cl$_2$ mixtures to give 18 g of the title compound. MS (m/z): 527 (M+1).

3. [4-[(2-Chloro-4,4-difluoro-spiro[5H-thieno[2,3-c]pyran-7,4'-piperidine]-1'-yl)methyl]-1-(3-fluoro-2-pyridyl)pyrazol-3-yl]methanol

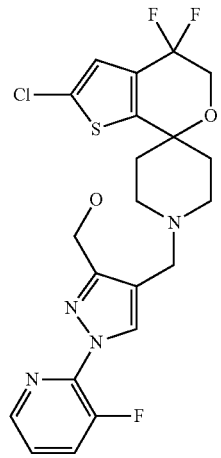

To a solution of ethyl 4-[(2-chloro-4,4-difluoro-spiro[5H-thieno[2,3-c]pyran-7,4'-piperidine]-1'-yl)methyl]-1-(3-fluoro-2-pyridyl)pyrazole-3-carboxylate (2.6 g, 4.93 mmoles) in Tetrahydrofuran (26.00 mL) under N$_2$ atmosphere and cooled to −10 C, Diisobutylaluminum Hydride 1M in toluene (23.68 mL, 23.68 mmoles) is added slowly dropwise. Then, reaction mixture is stirred at that T 15 min and then, the cold bath is removed and the mixture is warmed to room temperature. Then, H$_2$O (100 mL) is added dropwise at −10° C. The resulting suspension is extracted with EtOAc (2×30 mL). Combined organics are washed with H$_2$O (50 mL) and brine (50 mL), dried over Na$_2$SO$_4$ and concentrated to afford a light brown oil that is dissolved in methyl t-butyl ether (10 mL) and white crystals crystallized. Suspension formed is stirred and hexane (10 mL) is added dropwise while stirring. Solid is filtered to give 2 g of the title compound. MS (m/z): 485 (M+1).

EXAMPLE 54

2-(4-((2'-Chloro-4',4'-difluoro-4',5'-dihydrospiro[piperidine-4,7'-thieno[2,3-c]pyran]-1-yl)methyl)-3-methyl-1H-pyrazol-1-yl)-3-(3-methyl-1,2,4-oxadiazol-5-yl)-pyridine

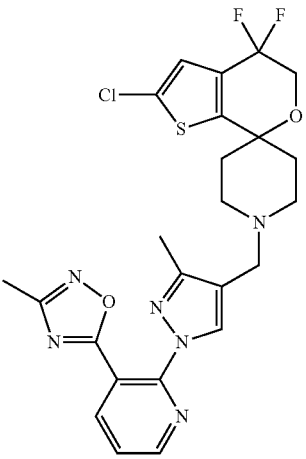

1. 2-(4-((2'-Chloro-4',4'-difluoro-4',5'-dihydrospiro[piperidine-4,7'-thieno[2,3-c]pyran]-1-yl)methyl)-3-methyl-1H-pyrazol-1-yl)-nicotinic acid methyl ester To a screw-cap test tube are added copper(I) oxide (11 mg, 0.08 mmol), 2-chloro-4,4-difluoro-1'-[(3-methyl-1H-pyrazol-4-yl)methyl]spiro[5H-thieno[2,3-c]pyran-7,4'-piperidine] (300 mg, 0.8 mmol), cesium carbonate (523 mg, 1.6 mmol), dry dimethylformamide (1.6 mL) and a stir bar. The reaction mixture is bubbled with nitrogen for 20 minutes and then methyl 2-iodopyridine-3-carboxylate (511 mg, 1.9 mmol) and trans-N,N'-dimethylcyclohexane-1,2-diamine (0.24 mmol; 34 mg) are added. The reaction tube is quickly sealed (caution: build-up of pressure possible; use a safety shield) and immersed in a preheated oil bath at 110° C. for 16 hours with the aid of a magnetic stirrer. Then, the mixture is poured on SCX column (10 g) and eluted with methanol and then 2N solution of ammonia in methanol. The basic fraction is concentrated and the resulting residue is purified by silica gel using normal phase Isco chromatography eluting with hexane:ethanol (gradient from 2 to 15% in ethanol) to give 307 mg of 2-(4-((2'-chloro-4',4'-difluoro-4',5'-dihydrospiro[piperidine-4,7'-thieno[2,3-c]pyran]-1-yl)methyl)-3-methyl-1H-pyrazol-1-yl)-nicotinic acid methyl ester. MS (m/z): 309 (M+1).

2. 2-(4-((2'-Chloro-4',4'-difluoro-4,5'-dihydrospiro[piperidine-4,7'-thieno[2,3-c]pyran]-1-yl)methyl)-3-methyl-1H-pyrazol-1-yl)-3-(3-methyl-1,2,4-oxadiazol-5-yl)-pyridine To a solution of acetamide oxime (154 mg, 2.1 mmol) in 7 mL tetrahydrofuran, are added under argon 139 mg of grinded 4A molecular sieves and sodium hydride (2.1 mmol; 84 mg as 60% in mineral oil). The mixture is allowed to stir for 30 min at 50° C. After cooling to room temperature, 2-(4-((2'-chloro-4',4'-difluoro-4',5'-dihydrospiro[piperidine-4,7'-thieno[2,3-c]pyran]-1-yl)methyl)-3-methyl-1H-pyrazol-1-yl)-nicotinic acid methyl ester (309 mg, 0.6 mmol) is added and then the mixture is heated at 50° C. for 40 min. Quenched after cooling with water and extracted with dichloromethane. After drying the organic phase with magnesium sulfate and evaporation of the solvent, the residue is diluted in methanol and purified using a 5 g SCX cartridge. The resulting residue is further purified by semipreparative reverse phase HPLC_MS using a XBridge column (Sum, 19×100 mm) and a gradient between 60 and 80% of B in A in 5 min at flow 25 mL/min (basic conditions A: ammonium bicarbonate 20 mM pH9 and B: acetonitrile) to give 71 mg of the title compound. MS (m/z): 533 (M+1).

EXAMPLE 55

2-Chloro-1'-[[1-(3-chloro-2-pyridyl)-3-methyl-pyrazol-4-yl]methyl]-4,4-difluoro-spiro[5H-thieno[2,3-c]pyran-7,4'-piperidine] (L)-Tartrate

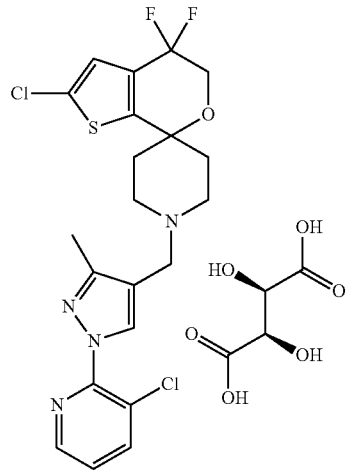

To a solution of 2'-chloro-4',4'-difluoro-4',5'-dihydrospiro[piperidine-4,7'-thieno[2,3-c]pyran] (0.2 g, 0.71 mmol) in 1,2-dichloroethane (5 mL) are added 1-(3-chloro-2-pyridyl)-3-methyl-pyrazole-4-carbaldehyde (0.19 g, 0.86 mmol) and a few drops of acetic acid. The reaction mixture is stirred at room temperature for 1 hour. Sodium triacetoxyborohydride (0.315 g, 1.43 mmol) is added and stirred at room temperature for 14 hours. After completion, the reaction mixture is diluted with dichloromethane and washed with saturated sodium bicarbonate solution and brine. The organic phase is dried over sodium sulfate and concentrated in vacuo. The crude mixture is purified by HPLC to yield 0.195 g (56%) of 2-chloro-1'-[[1-(3-chloro-2-pyridyl)-3-methyl-pyrazol-4-yl]methyl]-4,4-difluoro-spiro[5H-thieno[2,3-c]pyran-7,4'-piperidine]. MS (m/z): 485 (M+1).

The tartrate salt is essentially prepared as described in Example 1. MS (m/z): 485 (M+1).

EXAMPLE 56

2-Chloro-1'-[[1-(3-cyclopropyl-2-pyridyl)-3-methyl-pyrazol-4-yl]methyl]-4,4-difluoro-spiro[5H-thieno[2,3-c]pyran-7,4'-piperidine] (L)-Tartrate

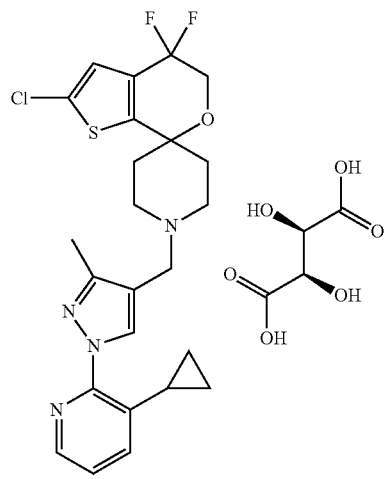

The title compound is prepared essentially as described in Example 55 by using 2'-chloro-4',4'-difluoro-4',5'-dihydrospiro[piperidine-4,7'-thieno[2,3-c]pyran] and 1-(3-cyclopropyl-2-pyridyl)-3-methyl-pyrazole-4-carbaldehyde as starting materials in a 41% yield. MS (m/z): 491 (M+1).

EXAMPLE 57

4-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methyl]morpholin-3-one

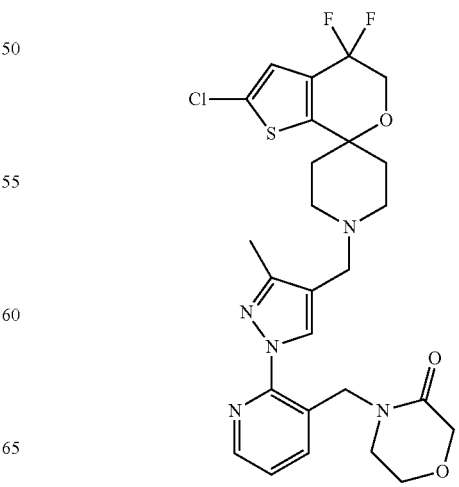

A mixture of 2-chloro-4,4-difluoro-1'-[(3-methyl-1H-pyrazol-4-yl)methyl]spiro[5H-thieno[2,3-c]pyran-7,4'-piperidine] (0.20 g, 0.53 mmol), 4-[(2-bromo-3-pyridyl)methyl]morpholin-3-one (0.21 g, 0.77 mmol), copper(I) iodide (0.015 g, 0.078 mmol) and cesium carbonate (0.36 g, 1.10 mmol) in dimethylformamide (5 mL) is degassed by bubbling argon for 15 minutes. (1R,2R)—N,N'-dimethylcyclohexane-1,2-diamine (0.02 g, 0.14 mmol) is added while degassing for 15 minutes and then the mixture is heated to 130° C. for 16 hours. After completion, the reaction mixture is allowed to cool to room temperature and filtered through celite. The residue is washed with ethyl acetate (2×25 mL) and the filtrate is washed with water (30 mL). The aqueous layer was extracted with ethyl acetate (2×25 mL) and the combined organic extracts are dried over sodium sulfate and concentrated in vacuo. The crude mixture is purified by column chromatography over silica gel eluting with dichloromethane/methanol (96:4) to yield 0.09 g (30%) of the title compound. MS (m/z): 564 (M+1).

The compounds of Example 58-59 are prepared essentially as described in Example 57 from intermediates described in preparation 49 and 50 respectively.

| Ex. No. | Chemical name | Structure | Yield (%) | Physical data: MS (m/z) |
|---|---|---|---|---|
| 58 | 1-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methyl]pyrrolidin-2-one | 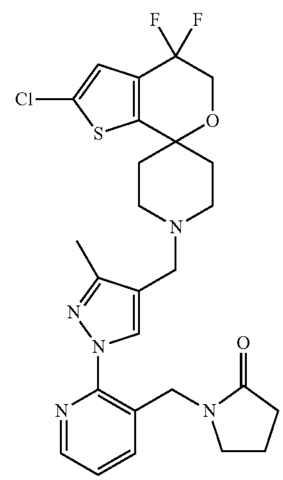 | 15 | 548 (M + 1) |
| 59 | 1-[[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methyl]piperidin-2-one | 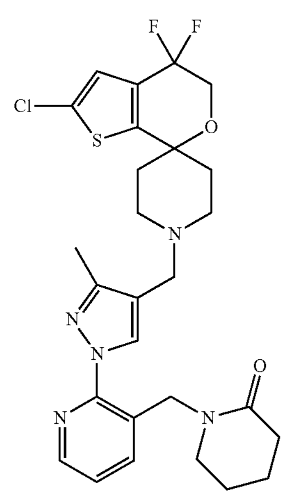 | 15 | 562 (M + 1) |

EXAMPLE 60

[4-[(2-Chloro-4,4-difluoro-spiro[5H-thieno[2,3-c]pyran-7,4'-piperidine]-1'-yl)methyl]-1-(3-chloro-2-pyridyl)pyrazol-3-yl]methanol

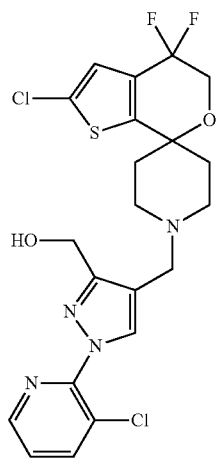

1. Ethyl 4-((2'-chloro-4',4'-difluoro-4,5'-dihydrospiro[piperidine-4,7'-thieno[2,3-c]pyran]-1-yl)methyl)-1-(3-chloro-2-pyridyl)-1H-pyrazole-3-carboxylate To a solution of 2'-chloro-4',4'-difluoro-4',5'-dihydrospiro[piperidine-4,7'-thieno[2,3-c]pyran]hydrochloride (0.35 g, 1.1 mmol) and ethyl 1-(3-chloropyridin-2-yl)-4-formyl-pyrazole-3-carboxylate (0.3 g, 1.0 mmol) in 1,2-dichloroethane (20 mL) is added N-methyl morpholine (0.33 g, 3.2 mmol) and molecular sieves (0.10 g). The reaction mixture is stirred at room temperature for 1 h. Sodium triacetoxyborohydride (0.58 g, 2.7 mmol) is added and stirred at room temperature for 16 h. After completion, the reaction mixture is filtered through celite and partitioned between dichloromethane (15 mL) and water (15 mL). The aqueous phase is extracted with dichloromethane (3×30 mL) and the combined organic extracts are dried over sodium sulfate and concentrated in vacuo. The crude mixture is purified by column chromatography over silica gel eluting with dichloromethane/methanol (98:2) to yield 0.4 g (67%) of ethyl 4-((2'-chloro-4',4'-difluoro-4',5'-dihydrospiro[piperidine-4,7'-thieno[2,3-c]pyran]-1-yl)methyl)-1-(3-chloro-2-pyridyl)-1H-pyrazole-3-carboxylate. MS (m/z): 543 (M+1).

2. [4-[(2-Chloro-4,4-difluoro-spiro[5H-thieno[2,3-c]pyran-7,4'-piperidine]-1'-yl)methyl]-1-(3-chloro-2-pyridyl)pyrazol-3-yl]methanol To a solution of ethyl 4-((2'-chloro-4',4'-difluoro-4',5'-dihydrospiro[piperidine-4,7'-thieno[2,3-c]pyran]-1-yl)methyl)-1-(3-chloro-2-pyridyl)-1H-pyrazole-3-carboxylate (0.4 g, 0.73 mmol) in tetrahydrofuran (5 mL) and ethanol (5 mL) is added lithium borohydride (1.80 mL, 2.0 M solution in tetrahydrofuran, 3.68 mmol) at 0° C. and stirred at room temperature for 16 h. After completion, the reaction mixture was quenched with water (10 mL) and extracted with ethyl acetate (2×25 mL). The combined organic extracts are dried over sodium sulfate and concentrated in vacuo. The crude mixture is purified by column chromatography over silica gel eluting with dichloromethane/methanol (97:3) to yield 0.14 g (39%) of the title compound. MS (m/z): 500 (M+1).

EXAMPLE 61

[4-[(2-Chloro-4,4-difluoro-spiro[5H-thieno[2,3-c]pyran-7,4'-piperidine]-1'-yl)methyl]-1-(3-methyl-2-pyridyl)pyrazol-3-yl]methanol

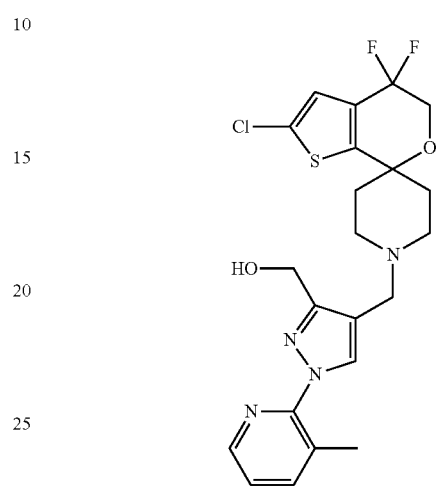

The title compound is prepared essentially as described in Example 60 by using 2'-chloro-4',4'-difluoro-4',5'-dihydrospiro[piperidine-4,7'-thieno[2,3-c]pyran]hydrochloride and 1-(3-methylpyridin-2-yl)-4-formyl-pyrazole-3-carboxylate as starting materials in a 14% yield. MS (m/z): 481 (M+1).

EXAMPLE 62

[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanol

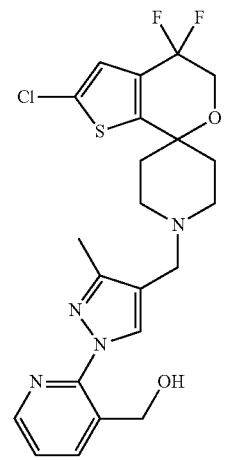

1. 2-[4-[(2-Chloro-4,4-difluoro-spiro[5H-thieno[2,3-c]pyran-7,4'-piperidine]-1'-yl)methyl]-3-methyl-pyrazol-1-yl]pyridine-3-carbaldehyde A mixture of 2-chloro-4,4-difluoro-1'-[(3-methyl-1H-pyrazol-4-yl)methyl]spiro[5H-thieno[2,3-c]pyran-7,4'-piperidine] (168.4 g, 451 mmol), CuI (12.9 g, 67.7 mmol) and potassium carbonate (131 g, 947 mmol) in anhydrous toluene (340 mL) is degassed at room temperature for 30 min.

2-Bromo-pyridine-3-carbaxaldehyde (125 g, 677 mmol) and trans-N,N'-dimethylcyclohexane-1,2-diamine (21.3 mL, 135.4 mmol) are added sequentially. The contents are degassed 30 min. before heating at 105° C. while stirring for 18 hr. LC/MS analysis of the reaction mixture reveals complete consumption of 2-chloro-4,4-difluoro-1'-[(3-methyl-1H-pyrazol-4-yl)methyl]spiro[5H-thieno[2,3-c]pyran-7,4'-piperidine]. The reaction mixture is cooled to room temperature, diluted with ethyl acetate (1.5 L), stirred and filtered through a pad of celite. The mother liquid is washed sequentially with 10% ammonium hydroxide (5×100 mL), water (3×100 mL), and brine. It is then dried (sodium sulfate), filtered and concentrated under reduced pressure. The residue is purified on silica gel using 50% ethyl acetate in hexane containing 1% triethylamine to afford 2-[4-[(2-chloro-4,4-difluoro-spiro[5H-thieno[2,3-c]pyran-7,4'-piperidine]-1'-yl) methyl]-3-methyl-pyrazol-1-yl]pyridine-3-carbaldehyde as a solid (156 g, 72% yield). MS (m/z): 479 (M+1).

2. [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanol To a solution of 2-[4-[(2-chloro-4,4-difluoro-spiro[5H-thieno[2,3-c]pyran-7,4'-piperidine]-1'-yl)methyl]-3-methyl-pyrazol-1-yl]pyridine-3-carbaldehyde (180 g, 377 mmol) in anhydrous dichloromethane (1.5 L) at 0° C. is sequentially added sodium borohydride (7.2 g, 188.5 mmol) and anhydrous methanol (0.5 L) and the contents are allowed to reach room temperature while stirring 30 min. LC/MS analysis of the reaction mixture reveals completion. Volatiles are removed under reduced pressure and the residue obtained is partitioned between dichloromethane (2 L) and water (300 mL). The layers are separated and the organic layer is sequentially washed with 1 N aqueous solution of sodium hydroxide (300 mL), water (3×300 mL), brine, dried (sodium sulfate), filtered and concentrated under reduced pressure. The residue is purified on silica gel using 50-55% ethyl acetate in hexane containing 1% triethylamine to afford [2-[4-[(2-Chloro-4,4-difluoro-spiro[5H-thieno[2,3-c]pyran-7,4'-piperidine]-1'-yl) methyl]-3-methyl-pyrazol-1-yl]-3-pyridyl]methanol as a solid (167 g, 92% yield). MS (m/z): 481 (M+1).

EXAMPLE 63

[2-[4-[(2-Chloro-4,4-difluoro-spiro[5H-thieno[2,3-c] pyran-7,4'-piperidine]-1'-yl)methyl]-3-methyl-pyrazol-1-yl]-3-pyridyl]methanol hydrochloric salt

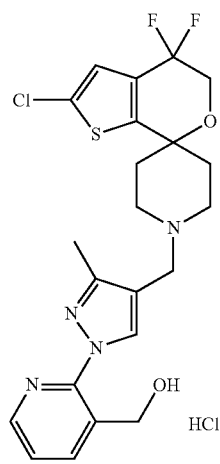

[2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanol (157.4 g, 328 mmol) in ethyl acetate (1.5 L) is heated at 80° C. until a clear solution is obtained. To the hot solution containing free base is slowly added 5-6N HCl in isopropanol (65.6 mL, 328 mmol) and the contents are stirred vigorously while allowing the mixture to reach room temperature over 2 hr. Precipitation is observed half way through the addition of HCl. The resulting white solid is filtered, washed with diethyl ether (3×1 L), dried under vacuum at 50° C. for 3 days to afford [2-[4-[(2-Chloro-4,4-difluoro-spiro [5H-thieno[2,3-c]pyran-7,4'-piperidine]-1'-yl)methyl]-3-methyl-pyrazol-1-yl]-3-pyridyl]methanol hydrochloric salt as an off-white solid (165 g, 97% yield). MS (m/z): 481 (M+1).

Receptor Occupancy Tracer Compound: 2-[(2-Fluorophenyl)methyl]-3-(2-fluorospiro[4,5-dihydrothieno [2,3-c]pyran-7,4'-piperidine]-1'-yl)-N,N-dimethyl-propanamide (L)-Tartrate

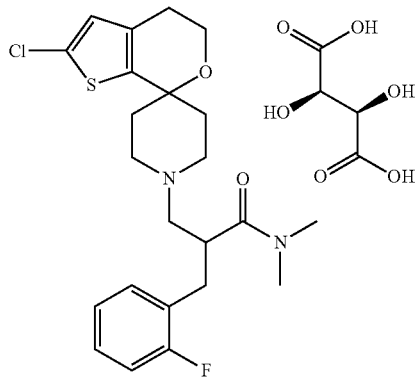

1. tert-Butyl 3-(2-fluorospiro[4,5-dihydrothieno[2,3-c]pyran-7,4'-piperidine]-1'-yl) propanoate 2-Fluorospiro[4,5-dihydrothieno[2,2-c]pyran-7,4'-piperidine] (2.7 g, 11.9 mmol) is dissolved in methanol (60 mL). Then, triethylamine (2.65 mL) and tert-butyl acrylate (3.55 mL, 23.76 mmol) is added and the mixture is heated to 65° C. for 5 h. Heat is removed and reaction mixture is stirred at room temperature overnight. Solvent is evaporated and crude is purified by normal phase Isco chromatography using ethyl acetate/hexane 1/1 as eluent to yield 4.2 g of desired compound as colorless oil. MS (m/z): 356 (M+1).

2. tert-Butyl 2-[(2-fluorophenyl)methyl]-3-(2-fluorospiro[4,5-dihydrothieno[2,3-c]pyran-7,4'-piperidine]-1'-yl)propanoate To a stirred solution of tert-butyl 3-(2-fluorospiro[4,5-dihydrothieno[2,3-c]pyran-7,4'-piperidine]-1'-yl)propanoate (4.9 g, 13.78 mmol) in tetrahydrofuran (41 mL) under $N_2$ and cooled to −78° C., lithium bis(trimethylsilyl)amide 1M (41.35 mL, 41.45 mmol) is added dropwise. The resulting mixture is stirred at that temperature for 3 hours. Then, 1,3-dimethyl-3,4,5,6-tetrahydro-2(1H)-pyrimidinone (1.33 mL, 11.03 mmol) is added, and the resulting solution is stirred at the same temperature for 30 min. To the resulting mixture, 2-fluorobenzyl bromide (2.33 mL, 19.3 mmol) in dry tetrahydrofuran (1 mL) is added and stirring is continued. The temperature is allowed to go from −78° C. to room temperature overnight. The crude reaction mixture is quenched with aqueous saturated solution of ammonium chloride and extracted with ethyl acetate. The organic layer is decanted, dried over magnesium sulfate, the solvent is evaporated and the crude obtained is purified by normal phase Isco chromatography using ethyl acetate/hexane from 5/95 to 20/80 to yield 5.06 g of the title compound obtained as colorless oil. MS (m/z): 464 (M+1).

3. 2-[(2-Fluorophenyl)methyl]-3-(2-fluorospiro[4,5-dihydrothieno[2,3-c]pyran-7,4'-piperidine]-1'-yl) propanoic acid trifluoroacetic salt A mixture of tert-butyl 2-[(2-fluorophenyl)methyl]-3-(2-fluorospiro[4,5-dihydrothieno[2,3-c]pyran-7,4'-piperidine]-1'-yl)propanoate (5.06 g, 10.91 mmol) and trifluoroacetic acid (26.20 mL, 218 mmol) is stirred at room temperature overnight. The solvent is evaporated to dryness and the crude is used without further purification.

4. 2-[(2-Fluorophenyl)methyl]-3-(2-fluorospiro[4,5-dihydrothieno[2,3-c]pyran-7,4'-piperidine]-1'-yl)-N,N-dimethyl-propanamide 2-[(2-Fluorophenyl)methyl]-3-(2-fluorospiro[4,5-dihydrothieno[2,3-c]pyran-7,4'-piperidine]-1'-yl)propanoic acid trifluoroacetic salt (5.68 g, 10.89 mmol) is dissolved in dichloromethane (218 mL), then triethylamine (12.14 mL, 87.13 mmol), dimethylamine hydrochloride (1.80 g, 21.78 mmol), 1-(3-dimethylaminopropyl)-3-ethylcarbodiimide Hydrochloride (4.18 g, 21.78 mmol), and 1-hydroxybenzotriazole hydrate (3.34 g, 21.78 mmol) are subsequently added to the solution at 0° C. The mixture is stirred at room temperature for 5 hours. The reaction mixture is treated with aqueous saturated solution of sodium bicarbonate and extracted with dichloromethane (3×20 mL). The combined organic layers are dried over magnesium sulfate and the solvent evaporated under reduced pressure. The crude is purified by normal phase Isco chromatography using dichloromethane/2N ammonium in methanol from 100/0 to 90/10 as eluent to give 4.0 g (84.5%) of the title compound. MS (m/z): 435 (M+1).

5. 2-[(2-Fluorophenyl)methyl]-3-(2-fluorospiro[4,5-dihydrothieno[2,3-c]pyran-7,4'-piperidine]-1'-yl)-N,N-dimethyl-propanamide (L)-Tartrate Enantiomeric resolution of racemic 2-[(2-fluorophenyl) methyl]-3-(2-fluorospiro[4,5-dihydrothieno[2,3-c]pyran-7,4'-piperidine]-1'-yl)-N,N-dimethyl-propanamide (2.3 g, 5.29 mmol) is carried out with a Chiralpak ADC® column (Chiral Technologies, Inc., West Chester, Pa., USA) using hexane/0.2% dimethyl ethyl amine in ethanol 9/1. The desired compound is obtained in 36% yield as the first eluting enantiomer.

The tartrate salt is essentially prepared as described in example 1. MS (m/z): 435 (M+1).

X-Ray Powder Diffraction

The XRD pattern of the crystalline solid is obtained on a Bruker D4 Endeavor X-ray powder diffractometer, equipped with a CuKα source λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. The background was removed prior to peak picking. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1° in 2θ will take into account these potential variations without hindering the unequivocal identification of the indicated crystal form. Confirmation of a crystal form may be made based on any unique combination of distinguishing peaks (in units of ° 2θ), typically the more prominent peaks.

Thus, a prepared crystalline sample of the freebase of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol is characterized by an XRD pattern using CuKα radiation as having diffraction peaks (2-theta values) as described in Table 1 below. The unique crystal form can be confirmed with a subset of distinct peaks from this complete diffraction pattern. Thus, in one embodiment the present invention provides a crystalline form of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol characterized by an XRD pattern using CuKα radiation having diffraction peaks at 11.1 in combination with one or more of the peaks selected from the group consisting of 5.5, 13.5, 17.8, and 22.3±0.1° in 2θ. In another embodiment, the present invention provides a crystalline form of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol hydrochloride characterized by an XRD pattern using CuKα radiation having diffraction peaks at 5.5, 11.1, 13.5, 17.8, and 22.3±0.1° in 2θ.

TABLE 1

X-ray powder diffraction peaks of the freebase of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol

| Peak | Angle (°2 theta) | Intensity % |
|---|---|---|
| 1 | 5.5 | 53.2 |
| 2 | 11.1 | 100 |
| 3 | 12.3 | 9.9 |
| 4 | 13.5 | 12 |
| 5 | 15.4 | 5.1 |
| 6 | 16.6 | 4.8 |
| 7 | 17.0 | 5.5 |
| 8 | 17.8 | 12.1 |
| 9 | 19.3 | 4.2 |
| 10 | 19.5 | 5.5 |
| 11 | 19.7 | 5.6 |
| 12 | 21.0 | 11.1 |
| 13 | 22.3 | 25.8 |
| 14 | 23.3 | 10.3 |
| 15 | 23.9 | 5.7 |

TABLE 1-continued

X-ray powder diffraction peaks of the freebase of
(2-{4-[(2'-chloro-4',4'-difluoro-4',5'-dihydro-1H-
spiro[piperidine-4,7'-thieno[2,3-c]pyran]-1-yl)methyl]-3-methyl-1H-
pyrazol-1-yl}pyridin-3-yl)methanol

| Peak | Angle (°2 theta) | Intensity % |
|---|---|---|
| 16 | 26.5 | 7.2 |
| 17 | 27.0 | 7.1 |

Similarly, a prepared crystalline sample of the HCl salt of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol is characterized by an XRD pattern using CuKα radiation as having diffraction peaks (2-theta values) as described in Table 2 below. The unique crystal form can be confirmed with a subset of distinct peaks from this complete diffraction pattern. Thus, in one embodiment the present invention provides a crystalline form of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol hydrochloride characterized by an XRD pattern using CuKα radiation having diffraction peaks at 16.2 in combination with one or more of the peaks selected from the group consisting of 10.8, 12.1, and 21.1±0.1° in 2θ. In another embodiment, the present invention provides a crystalline form of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol hydrochloride characterized by an XRD pattern using CuKα radiation having diffraction peaks at 10.8, 12.1, 16.2, and 21.2°±0.1° in 2θ.

TABLE 2

X-ray powder diffraction peaks of the HCl salt of (2-{4-[(2'-chloro-4',4'-difluoro-4',5'-dihydro-1H-spiro[piperidine-4,7'-thieno[2,3-c]pyran]-1-yl)methyl]-3-methyl-1H-pyrazol-1-yl}pyridin-3-yl)methanol

| Peak | Angle (°2 theta) | Intensity % |
|---|---|---|
| 1 | 10.8 | 70.5 |
| 2 | 12.1 | 41.4 |
| 3 | 16.2 | 80.1 |
| 4 | 18.7 | 60.8 |
| 5 | 19.5 | 38.6 |
| 6 | 20.6 | 49.5 |
| 7 | 21.1 | 64.9 |
| 8 | 22.3 | 33.1 |
| 9 | 23.0 | 89.6 |
| 10 | 23.5 | 100 |
| 11 | 24.0 | 43.8 |

Literature data (Przydzial and Heisler, 2008, supra; Reinscheid, 2006, supra) and data generated in nonclinical animal studies support a role for nociceptin antagonists in the treatment of depression, obesity and eating disorders, and migraine. Specifically it is found that nociceptin receptor antagonists are effective in rodent models of depression both alone and in combination with tricyclic or selective serotonergic reuptake inhibitor (SSRI) antidepressants, in rodent models of inhibiting hyperphagia, of inhibiting weight regain following previous weight loss, and in models for migraine. Moreover, studies conducted in nociceptin receptor knockout mice have demonstrated that the action of nociceptin antagonists in the forced swim test (measure of antidepressant activity) and in fasting-induced feeding (anti-obesity activity) is genotype dependent, supporting a specific mechanism of nociceptin antagonist action in these animal models. As the previously described disorders represent common co-morbid clinical conditions a nociceptin receptor antagonist may be particularly effective in these specific patient populations, such as patients with major depressive disorder, binge-eating disorder, overweight, obesity, and obesity with co-morbid clinical mood disorders.

To further demonstrate the characteristics of the present compounds, representative compounds are run in the following in vitro and in vivo assays:

In Vitro Receptor Binding

Radioligand binding assays are commonly used to determine the affinity ($K_i$) or potency of a compound to bind to a particular receptor or target protein. A filtration-based [3H]-OFQ/nociceptin receptor binding assay is developed based on previous assay formats (Ardati A, Henningsen R A, Higelin J, Reinscheid R K, Civelli O, Monsma F J Jr. *Mol. Pharmacol.* 1997 May; 51(5):816-24.) with minor modifications. [3H]-OFQ/nociceptin binding assays are carried out in deep-well 96-well plates. [³H]OFQ (final assay concentration 0.2 nM) competition studies are carried out with 5-10 μg of membrane protein (isolated from Chinese hamster ovary cells (CHO cells) expressing cloned human ORL1 receptors) in a final assay volume of 0.5 mL of buffer containing 20 mM HEPES, pH 7.4, 5 mM $MgCl_2$, 1 mM EGTA, 100 mM NaCl, 0.1% bovine serum albumin. Samples are incubated for 60 min. at room temperature, which is found to be optimal for competition assays. The assays are terminated by filtration through glass fiber filters (Wallac filtermat A) [pretreated with 0.3% polyethylenimine (Sigma) for 1 hr] on a Tometc cell harvester, and the filters are washed three times with 5 mL of ice-cold 50 mM Tris.HCl, pH 7.4. Filtermats are then dried and imbedded with Meltilex scintillant A and the radioactivity counted in a Wallac Microbeta scintillation counter. Specific binding is determined by displacement with 100 nM unlabeled nociceptin. Curves are plotted as the percent of specific binding and $IC_{50}$ values are determined using a sigmoidal dose response curve with variable slope. $K_i$ values are calculated from the $IC_{50}$ by the equation of Cheng and Prusoff (Cheng, Y. C., and Prusoff, W. H., Biochem. Pharmacol. 22, 3099-3108 (1973)) where $K_i = IC_{50} \times (1 + D \times K_d^{-1})^{-1}$.

Similarly, $K_i$ for the mu, kappa and delta opioids, serotonin, dopamine, adrenergic, mucarinic, and histamine receptors, as well as binding to the norepinephrine transporter, sodium channel, chloride channel, and calcium channel may be determined using membranes expressing the desired receptor/transporter/channels and appropriate corresponding radioligand competitor molecules.

Exemplified compounds are tested essentially as described above and are found to have high affinity for the ORL-1 receptor. $K_i$'s for the ORL-1 receptor for the exemplified compounds are found to be less than 2 nM, while the $K_i$ for other receptors/transporters/channels tested are found to be significantly greater. The compounds of Examples 62, 23, and 53 are tested essentially as described above and are found to have affinities as shown in Table 3 below.

TABLE 3

Selectivity data

| $K_i$ (nM) | Example 62 | Example 23 | Example 53 |
|---|---|---|---|
| ORL-1 | 0.18 | 0.79 | 0.45 |
| Mu Opioid | >451 | >451 | >451 |
| Kappa Opioid | >430 | >430 | >430 |
| Delta Opioid | >479 | >479 | >479 |
| 5-$HT_{1A}$ | >3180 | ND | >3180 |

TABLE 3-continued

Selectivity data

| $K_i$ (nM) | Example 62 | Example 23 | Example 53 |
|---|---|---|---|
| 5-HT$_{1B}$ | >3580 | ND | >3580 |
| 5-HT$_{1C}$ | ND | ND | ND |
| 5-HT$_{1D}$ | >8550 | ND | >8550 |
| 5-HT$_{1E}$ | >5370 | ND | >5370 |
| 5-HT$_{1F}$ | >8520 | ND | >8520 |
| 5-HT$_{2A}$ | >5000 | ND | >5000 |
| 5-HT$_{2B}$ | 693 | ND | 220 |
| 5-HT$_{2C}$ | >5650 | ND | >5650 |
| 5-HT$_4$ | >4120 | ND | >4120 |
| 5-HT$_5$ | >9090 | ND | >9090 |
| 5-HT$_6$ | ND | ND | >5830 |
| 5-HT$_7$ | >3980 | ND | >3980 |
| D$_1$ Dopamine | >5000 | ND | >5000 |
| D$_2$ Dopamine | >5000 | ND | >5000 |
| Adenosine A3 | >5000 | ND | >5000 |
| Adrenergic Alpha$_1$ | >5000 | ND | >5000 |
| Adrenergic Alpha$_2$ | >5000 | ND | >5000 |
| Adrenergic Beta$_1$ | >5000 | ND | >5000 |
| Adrenergic Beta$_2$ | >5000 | ND | >5000 |
| Histamine H1 | >5000 | ND | >5000 |
| Muscarinic M2 | >500 | ND | >5000 |
| Muscarinic M3 | >5000 | ND | >5000 |
| Norepinephrine transporter | >500 | ND | >500 |
| Na$^+$ channel | 235 | ND | >500 |
| Cl$^-$ channel | >500 | ND | >500 |
| Ca+2 channel (DHP site) | >5000 | ND | >5000 |
| Ca+2 channel (diltiazem site) | >500 | ND | >500 |
| Ca+2 channel (verapamil site) | >500 | ND | >5000 |

ND = not determined

Therefore, physiologically relevant doses of the compounds of the invention are not expected to substantially interact with these sites in vivo, and thus are expected to avoid undesired effects associated with such activity.

In Vitro Functional Blockade of Agonist-Mediated G-Protein Activation-GTPγ-[35S] Binding.

Agonist-mediated stimulation of G-protein coupled receptors results in the activation of membrane associated Gαβγ-protein heterotrimer complexes, and represents the first step in the transduction of extracellular signals to modification of intracellular pathways. The first step in activation of receptor-mediated activation of Gαβγ-proteins heterotrimer is the exchange of Gα subunit bound guanosine diphoshpate (GDP) for guanosine triphosphate (GTP). The binding of GTP to the Gα subunit causes dissociation of the heterotrimer subunits, Gβ and Gγ, resulting in the modulation of several intracellular signaling cascades. Measurement of receptor-mediated G-protein activation can be measured using the non-hydrolyzable radiolabeled analog of GTP, GTP-γ-[35S]. Utilizing this methodology, antagonist affinity (Kb) is measured in membranes expressing cloned human ORL1/nociceptin receptors using a GTP-γ-[35S] binding assay according to previously described protocols with minor modifications (DeLapp et al., *J Pharmacol Exp Ther.* 1999 May; 289(2): 946-55; Ozaki et al., *Eur J Pharmacol.* 2000 Aug. 18; 402(1-2):45-53). Assays are conducted in a 200-μl volume with the following buffer composition: 100 mM NaCl, 20 mM HEPES, 5 mM MgCl$_2$, 1 mM EDTA, 0.1% BSA, 3 μM GDP, 0.5 nM [$^{35}$S]GTPγS. ORL1 receptor membrane suspension is added at a concentration of 20 μg protein per well and receptor stimulation is achieved using 300 nM nociceptin/OFQ. Wheat germ agglutinin coated SPA beads (Amersham, Arlington Hts., IL) are added at 1 mg per well to detect membrane-bound [$^{35}$S]GTPγS. Plates are sealed and incubated for 2 hr. at room temperature. Plates are then placed at 4° C. overnight to allow the SPA beads to settle and then counted in a Wallac Microbeta. Specific [$^{35}$S]GTPγS binding is determined as the difference in CPM observed in the absence and presence of 10 μM unlabeled GTPγS. Data are plotted as the percent of specific [$^{35}$S]GTPγS bound. Curves are plotted as the percent of specific binding and IC$_{50}$ values are determined using a sigmoidal dose response curve with variable slope. Antagonist affinity (K$_b$) is estimated according to DeLapp et al., 1999 using a modification of the equation of Cheng and Prusoff (1973) where $K_b = IC_{50} \times (1 + D \times EC50^{-1})^{-1}$.

Exemplified compounds are tested essentially as described above and are found to be potent antagonists of the ORL-1 receptor. K$_b$'s for the ORL-1 receptor for exemplified compounds are found to be less than 6 nM. The compounds of Examples 1, 23, and 53 are tested essentially as described above and are found to have K$_b$'s for the ORL-1 receptor of 0.20, 1.52, and 0.62 nM, respectively.

In Vivo Receptor Occupancy

Receptor occupancy (RO) using LC/MS/MS has been established as a way to measure central target engagement of putative ORL-1 antagonist in vivo. Nociceptin/ORL1 receptor occupancy (RO) is measured in the hypothalamus, a structure which contains a high density of nociceptin/ORL1 binding sites that are inside the blood brain barrier, using a novel proprietary nociceptin/ORL1 antagonist RO tracer, 2-[(2-fluorophenyl)methyl]-3-(2-fluorospiro[4,5-dihydrothieno[2,3-c]pyran-7,4'-piperidine]-1'-yl)-N,N-dimethyl-propanamide, (RO Tracer). These measurements are made without the need for a radiolabeled tracer as previously published for other receptors with modifications (Chemet E, Martin L J, Li D, Need A B, Barth V N, Rash K S, Phebus L A. Use of LC/MS to assess brain tracer distribution in preclinical, in vivo receptor occupancy studies: dopamine D2, serotonin 2A and NK-1 receptors as examples. *Life Sci.* 78(4):340-6, 2005.). A positive correlation has been established between central nociceptin/ORL1 RO and efficacy in the modulation of the feeding behavior and forced swim test in rodents. Central nociceptin/ORL1 RO is measured at 6 or 24 hours following oral administration of the test compound to rats. Male Sprague-Dawley rats (Harlan Sprague-Dawley, Indianapolis, Ind.) are treated orally with a test compound, or vehicle (20% Captisol, 25 mM phosphate buffer, pH 2.0). At 6 or 24 hours following administration of test compound/vehicle, all animals are administered an intravenous, 3 ng/kg dose of RO Tracer. It is at the time of RO Tracer administration that RO is considered to be measured. Forty minutes after RO Tracer administration, rats are sacrificed by cervical dislocation and the hypothalamus is removed. The level of RO Tracer is measured in each tissue sample.

The centrally active literature reference standard (–)-cis-1-methyl-7-[[4-(2,6-dichlorophenyl)piperidin-1-yl]methyl]-6,7,8,9-tetrahydro-5H-benzocyclohepten-5-ol (SB612111, see Magdalena and Heisler, supra), a potent nociceptin/ORL1 receptor selective antagonist, is used as a positive control to establish the RO Tracer level associated with 100% nociceptin/ORL1 RO. SB612111 is administered intravenously at a dose of 30 mg/kg 1 hr. prior to RO Tracer (a dose that results in approximately 100% RO of hypothalamic nociceptin/ORL1 receptors).

Hypothalamic samples are homogenized in 4 volumes (w/v) of acetonitrile containing 0.1% formic acid and centrifuged at 14,000 RPM for 16 min. Supernatants are collected and diluted to a final volume of 0.3 mL with sterile water. Measurement of the RO Tracer is carried out using an Agilent model 1200 HPLC (Agilent Technologies, Palo Alto, Calif.)

and an API 4000 mass spectrometer. The chromatographic separation uses a 2.1×50 mm C18 column (Agilent part number 971700-907) and a mobile phase consisting of 38% acetonitrile in water with an overall 0.1% formic acid content. Detection of RO Tracer is accomplished by monitoring the precursor to product ion transition with a mass to charge ratio (m/z) of 435 to 239, with levels quantified by comparison to standards prepared in brain tissue homogenates. Zero percent RO is calculated as the level of RO Tracer in the hypothalamus of vehicle-pretreated animals, which represents the sum of nonspecific and specific binding (all receptors available to the tracer). The lower level of RO Tracer in animals pretreated with the very high intravenous dose of SB612111, the positive control group, represents the nonspecific binding and is assigned the value of 100% occupancy (no receptors available to the tracer). The level of RO Tracer found in hypothalamus from the test compound treated group is linearly interpolated between these two points to calculate RO for the test compound.

Exemplified compounds are tested essentially as described above and are found to have high receptor occupancy at the ORL-1 receptor. Receptor occupancies for exemplified compounds are found to be between about 40 and about 130% for 3 mg/kg dose after 6 hr., or between about 20 and about 96% RO for 3 mg/kg dose after 24 hr. The receptor occupancies for the compounds of Examples 62, 23 and 53 are assayed essentially as described above for 3 mg/kg dose after 6 hr. and are found to have 104, 80 and 83% RO, respectively. As such, it is expected that the compounds of the present invention have favorable bioavailability and penetration into the CNS to the targeted ORL-1 receptors.

hERG Channel Activity

Blockade of $K^+$-channel conductance in the heart is associated with cardiotoxicity in the form of QT-wave prolongation. The affinity (K) of the exemplified nociceptin receptor antagonists for the human ERG (hERG) $K^+$ channel is determined in HEK293 cells expressing cloned hERG using the hERG channel antagonist radioligand [3H]astemizole (2 nM final assay concentration) according to well known procedures (see for example Finlayson K, et al. (*Eur J Pharmacol.* 412(3):203-12, 2001) [3H]Astemizole binding assays are performed at the contract research company Cerep (Paris France) according to standard procedures.

Examples 62, 23, and 53 are assayed essentially as described above and are found to have low activity, with $K_i$'s of 6.08, 1.21, and 8.6 μM respectively. Comparison of the in vivo plasma concentration necessary to produce 80 percent RO ($EC_{80}$ RO) of nociceptin/ORL1 receptors in the CNS for the compound of example 62 is approximately 41 nM. As such, there is a large separation between the concentrations needed to produce physiologically relevant in vivo receptor occupancy of nociceptin/ORL1 receptors and the concentrations needed for hERG $K^+$-channel activity. Therefore, physiologically relevant doses of the compounds of the invention are not expected to substantially interact with hERG sites in vivo, and thus are expected to have no substantial effect on QT prolongation.

Forced-Swim Test in Mice (mFST)

mFST is an established in vivo assay for antidepressant activity (Li et al. *J Pharmacol Exp Ther.* 319(1):254-9, 2006.). Mice treated with known clinically effective antidepressants (selective serotonin reuptake inhibitors and/or tricyclic antidepressants) exhibit the behavior of reduced time spent immobile after being placed in a water tank, a behavior associated with despair. The mFST was used to evaluate potential antidepressant-like activity of novel nociceptin/ORL1 antagonists according to previously published methods (Li et al. *J Pharmacol Exp Ther.* 319(1):254-9, 2006.). Briefly, male NIH-Swiss mice (Harlan Sprague-Dawley, Indianapolis, Ind.) weighing between 25-30 g are used. Group housed animals are removed from the vivarium to the testing area in their own cages and allowed to adapt to the new environment for at least 1 hour before testing. Alternatively, male 129S6 wild type and nociceptin/ORL1 receptor knockout mice were used to confirm dependence of the response to compound was nociceptin/ORL1 receptor dependent. All compounds are prepared in 20% Captisol, 25 mM phosphate buffer, pH 2.0 on the day of use. Mice are placed in a cylinder (diameter: 10 cm; height: 25 cm) filled with 6 cm of water (22-25° C.) for 6 min. The duration of immobility during the last 4 min. of the 6 min. period of the test was scored. A mouse is recorded as immobile when floating motionless or making only those movements necessary to keep its head above water.

Representative compounds are tested essentially as described above and are found to significantly reduce immobilization times in wild type mice. The compounds of Examples 62, 23, and 53, are assayed essentially as described above and are found to have $ED_{60}$'s of 24.9, 9.5, and 12.9 mg/Kg respectively, with maximum effects of 45%, 58%, and 54% reductions in immobilization time, respectively. Therefore compounds of the present invention are expected to have antidepressant activity in vivo.

Furthermore, the compounds of the present invention can be used in combination with other known antidepressants to produced enhanced efficacy. The compound of Example 62 is tested essentially as described above in combination with 10 mg/kg fluoxetine and is found to significantly further reduce immobilization time over either fluoxetine or the compound of Example 62 alone. See Table 4 below.

TABLE 4

Mouse forced swim test - Combination treatment with fluoxetine

| Treatment | Immobilization Time (sec) | Std error of the mean (sec) (n = 8) |
| --- | --- | --- |
| Vehicle | 174 | 16 |
| 3 mg/Kg Ex. 62 | 163 | 17 |
| 10 mg/Kg Ex. 62 | 129 | 19 |
| 10 mg/Kg fluoxetine | 168 | 14 |
| 3 mg/Kg Ex. 62 + 10 mg/Kg fluoxetine | 97* | 19 |
| 10 mg/Kg Ex. 62 + 10 mg/Kg fluoxetine | 85* | 15 |
| 15 mg/kg Imiprimine (antidepressant positive control) | 96* | 20 |

*Statistically significant reduction over vehicle, Ex 62 alone, and fluoxetine alone.

Yet further, these effects of reduced immobilization times are not observed when ORL-1 knockout mice, a strain of mice engineered to lack the ORL-1 receptor, are used, showing that the effect is indeed mediated by the ORL-1 receptor. The compound of Example 62 is tested essentially as described above using wild type mice in one arm of the study and ORL-1 knockout mice in a second arm of the study, and is found to significantly reduce the immobilization time in the wild type mice, but showed no effect in the knockout mice. A norepinepherine reuptake inhibitor antidepressant, imiprimine, is run as a positive control and is found to reduce immobilization times in both the wild type and knockout mice to an equivalent degree, showing that the behavioral effect mediated by the norepinepherine reuptake mechanism is intact in the knockout mouse strain.

Blockade of Fasting-Induced Hyperphagia in Mice.

Blockade of fasting-induced hyperphagia in rodents is an accepted model for hyperphagic eating disorders. (Hollopeter G, Erickson J C, Seeley R J, Marsh D J, Palmiter R D. Response of neuropeptide Y-deficient mice to feeding effectors. Regul Pept. 1998 Sep. 25; 75-76:383-9.) All experiments are performed on naïve twelve-week old male wild type and ORL knockout mice maintained on a 129S6 inbred background. Mice are individually housed a minimum of 3 days prior to the onset of testing to eliminate any effects of stress due to the change from group to individual housing. Three mice/genotype are randomly assigned to each treatment group on the test day. Pre-fast body weight measurements are taken, and food is then removed from cages overnight. Mice are fasted for approximately 15 hr. The next morning, the mice are given one of three doses of drug or vehicle via oral gavage 30 min. prior to gaining access to food. Drugs are dissolved in 20% Captisol dissolved in 25 mM phosphate buffer, pH 2.0. Measurements of body weight are taken immediately prior to drug treatment or 24 hr. after access to food is restored. It is worth noting that all mice independent of genotype lose ~5-10% body weight following overnight fast. Measurements of food intake are recorded 1 hr following access to food, as indicated, by weight of food remaining at 1 hr. It should be noted that food intake measured is during the light phase, a time during which mice are typically at rest and not normally eating. Following initial testing, mice are rested for 1 week with access to unlimited chow. Following the week rest, mice are retested according to the latin-square design shown in Table 5.

TABLE 5

A Latin square design is used to determine dose response curves of anorectic action of novel ORL antagonists in wild type and ORL knockout mice.

Treatment Period

| | Treatment | | | |
|---|---|---|---|---|
| Group | A | B | C | D |
| 1 | Vehicle | A | C | B |
| 2 | A | B | Vehicle | C |
| 3 | B | C | A | Vehicle |
| 4 | C | Vehicle | B | A |

Representative compounds are tested essentially as described above and are found to significantly reduce fasting-induced hyperphagia in mice. Examples 62, 23, and 53, are assayed essentially as described above and are found to substantially block fasting-induced hyperphagia. The effect was not observed in ORL-1 knockout mouse strain, demonstrating that the effect is mediated through the ORL-1 receptor. The 5-HT$_{2C}$ agonist, mCPP is used as a positive control and is found to significantly reduce fasting induced hyperphagia equally in both wild type mice and the ORL-1 knockout mouse strain. As such, it is expected that the compounds of the present invention are useful in the treatment of overweight and/or obesity and/or for weight maintenance, as for example the treatment of binge eating.

Rat Dural Plasma Protein Extravasation (PPE) Model—Oral Dosing Protocol

All test compounds are prepared in a vehicle solution containing 20% Captisol in 25 mM phosphate buffer (pH 2.0). The positive control compound, sumatriptan, is dissolved in saline. Male Sprague-Dawley rats from Harlan Laboratories (250 to 350 g), that have been fasted overnight, are dosed with test compound, sumatriptan or vehicle by oral gavage (2 mL/kg). Fifty min. post-dose the rats are anesthetized with Nembutal (60 mg/kg, ip) and placed in a stereotaxic frame with the incisor bar set at −2.5 mm. Following a mid-line sagittal scalp incision, 2 pairs of bilateral holes were drilled through the skull (3.2 mm posteriorly, 1.8 and 3.8 mm laterally, all coordinates referenced to bregma). Pairs of stainless steel stimulating electrodes (Rhodes Medical Systems Inc), insulated except at the tips, are lowered through the holes in both hemispheres to a depth of 9.2 mm below the dura.

A solution of fluoroscein isothiocyanate (FITC) dye-labeled bovine serum albumin (BSA) (FITC-BSA) (20 mg/kg, iv), is injected into the femoral vein 2 minutes prior to electrical stimulation of the trigeminal ganglion to function as the marker for protein extravasation. Sixty minutes following dosing with test compound or vehicle, the left trigeminal ganglion is electrically stimulated for 5 minutes at a current intensity of 1.0 mA (5 Hz, 5 minutes duration).

Five minutes following stimulation, the rats are killed by exsanguination with 40 mL of saline which also rinses residual FITC/BSA out of the blood vessels. The top of the skull is removed to collect the dural membranes. The membrane samples are removed from both hemispheres, rinsed with water, and spread flat on microscope slides. The slides are dried for 15 minutes on a slide warmer and cover-slipped with a 70% glycerol/water solution.

A fluorescence microscope equipped with a grating monochromator and a spectrophotometer is used to quantify the amount of FITC-BSA dye in each dural sample. The microscope is equipped with a motorized stage interfaced with a personal computer. This facilitates the computer-controlled movement of the stage, with fluorescence measurements at 25 points (500 µm steps) on each dural sample. The extravasation induced by electrical stimulation of the trigeminal ganglion is an ipsilateral effect (that is occurs only on the side of the dura in which the trigeminal ganglion is stimulated). This allows the other (unstimulated) half of the dura to be used as a control. The extravasation ratio (that is the ratio of the amount of extravasation in the dura from the stimulated side compared to the unstimulated side) is calculated. Animals dosed with vehicle alone or an ineffective dose of the test compound have an extravasation ratio of approximately 2, while totally effective treatments result in a ratio of approximately 1.

Results are expressed as mean values with standard errors of the mean (±SEM). All statistical evaluations are conducting utilizing ANOVA followed by comparison to the control group by Dunnett's Method. Statistical significance is assumed when $p<0.05$. Statistical analyses are performed using JMP statistical analysis software (SAS Research Institute, version 6.0.2).

The compound of Example 62 is tested essentially as described above and is found to effectively block extravasation in a dose dependent manner. (See Table 5 below.) As a result, it is expected that the compounds of the present invention are useful in the treatment of migraine.

TABLE 5

Rat dural plasma protein extravasation assay (PPE) for the compound of Example 62.

| Treatment (po) | Extravasation Ratio (mean) | s.e.m. | n |
|---|---|---|---|
| vehicle | 1.91 | 0.04 | 4 |
| Ex. 62 (0.1 mg/kg) | 1.83 | 0.06 | 3 |
| Ex. 62 (1.0 mg/kg) | 1.44* | 0.08 | 3 |
| Ex. 62 (10.0 mg/kg) | 1.20* | 0.03 | 3 |
| Ex. 62 (30.0 mg/kg) | 1.14* | 0.05 | 3 |
| Sumatriptan (1.0 mg/kg) | 1.06* | 0.01 | 3 |

*Statistically significant vs. Vehicle.

Stability Toward Reactive Metabolite Formation

Literature precedent suggests a correlation between reactive metabolite formation and clinical toxicities known as idiosyncratic drug reactions (IDRs), although a direct causal effect has not been established. Assuming that reactive metabolites may play a role in clinical IDRs, minimizing the potential for oxidative bioactivation has been proposed as a means of improving the overall safety profile of compounds containing structural features associated with such reactivity. (see Baillie, Thomas A., Approaches to the Assessment of Stable and Chemically Reactive Drug Metabolites in Early Clinical Trials, *Chemical Research in Toxicology*, vol 22(2) 2009.) To this end, representative compounds of the present invention and related compounds are screened using a rat hepatic microsomal trapping assay, using glutathione as an endogenous nucleophile, to understand the potential for oxidative bioactivation of the thienyl moiety. Of the compounds tested, those wherein $R^{2a}$ and $R^{2b}$ are hydrogen are found to show evidence of glutathione conjugate formation suggestive of oxidation on the thienyl moiety. Of the compounds tested, those wherein $R^{2a}$ and $R^{2b}$ are fluoro are found to not show glutathione conjugate formation. (See Table 3, below.) The lack of glutathione conjugate formation for the gem-difluoro containing molecules suggests that the gem-difluoro substituent reduces the inherent chemical propensity for bioactivation as tested in the assay.

TABLE 3

| Glutathione conjugate formation in hepatic microsomal homogenate | |
|---|---|
| Compound | Glutathione conjugate formation |
| 3-fluoro-2-[4-[(2-fluorospiro[4,5-dihydrothieno[2,3-c]pyran-7,4'-piperidine]-1'-yl)methyl]-3-methyl-pyrazol-1-yl]benzamide (L) Tartrate | Yes |
| 3-fluoro-2-[4-[(2,3-difluorospiro[4,5-dihydrothieno[2,3-c]pyran-7,4'-piperidine]-1'-yl)methyl]-3-methyl-pyrazol-1-yl]benzamide (L) Tartrate | Yes |
| (Ex. 14) 2-Chloro-1'-[[1-[3-(methoxymethyl)-2-pyridyl]-3-methyl-pyrazol-4-yl]methyl]spiro[4,5-dihydrothieno[2,3-c]pyran-7,4'-piperidine] (L) Tartrate | Yes |
| (Ex. 10) 2,4,4-Trifluoro-1'-[[1-[3-(methoxymethyl)-2-pyridyl]-3-methyl-pyrazol-4-yl]methyl]spiro[5H-thieno[2,3-c]pyran-7,4'-piperidine] (L) Tartrate | No |
| (Ex. 18) 3-fluoro-2-[3-methyl-4-[(2,4,4-trifluorospiro[5H-thieno[2,3-c]pyran-7,4'-piperidine]-1'-yl)methyl]pyrazol-1-yl]benzamide (L) Tartrate | No |

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, intranasal, transdermal, subcutaneous, intravenous, intramuscular, and pulmonary. Such pharmaceutical compositions and processes for preparing them are well known in the art. See, e.g., Remington: The Science and Practice of Pharmacy (University of the Sciences in Philadelphia, ed., 21st ed., Lippincott Williams & Wilkins Co., 2005).

The compositions are preferably formulated in a unit dosage form, each dosage containing from about 0.1 to about 500 mg, more usually about 1.0 to about 200 mg, as for example between about 5 and 50 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.01 to about 50 mg/kg, more usually from about 0.05 to 5.0 mg/kg, and as for example between 0.1 and 1.0 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula:

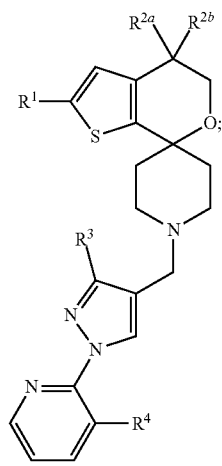

wherein
$R^1$ is fluoro or chloro;
$R^{2a}$ and $R^{2b}$ are each hydrogen or are each fluoro;
$R^3$ is hydrogen, methyl, hydroxymethyl, or ($C_1$-$C_3$) alkoxymethyl;
$R^4$ is selected from the group consisting of fluoro, chloro, cyano, cyanomethyl, ($C_1$-$C_3$) alkyl, cyclopropyl, hydroxymethyl, methoxy, cyclopropylmethoxy, aminocarbonylmethoxy, ($C_1$-$C_3$) alkoxymethyl, cyclopropyloxymethyl, cyclopropylmethoxymethyl, 1-hydroxy-1-methylethyl, aminocarbonyloxymethyl, methylaminocarbonyloxymethyl, dimethylaminocarbonyloxymethyl, aminocarbonyl, aminocarbonylmethyl, —$CH_2$—$NR^5R^6$, hydroxyimine, methoxyimine, morpholin-4-yl, morpholin-4-ylmethyl, $Ar^1$, —$CH_2Ar^1$, tetrahydrofuran-2-yl, 3-oxomorpholin-4-ylmethyl, 2-oxopyrrolidin-1-ylmethyl, and 2-oxopiperidin-1-ylmethyl;
$R^5$ is hydrogen, $C_1$-$C_3$ alkyl, cyanomethyl, —C(O)$CH_3$, or aminocarbonylmethyl;
$R^6$ is hydrogen or methyl; and Ar¹ is a moiety selected from the group consisting of imidizol-1-yl, imidizol-2-yl, 2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1,2,4-oxadiazol-5-yl; or a pharmaceutically acceptable salt thereof.

2. The compound of claim 1 wherein R¹ is chloro, or a pharmaceutically acceptable salt thereof.

3. The compound of claim 1 wherein $R^{2a}$ and $R^{2b}$ are each fluoro, or a pharmaceutically acceptable salt thereof.

4. The compound of claim 1 wherein R¹ is fluoro and $R^{2a}$ and $R^{2b}$ are each hydrogen, or a pharmaceutically acceptable salt thereof.

5. The compound of claim 1 wherein R³ is methyl, or a pharmaceutically acceptable salt thereof.

6. The compound of claim 1 wherein R⁴ is fluoro, hydroxymethyl, methoxymethyl, or pyrazol-1-ylmethyl, or a pharmaceutically acceptable salt thereof.

7. The compound according to claim 1 which is
[2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol;
2-chloro-4,4-difluoro-1'-[[3-methyl-1-[3-(pyrazol-1-ylmethyl)-2-pyridyl]pyrazol-4-yl]methyl]spiro[5H-thieno[2,3-c]pyran-7,4'-piperidine]; or
[4-[(2-chloro-4,4-difluoro-spiro[5H-thieno[2,3-c]pyran-7,4'-piperidine]-1'-yl)methyl]-1-(3-fluoro-2-pyridyl)pyrazol-3-yl]methanol; or a pharmaceutically acceptable salt thereof.

8. The compound according to claim 1 which is [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanol, or a pharmaceutically acceptable salt thereof.

9. A pharmaceutical composition comprising a compound of the formula:

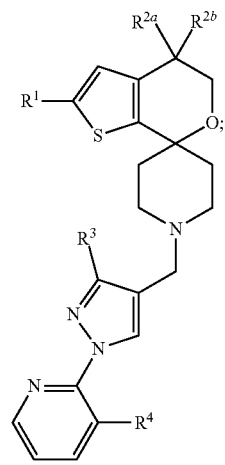

wherein
R¹ is fluoro or chloro;
$R^{2a}$ and $R^{2b}$ are each hydrogen or are each fluoro;
R³ is hydrogen, methyl, hydroxymethyl, or ($C_1$-$C_3$) alkoxymethyl;
R⁴ is selected from the group consisting of fluoro, chloro, cyano, cyanomethyl, ($C_1$-$C_3$) alkyl, cyclopropyl, hydroxymethyl, methoxy, cyclopropylmethoxy, aminocarbonylmethoxy, ($C_1$-$C_3$) alkoxymethyl, cyclopyloxymehty, cyclopropylmethoxymethyl, 1-hydroxy-1-methylethyl, aminocarbonyloxymethyl, methylaminocarbonyloxymethyl, dimethylaminocarbonyloxymethl, aminocarbonyl, aminocarbonylmethyl, —$CH_2$—$NR^5R^6$, hydroxyimine, methoxyimine, morpholin-4-yl, morpholin-4-ylmethyl, Ar¹, —$CH_2Ar^1$, tetrahydrofuran-2-yl, 3-oxomorpholin-4-ylmethyl, 2-oxopyrrolidin-1-ylmethyl, and 2-oxopiperidin-1-ylmethyl;
R⁵ is hydrogen, $C_1$-$C_3$ alkyl, cyanomethyl, —C(O)$CH_3$, or aminocarbonylmethyl;
R⁶ is hydrogen or methyl; and
Ar¹ is a moiety selected from the group consisting of imidizol-1-yl, imidizol-2-yl, 2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1,2,4-oxadiazol-5-yl;

or a pharmaceutically acceptable salt thereof, and a pharmaceutically acceptable carrier, diluent, or excipient.

10. The pharmaceutical composition of claim 9 further comprising at least one additional therapeutic ingredient.

11. The pharmaceutical composition of claim 10 where the additional therapeutic ingredient is an SSRI antidepressant.

12. A method of treating obesity or over weight in a human comprising administering to a human in need of such treatment an effective amount of a compound of the formula:

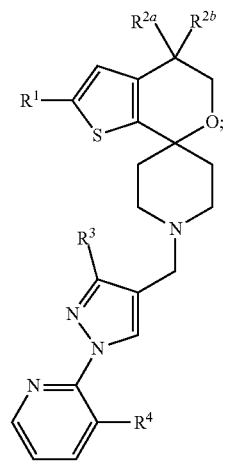

wherein
R¹ is fluoro or chloro;
$R^{2a}$ and $R^{2b}$ are each hydrogen or are each fluoro;
R³ is hydrogen, methyl, hydroxymethyl, or ($C_1$-$C_3$) alkoxymethyl;
R⁴ is selected from the group consisting of fluoro, chloro, cyano, cyanomethyl, ($C_1$-$C_3$) alkyl, cyclopropyl, hydroxymethyl, methoxy, cyclopropylmethoxy, aminocarbonylmethoxy, ($C_1$-$C_3$) alkoxymethyl, cyclopropyloxymethyl, cyclopropylmethoxymethyl, 1-hydroxy-1-methylethyl, aminocarbonyloxymethyl, methylaminocarbonyloxymethyl, dimethylaminocarbonyloxymethl, aminocarbonyl, aminocarbonylmethyl, —$CH_2$—$NR^5R^6$, hydroxyimine, methoxyimine, morpholin-4-yl, morpholin-4-ylmethyl, Ar¹, —$CH_2Ar^1$, tetrahydrofuran-2-yl, 3-oxomorpholin-4-ylmethyl, 2-oxopyrrolidin-1-ylmethyl, and 2-oxopiperidin-1-ylmethyl;
R⁵ is hydrogen, $C_1$-$C_3$ alkyl, cyanomethyl, —C(O)$CH_3$, or aminocarbonylmethyl;
R⁶ is hydrogen or methyl; and Ar¹ is a moiety selected from the group consisting of imidizol-1-yl, imidizol-2-yl,
2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1,2,4-oxadiazol-5-yl;

or a pharmaceutically acceptable salt thereof.

13. A method of treating migraine in a human comprising administering to a human in need of such treatment an effective amount of a compound of the formula:

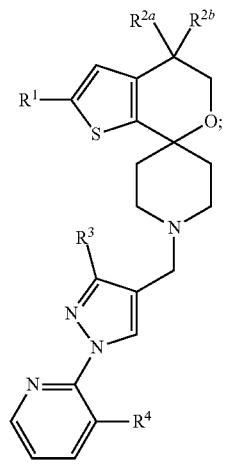

wherein

R¹ is fluoro or chloro;

R²ᵃ and R²ᵇ are each hydrogen or are each fluoro;

R³ is hydrogen, methyl, hydroxymethyl, or (C₁-C₃) alkyl,

R⁴ is selected from the group consisting of fluoro, chloro, cyano, cyanomethyl, (C₁-C₃) alkyl, cyclopropyl, hydroxymethyl, methoxy, cyclopropylmethoxy, aminocarbonylmethoxy, (C₁-C₃) alkoxymethyl, cyclopropyloxymethyl, cyclopropylmethoxymethyl, 1-hydroxy-1-methylethyl, aminocarbonyloxymethyl, methylaminocarbonyloxymethyl, dimethylaminocarbonyloxymethyl, aminocarbonyl, aminocarbonylmethyl, —CH₂—NR⁵R⁶, hydroxyimine, methoxyimine, morpholin-4-yl, morpholin-4-ylmethyl, Ar¹, —CH₂Ar¹, tetrahydrofuran-2-yl, 3-oxomorpholin-4-ylmethyl, 2-oxopyrrolidin-1-ylmethyl, and 2-oxopiperidin-1-ylmethyl;

R⁵ is hydrogen, C₁-C₃ alkyl, cyanomethyl, —C(O)CH₃, or aminocarbonylmethyl;

R⁶ is hydrogen or methyl; and

Ar¹ is a moiety selected from the group consisting of imidizol-1-yl, imidizol-2-yl,
2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1,2,4-oxadiazol-5-yl;

or a pharmaceutically acceptable salt thereof.

14. A method of treating depression in a human comprising administering to a human in need of such treatment an effective amount of a compound of the formula:

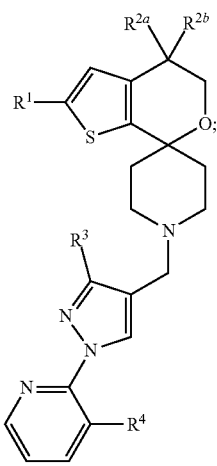

wherein

R¹ is fluoro or chloro;

R²ᵃ and R²ᵇ are each hydrogen or are each fluoro;

R³ is hydrogen, methyl, hydroxymethyl, or (C₁-C₃) alkoxymehtyl;

R⁴ is selected from the group consisting of fluoro, chloro, cyano, cyanomethyl, (C₁-C₃) alkyl, cyclopropyl, hydroxymethyl, methoxy, cyclopropylmethoxy, aminocarbonylmethoxy, (C₁-C₃) alkoxymethyl, cyclopropyloxymethyl, cyclopropylmethoxymethyl, 1-hydroxy-1-methylethyl, aminocarbonyloxymethyl, methylaminocarbonyloxymethyl, dimethylaminocarbonyloxymethyl, aminocarbonyl, aminocarbonylmethyl, —CH₂—NR⁵R⁶, hydroxyimine, methoxyimine, morpholin-4-yl, morpholin-4-ylmethyl, Ar¹, —CH₂Ar¹, tetrahydrofuran-2-yl, 3-oxomorpholin-4-ylmethyl, 2-oxopyrrolidin-1-ylmethyl, and 2-oxopiperidin-1-ylmethyl;

R⁵ is hydrogen, C₁-C₃ alkyl, cyanomethyl, —C(O)CH₃, or aminocarbonylmethyl;

R⁶ is hydrogen or methyl; and

Ar¹ is a moiety selected from the group consisting of imidizol-1-yl, imidizol-2-yl, 2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1, 2,4-oxadiazol-5-yl;

or a pharmaceutically acceptable salt thereof.

15. The pharmaceutical composition of claim 9 where the compound is

[2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol;

2-chloro-4,4-difluoro-1'-[[3-methyl-1-[3-(pyrazol-1-ylmethyl)-2-pyridyl]pyrazol-4-yl]methyl]spiro[5H-thieno[2,3-c]pyran-7,4'-piperidine]; or

[4-[(2-chloro-4,4-difluoro-spiro[5H-thieno[2,3-c]pyran-7,4'-piperidine]-1'-yl)methyl]-1-(3-fluoro-2-pyridyl)pyrazol-3-yl]methanol; or a pharmaceutically acceptable salt thereof.

16. The pharmaceutical composition of claim 9 where the compound is [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanol, or a pharmaceutically acceptable salt thereof.

17. The method of claim 12 where the compound is [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl] methanol, or a pharmaceutically acceptable salt thereof.

18. The method of claim 13 where the compound is [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl] methanol, or a pharmaceutically acceptable salt thereof.

19. The method of claim 14 where the compound is [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl] methanol, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,232,289 B2 |
| APPLICATION NO. | : 12/943187 |
| DATED | : July 31, 2012 |
| INVENTOR(S) | : Ana Belen Benito Collado et al. |

It is certified that error appears in the above-identified patent and that said Letters Patent is hereby corrected as shown below:

On the Title page, Item [56]:

First Page, Col. 2, Line 3, Delete "Exerimental" and insert -- Experimental --.

Column 2, Line 10, delete "Spirocyclic # Receptor Ligands" and insert -- Spirocyclic σ Receptor Ligands --.

Column 2, Line 11, delete "4#-thieno" and insert -- 4'-thieno --.

Column 101, Line 65-66, In Claim 9, delete "cyclopropyloxymehty," and insert -- cyclopropyloxymethyl --.

Column 102, Line 1-2, In Claim 9, delete "dimethylaminocarbonyloxymethl," and insert -- dimethylaminocarbonyloxymethyl --.

Column 102, Line 58-59, In Claim 12, delete "dimethylaminocarbonyloxymethl," and insert -- dimethylaminocarbonyloxymethyl --.

Column 103, Line 39, In Claim 13, delete "($C_1$-$C_3$) alkyl," and insert -- ($C_1$-$C_3$) alkoxymethyl --.

Column 104, Line 25, In Claim 14, delete "alkoxymehtyl;" and insert -- alkoxymethyl --.

Signed and Sealed this
Eighteenth Day of September, 2012

David J. Kappos
*Director of the United States Patent and Trademark Office*